(12) United States Patent
Yang et al.

(10) Patent No.: US 10,653,426 B2
(45) Date of Patent: May 19, 2020

(54) THROMBORESISTANT COATINGS FOR ANEURYSM TREATMENT DEVICES

(71) Applicant: Imperative Care, Inc., Sunnyvale, CA (US)

(72) Inventors: Yi Yang, San Francisco, CA (US); Tiffany C. Suekama, San Jose, CA (US); Syed Hossainy, Hayward, CA (US); Viet Ton, Sunnyvale, CA (US); Farhad Khosravi, Los Altos Hills, CA (US); Alex Jared Rowson, Morgan Hill, CA (US); Benjamin Robert Palone, Carmel, CA (US); Henry Lao, Milpitas, CA (US)

(73) Assignee: Incept, LLC, Campbell, CA (US)

( * ) Notice: Subject to any disclaimer, the term of this patent is extended or adjusted under 35 U.S.C. 154(b) by 140 days.

(21) Appl. No.: 15/862,488

(22) Filed: Jan. 4, 2018

(65) Prior Publication Data

US 2018/0193026 A1 Jul. 12, 2018

Related U.S. Application Data

(60) Provisional application No. 62/443,552, filed on Jan. 6, 2017.

(51) Int. Cl.
*A61B 17/12* (2006.01)
*A61F 2/90* (2013.01)
(Continued)

(52) U.S. Cl.
CPC .... *A61B 17/12118* (2013.01); *A61B 17/1214* (2013.01); *A61B 17/3415* (2013.01);
(Continued)

(58) Field of Classification Search
CPC .......... A61B 17/12118; A61B 17/1214; A61B 17/12145; A61B 17/1215; A61B 17/3415;
(Continued)

(56) References Cited

U.S. PATENT DOCUMENTS 4,319,580 A 3/1982 Colley et al.
4,611,594 A 9/1986 Grayhack et al.
(Continued)

FOREIGN PATENT DOCUMENTS

EP 0 309 471 8/1996
EP 1 349 486 3/2008
(Continued)

OTHER PUBLICATIONS

Invitation to Pay Additional Fees for International Application No. PCT/US18/12396 dated Mar. 22, 2018.
(Continued)

*Primary Examiner* — Jocelin C Tanner
(74) *Attorney, Agent, or Firm* — Knobbe Martens Olson & Bear, LLP

(57) ABSTRACT

Disclosed are coating compositions, processes, and designs for endowing vascular devices with thromboresistant and endothelializing properties. Also disclosed are designs of vascular devices used as aneurysm treating devices for assisting in the delivery, packing, and maintenance of embolization coils within an aneurysm, particularly a neurovascular aneurysm.

55 Claims, 27 Drawing Sheets

(51) Int. Cl.
  *A61F 2/966* (2013.01)
  *A61B 17/34* (2006.01)
  *A61F 2/00* (2006.01)
  *A61F 2/82* (2013.01)

(52) U.S. Cl.
  CPC ............... *A61F 2/90* (2013.01); *A61F 2/966* (2013.01); *A61B 17/1215* (2013.01); *A61B 17/12145* (2013.01); *A61B 2017/1205* (2013.01); *A61B 2017/12054* (2013.01); *A61F 2002/0091* (2015.04); *A61F 2002/823* (2013.01); *A61F 2002/9665* (2013.01); *A61F 2230/0069* (2013.01); *A61F 2250/0039* (2013.01)

(58) Field of Classification Search
  CPC ............ A61B 17/221; A61B 17/12168; A61B 2017/12054; A61B 2017/2212; A61B 2017/12113; A61F 2/90; A61F 2/966; A61F 2002/0091; A61F 2002/823; A61F 2002/9665; A61F 2230/0069; A61F 2250/0039
  See application file for complete search history.

(56) References Cited

U.S. PATENT DOCUMENTS

| | | |
|---|---|---|
| 4,762,129 A | 8/1988 | Bonzel |
| 4,810,582 A | 3/1989 | Gould et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,234,416 A | 8/1993 | Macaulay et al. |
| 5,243,997 A | 9/1993 | Uflacker |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,766,191 A | 6/1998 | Trerotola |
| 5,776,141 A | 7/1998 | Klein et al. |
| 5,827,242 A | 10/1998 | Follmer |
| 5,843,103 A | 12/1998 | Wulfman |
| 5,885,209 A | 3/1999 | Green |
| 5,891,114 A | 4/1999 | Chien et al. |
| 5,895,398 A | 4/1999 | Wensel |
| 5,899,892 A | 5/1999 | Mortier et al. |
| 5,916,192 A | 6/1999 | Nita et al. |
| 6,007,530 A | 12/1999 | Dornhofer et al. |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 * | 1/2001 | Bates ............... A61F 2/013 606/114 |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,355,027 B1 | 3/2002 | Le et al. |
| 6,394,976 B1 | 5/2002 | Winston et al. |
| 6,451,005 B1 | 9/2002 | Saitou et al. |
| 6,468,219 B1 | 10/2002 | Njemanze |
| 6,482,217 B1 | 11/2002 | Pintor et al. |
| 6,524,303 B1 | 2/2003 | Garibaldi et al. |
| 6,554,820 B1 | 4/2003 | Wendlandt |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,669,670 B1 | 12/2003 | Muni et al. |
| 6,824,550 B1 | 11/2004 | Pintor et al. |
| 6,977,068 B1 | 12/2005 | Nair et al. |
| 7,037,267 B1 | 5/2006 | Lipson et al. |
| 7,104,979 B2 | 9/2006 | Jansen et al. |
| 7,232,452 B2 | 6/2007 | Adams et al. |
| 7,309,334 B2 | 12/2007 | von Hoffman |
| 7,507,229 B2 | 3/2009 | Hewitt et al. |
| 7,537,568 B2 | 5/2009 | Moehring |
| 7,558,622 B2 | 7/2009 | Tran |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,905,891 B2 | 3/2011 | Self |
| 7,931,659 B2 | 4/2011 | Bose et al. |
| 7,938,820 B2 | 5/2011 | Webster et al. |
| 7,988,646 B2 | 8/2011 | Taber |
| 8,021,351 B2 | 9/2011 | Boldenow et al. |
| 8,048,032 B2 | 11/2011 | Root et al. |
| 8,070,694 B2 | 12/2011 | Galdonik et al. |
| 8,084,246 B2 | 12/2011 | Hoon et al. |
| 8,142,413 B2 | 3/2012 | Root et al. |
| 8,114,032 B2 | 4/2012 | Ferry et al. |
| 8,211,023 B2 | 7/2012 | Swan et al. |
| 8,235,968 B2 | 8/2012 | Tremaglio |
| 8,292,850 B2 | 10/2012 | Root et al. |
| 8,366,735 B2 | 2/2013 | Bose et al. |
| 8,460,312 B2 | 6/2013 | Bose et al. |
| 8,609,426 B2 | 12/2013 | Silver |
| 8,663,259 B2 | 3/2014 | Levine et al. |
| 8,682,411 B2 | 3/2014 | Kassab et al. |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,932,320 B1 | 1/2015 | Janardhan et al. |
| RE45,380 E | 2/2015 | Root et al. |
| 8,974,411 B2 | 3/2015 | McKinnon |
| 8,992,506 B2 | 3/2015 | Gulachenski |
| 9,014,786 B2 | 4/2015 | Carmeli et al. |
| 9,023,070 B2 | 5/2015 | Levine et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,370,639 B2 | 6/2016 | Plassman et al. |
| 9,375,223 B2 | 6/2016 | Wallace |

(56) References Cited

U.S. PATENT DOCUMENTS

| | | | |
|---|---|---|---|
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,439,791 B2 | 9/2016 | Vong et al. |
| 9,451,884 B2 | 9/2016 | Palovich |
| 9,451,963 B2 | 9/2016 | Cruise et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,770,251 B2 | 9/2017 | Bowman et al. |
| 9,775,730 B1 | 10/2017 | Walzman |
| 9,789,242 B2 | 10/2017 | Criado et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,441,745 B2 | 10/2019 | Yang et al. |
| 2001/0031981 A1* | 10/2001 | Evans ............... A61B 17/221 606/200 |
| 2002/0016565 A1 | 2/2002 | Zadno-Azizi et al. |
| 2002/0026145 A1 | 2/2002 | Bagaoisan et al. |
| 2002/0156460 A1 | 10/2002 | Ye |
| 2002/0177899 A1 | 11/2002 | Eum et al. |
| 2003/0088266 A1* | 5/2003 | Bowlin ............... A61F 2/01 606/200 |
| 2003/0135193 A1 | 7/2003 | Hilgers et al. |
| 2003/0135198 A1 | 7/2003 | Berhow et al. |
| 2003/0195546 A1 | 10/2003 | Solar et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1* | 10/2004 | Kellett ............... A61B 17/221 606/200 |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0059957 A1 | 3/2005 | Campbell |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0262350 A1 | 10/2008 | Unger |
| 2008/0312639 A1 | 12/2008 | Weber |
| 2009/0030400 A1 | 1/2009 | Bose et al. |
| 2009/0043330 A1* | 2/2009 | To ............... A61F 2/07 606/194 |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0312699 A1 | 12/2009 | Pudelko |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009375 A1 | 1/2011 | Grandfield et al. |
| 2011/0054504 A1* | 3/2011 | Porter ............... A61B 17/221 606/159 |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0230859 A1 | 9/2011 | Galdonik et al. |
| 2012/0040858 A1 | 2/2012 | Ford et al. |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0035628 A1 | 2/2013 | Garrison et al. |
| 2013/0046285 A1 | 2/2013 | Griffin et al. |
| 2013/0046374 A1* | 2/2013 | Jones-McMeans ........................ A61L 31/022 623/1.35 |
| 2013/0116701 A1 | 5/2013 | Wang et al. |
| 2013/0131710 A1* | 5/2013 | Carmeli ............... A61B 17/0218 606/194 |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0155932 A1 | 6/2014 | Bose et al. |
| 2014/0163367 A1 | 6/2014 | Eskuri |
| 2014/0228808 A1 | 8/2014 | Webster et al. |
| 2014/0243882 A1* | 8/2014 | Ma ............... A61F 2/013 606/200 |
| 2014/0249508 A1 | 9/2014 | Wang et al. |
| 2014/0273920 A1 | 9/2014 | Smith |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0343537 A1 | 11/2014 | Eversull et al. |

(56) References Cited

U.S. PATENT DOCUMENTS

| | | |
|---|---|---|
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0173782 A1 | 6/2015 | Garrison et al. |
| 2015/0335857 A1 | 11/2015 | Ishikawa |
| 2015/0359547 A1 | 12/2015 | Vale et al. |
| 2016/0008572 A1 | 1/2016 | Di Caprio |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0238950 A1 | 8/2017 | Yang et al. |
| 2017/0238953 A1 | 8/2017 | Yang et al. |
| 2017/0246014 A1 | 8/2017 | Rapaport et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0055516 A1 | 3/2018 | Bagaoisan et al. |
| 2018/0207399 A1 | 7/2018 | Chou et al. |
| 2018/0242980 A1 | 8/2018 | Lubock |
| 2018/0242989 A1 | 8/2018 | Nita |
| 2018/0250013 A1 | 9/2018 | Wallace et al. |
| 2018/0263632 A1 | 9/2018 | Seifert et al. |
| 2018/0263642 A1 | 9/2018 | Nita |
| 2019/0336149 A1 | 11/2019 | Yang |
| 2019/0336727 A1 | 11/2019 | Yang |
| 2019/0366041 A1 | 12/2019 | Yang |

FOREIGN PATENT DOCUMENTS

| | | |
|---|---|---|
| EP | 2 069 528 | 3/2013 |
| JP | 2006-102222 | 4/2006 |
| WO | WO 95/009659 | 4/1995 |
| WO | WO 00/000100 | 1/2000 |
| WO | WO 09/132218 | 10/2009 |

OTHER PUBLICATIONS

International Search Report for International Application No. PCT/US18/12396 dated May 11, 2018.

Guidezilla Guide Extension Catheter, Boston Scientific 510k Submission, Feb. 20, 2017.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroInvent Surg 2014, 6 pp. 677-683.

Simon et al., *Hydrodynamic comparison of the Penumbra system and commonly available syringes in forced-suction thrombectomy*, J. NeuroInvent Surg 2014, 6, pp. 205-211.

Spiotta et al., Evolution of thrombectomy approaches and devices for acute stroke: a technical review, J. Neuro Intervent Surg 2015, 7, pp. 2-7.

\* cited by examiner

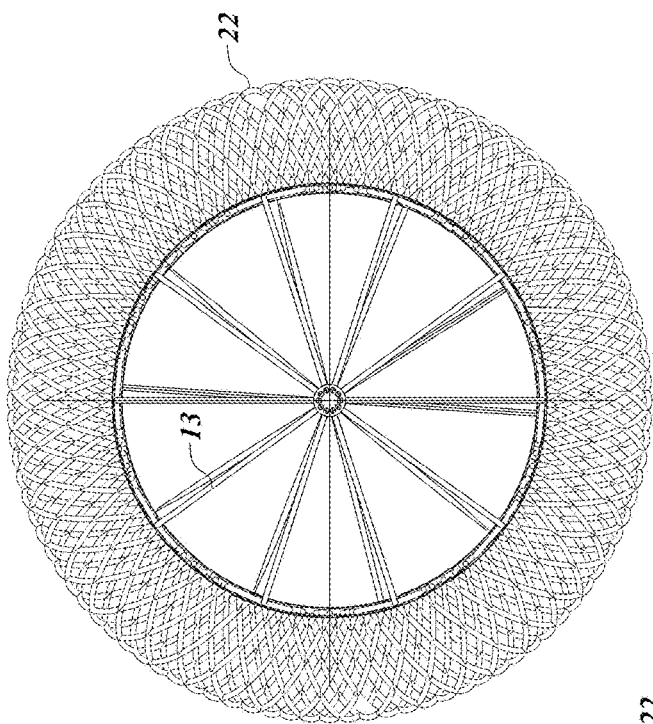
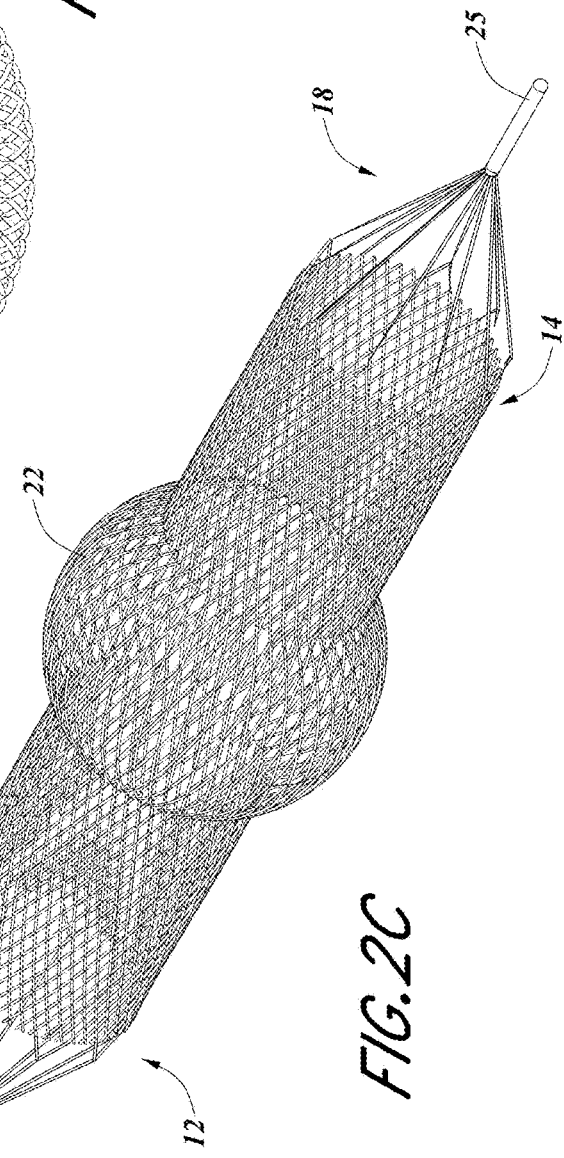
FIG.2B
FIG.2C

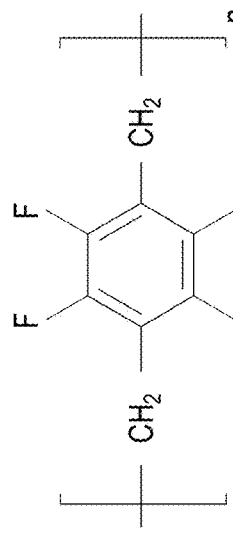
*FIG. 2Div*
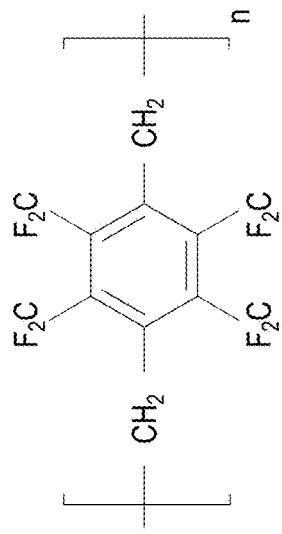
*FIG. 2Dv*
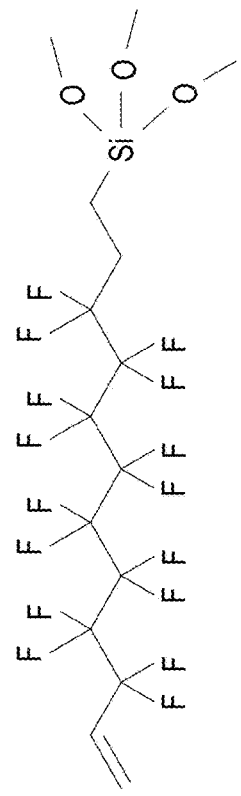
*FIG. 2Dvi*
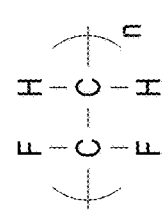
*FIG. 2Di*
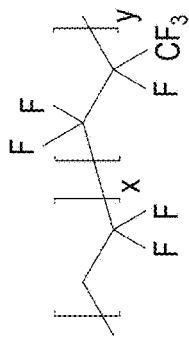
*FIG. 2Dii*
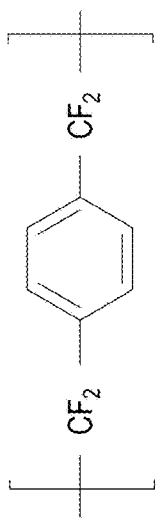
*FIG. 2Diii*

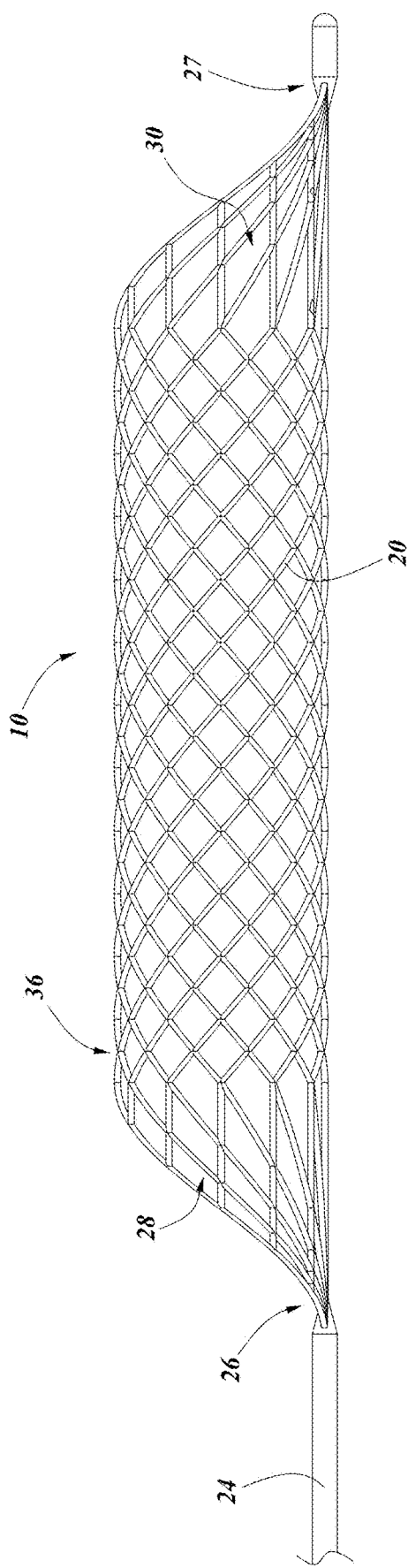
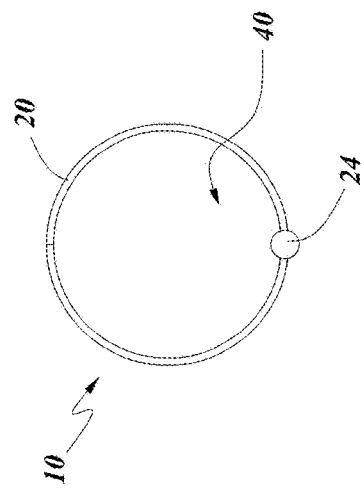

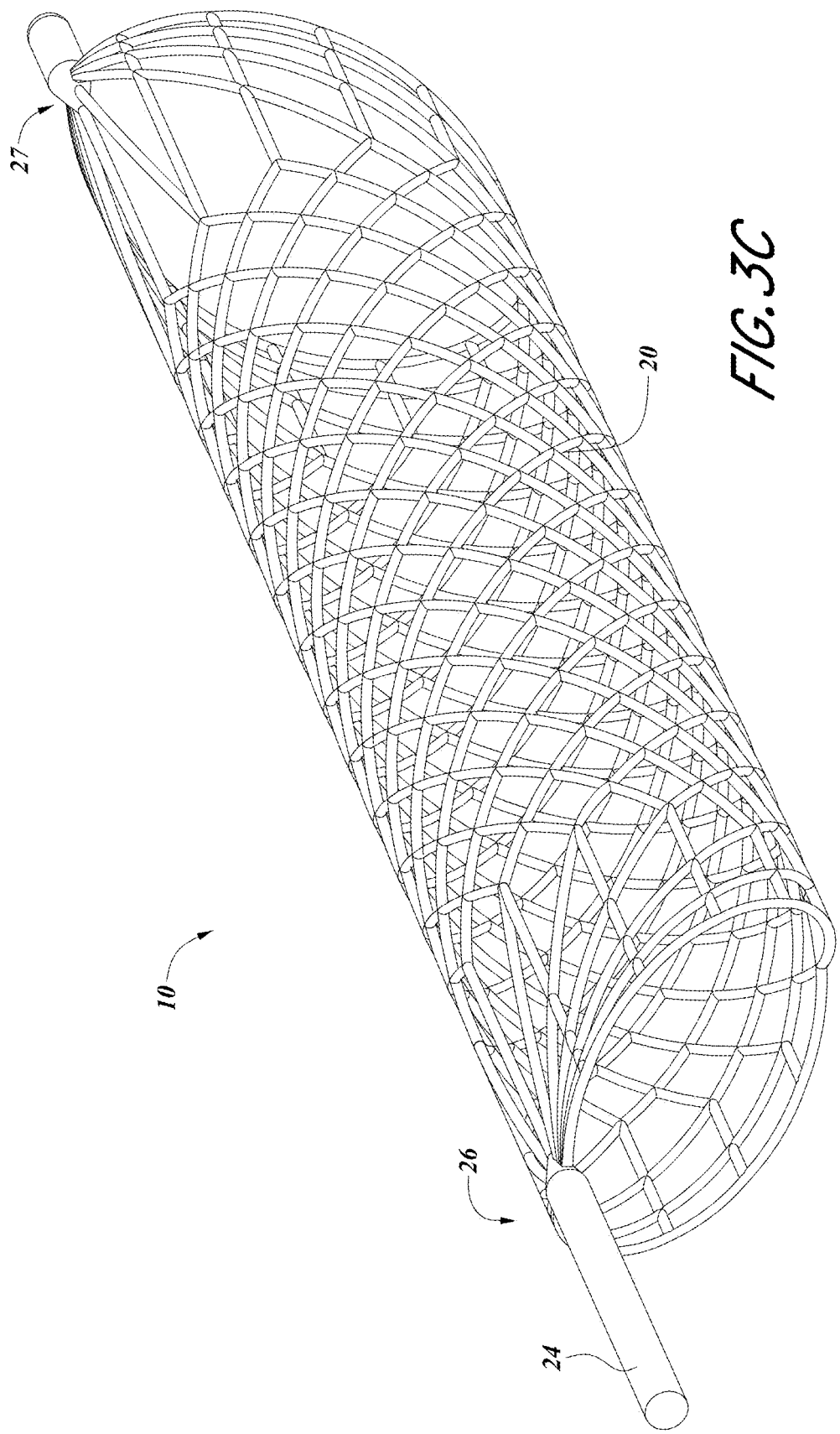

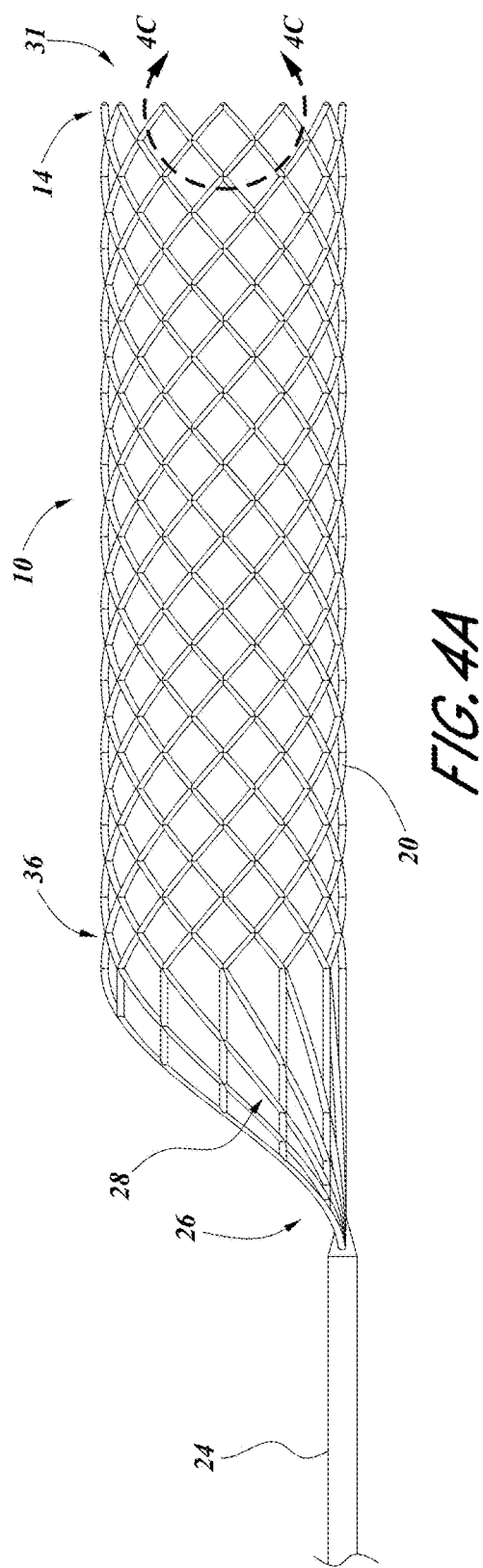
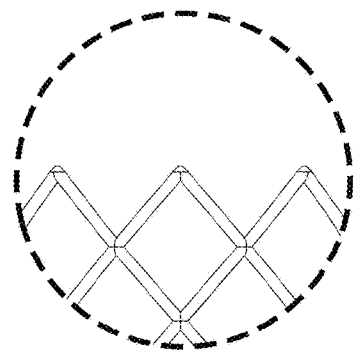
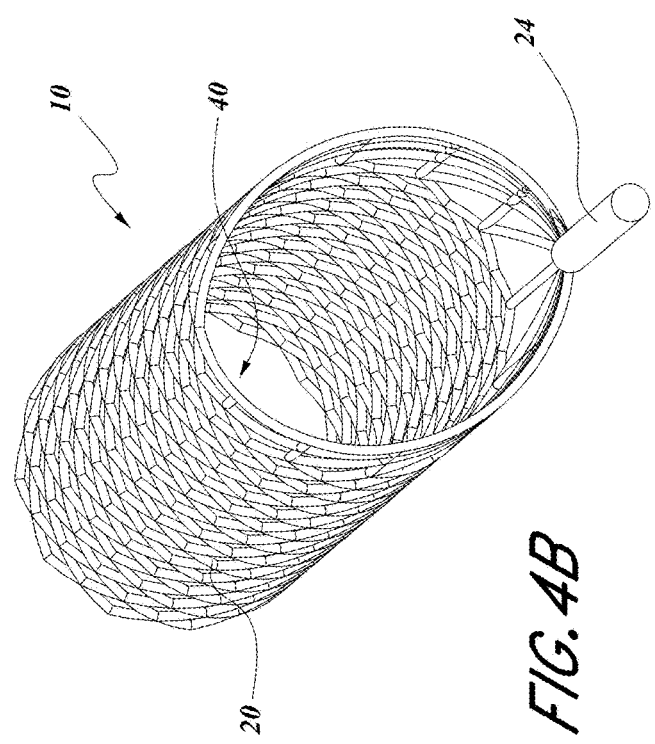

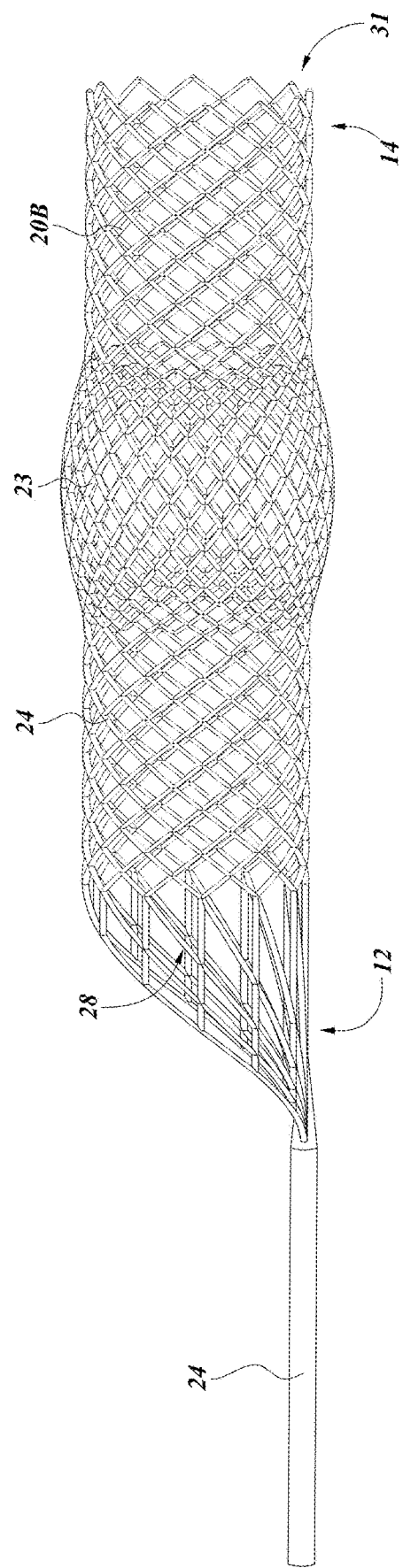
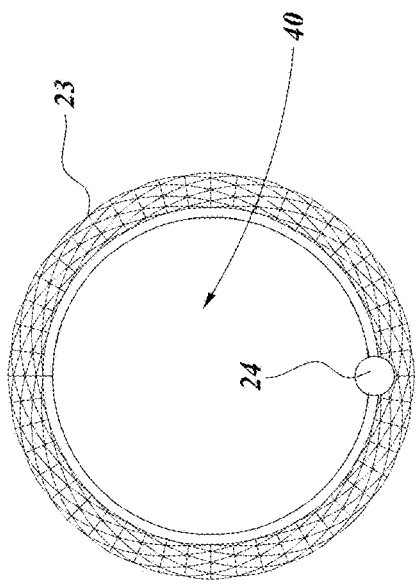
FIG.5A
FIG.5B

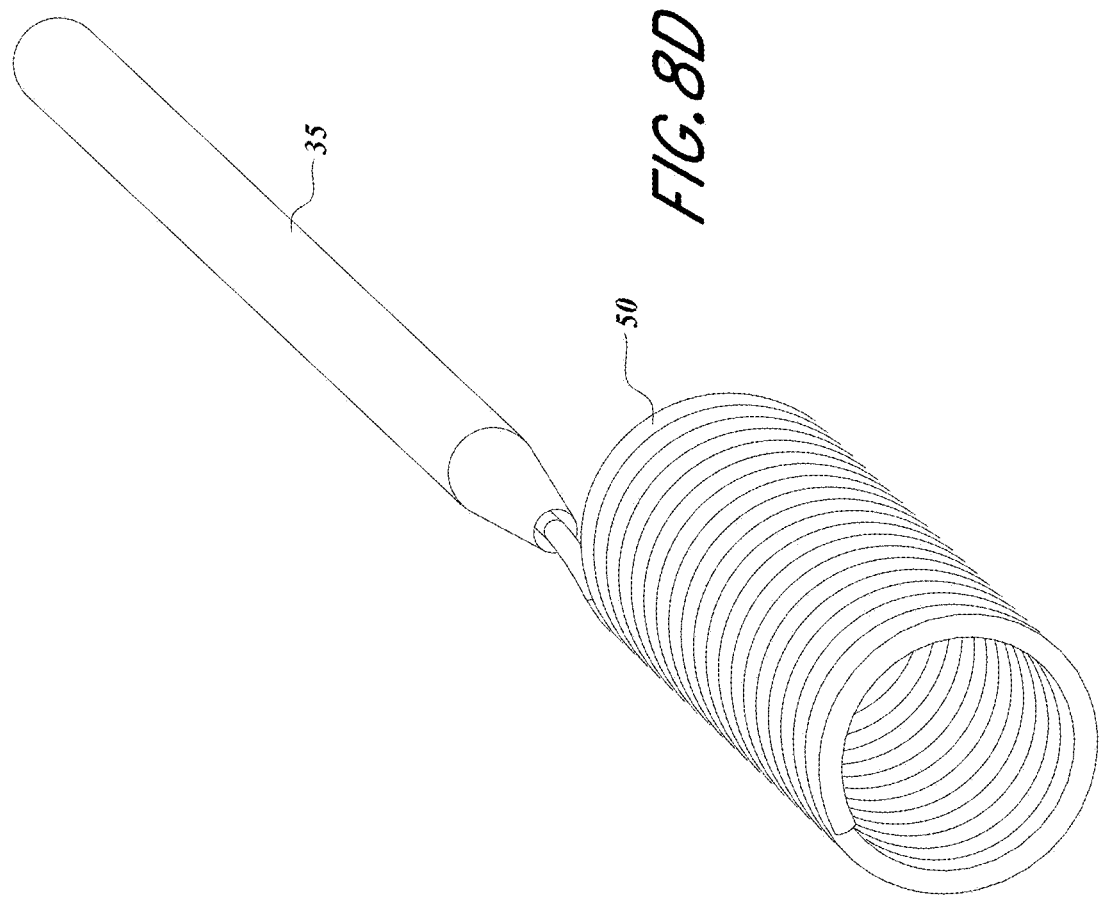

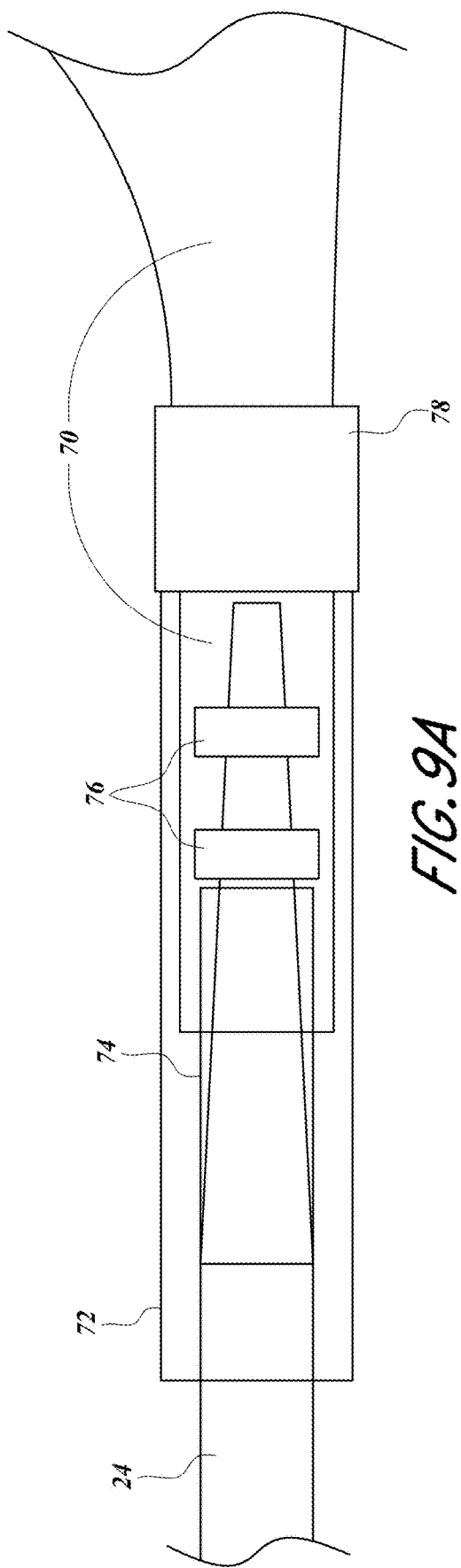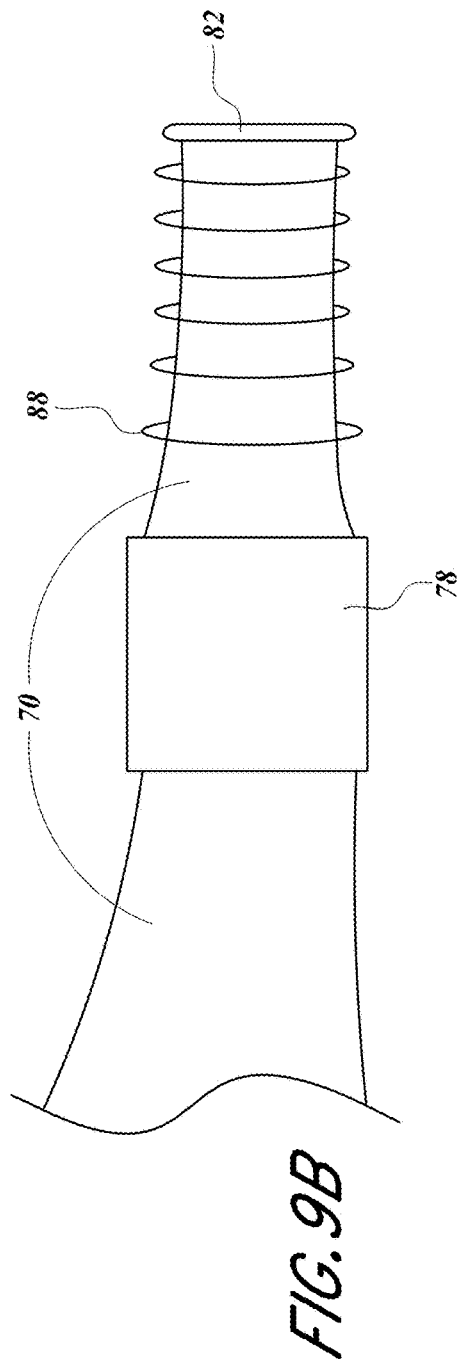

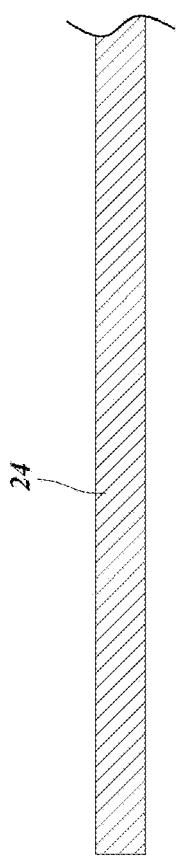
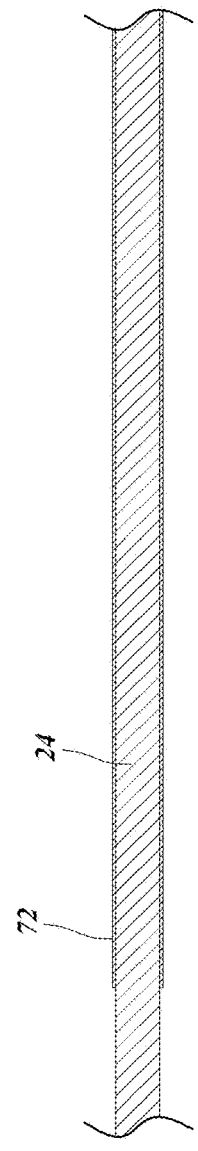
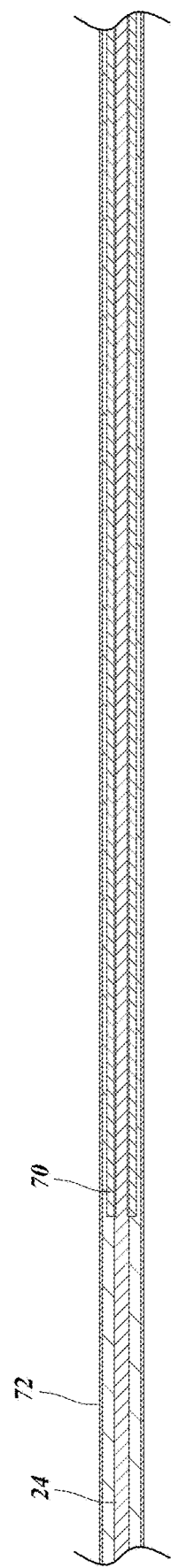

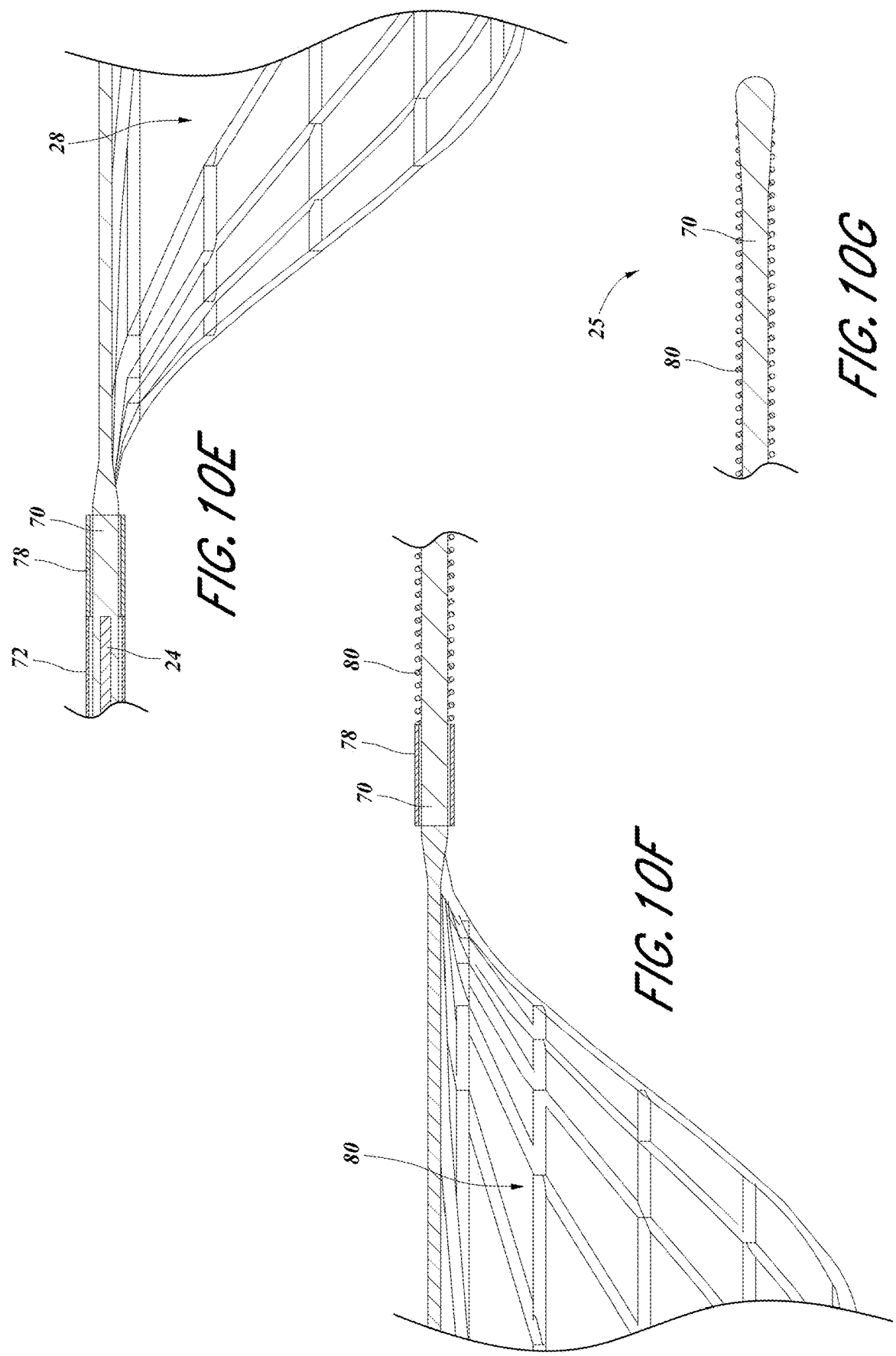

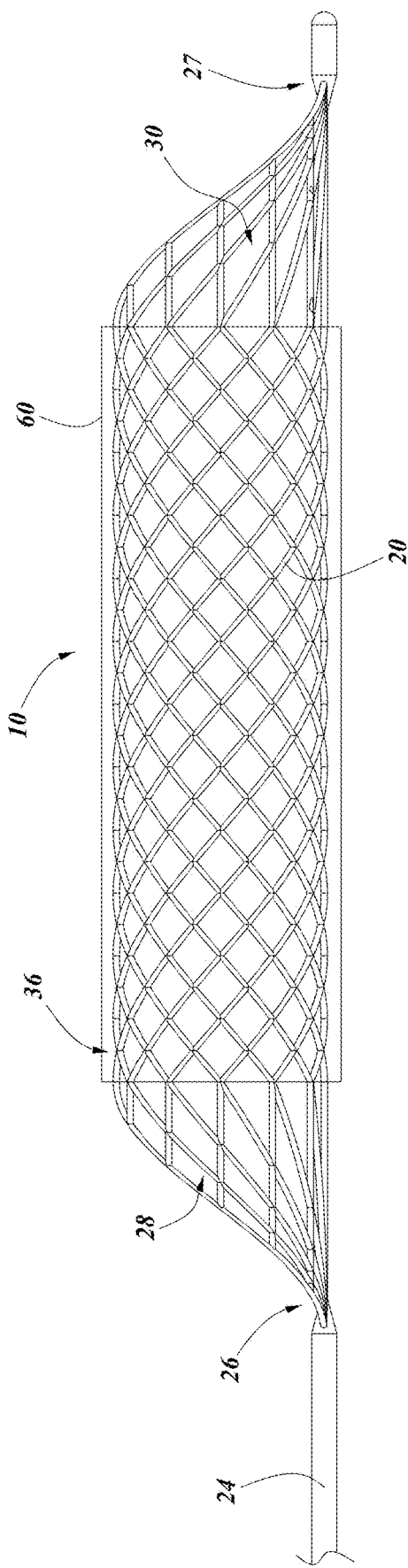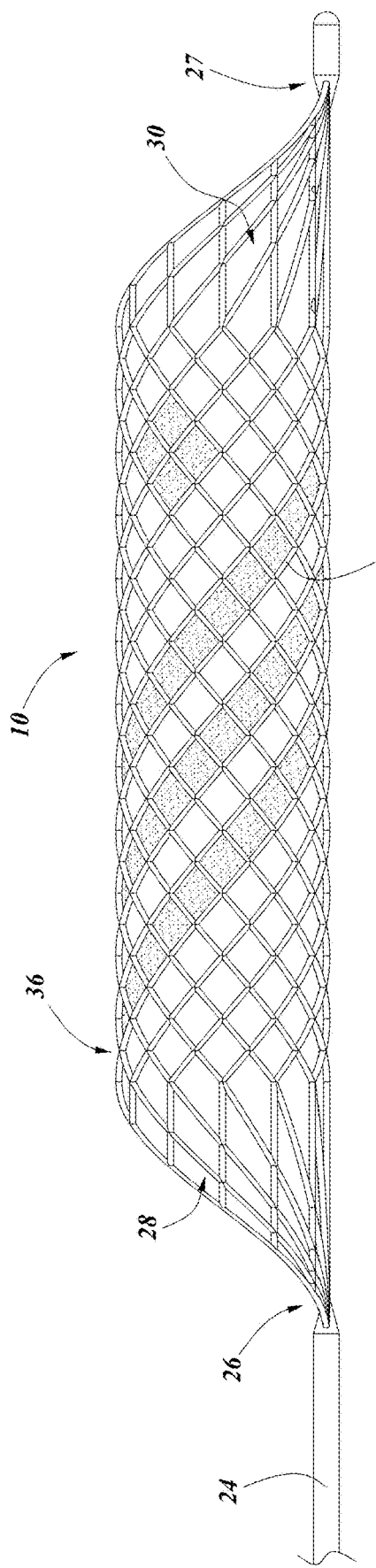

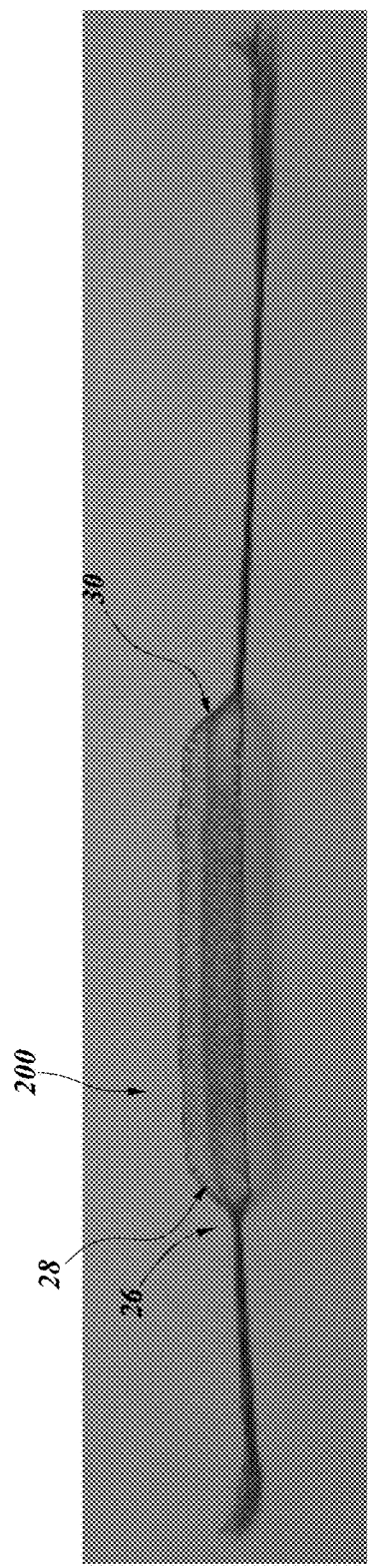
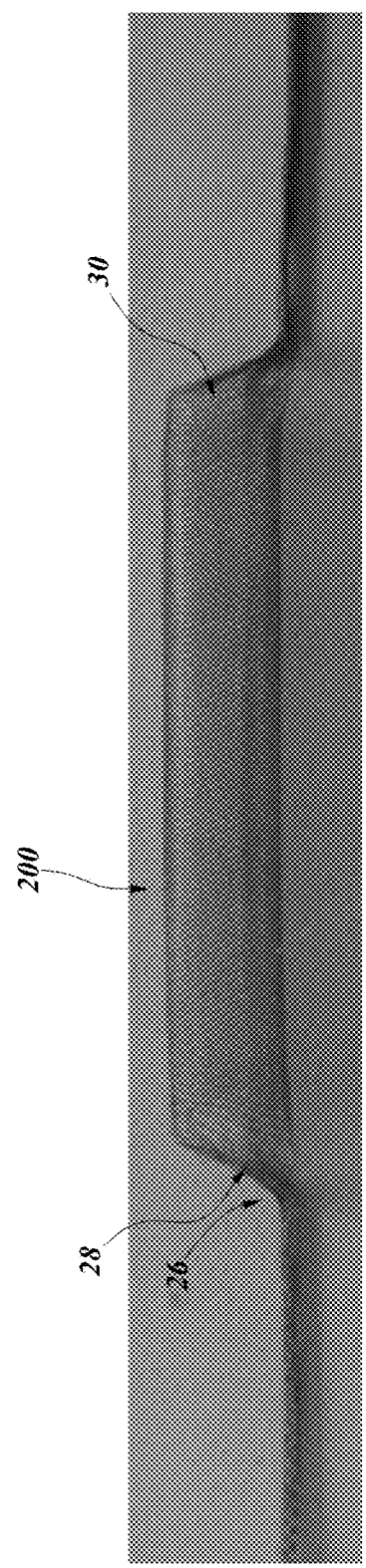
FIG. 13A
FIG. 13B

THROMBORESISTANT COATINGS FOR ANEURYSM TREATMENT DEVICES

INCORPORATION BY REFERENCE TO ANY PRIORITY APPLICATIONS

This application claims priority to U.S. Provisional Application 62/443,552, filed on Jan. 6, 2017, the entirety of which is hereby incorporated by reference herein for all purposes. Any and all applications for which a foreign or domestic priority claim is identified in the Application Data Sheet as filed with the present application are hereby incorporated by reference under 37 CFR 1.57.

BACKGROUND OF THE INVENTION

The mammalian circulatory system is comprised of a heart, which acts as a pump, and a system of blood vessels which transport the blood to various points in the body. Due to the force exerted by the flowing blood on the blood vessels, they may develop a variety of vascular defects. One common vascular defect known as an aneurysm is formed as a result of the weakening of the wall of a blood vessel and subsequent ballooning and expansion of the vessel wall. If an aneurysm is left without treatment, the blood vessel wall gradually becomes thinner and damaged, and, at some point, may be ruptured due to a continuous pressure of blood flow. Neurovascular or cerebral aneurysms affect about 5% of the population. In particular, a ruptured cerebral aneurysm leads to a cerebral hemorrhage, thereby resulting in a more serious life-threatening consequence than any other aneurysm, as cranial hemorrhaging could result in death.

Cerebral aneurysms may be treated by highly invasive techniques which involve a surgeon accessing the aneurysm through the cranium and possibly the brain to place a ligation clip around the neck of the aneurysm to prevent blood from flowing into the aneurysm.

A less invasive therapeutic procedure involves the delivery of embolization materials or devices into an aneurysm. The delivery of such embolization devices or materials may be used to promote hemostasis or fill an aneurysm cavity entirely. Embolization devices may be placed within the vasculature of the human body, typically via a microcatheter, either to block the flow of blood through a vessel with an aneurysm through the formation of an embolus or to form such an embolus within an aneurysm stemming from the vessel. A variety of deviceable coil embolization devices are known. Coils are generally constructed of a wire, usually made of a metal (e.g. platinum) or metal alloy that is wound into a helix. The coils of such devices may themselves be formed into a secondary coil shape, or any of a variety of more complex secondary shapes. Coils are commonly used to treat cerebral aneurysms but suffer from several limitations including poor packing density, compaction due to hydrodynamic pressure from blood flow, poor stability in wide-necked aneurysms and complexity and difficulty in the deployment thereof as most aneurysm treatments with this approach require the deployment of multiple coils.

Coils are usually delivered through a microcatheter, inserted through the groin for instance, as seen in FIGS. 1A and 1B. They are often inserted into the aneurysm via a pusher mechanism that relies on electrolytic erosion or a mechanical mechanism to detach the coil from the pusher. The microcatheter commonly tracks a guide wire to a point just proximal of or within the desired site for occlusion. The coil is advanced through the microcatheter and out the distal end so to at least partially fill the selected space and create an occlusion as seen in FIG. 1C. Once a coil is deployed at a desired site, occlusion results either from the space-filling mechanism inherent in the coil itself, or from a biological response to the coil such as a thrombus formation, or both. The space-filling mechanism of the coil may be either based upon a predetermined secondary geometry, or may be based upon random flow characteristics of the coil as it is expelled from a delivery sheath lumen. Coils may be inserted into the microcatheter in stretched, relatively linear conformations, but expand to larger, secondary memory shapes upon exiting the microcatheter's internal lumen.

In treatment of a cerebral aneurysm using coil embolization, about 20% cases do not require additional ancillary devices. But, particularly in the case of a wide neck cerebral aneurysm with a large orifice or a cerebral aneurysm with a large neck-to-fundus ratio, it is necessary to insert a stent or aneurysm exclusion device into a parent blood vessel, as seen in FIG. 1D, to cover a neck of the cerebral aneurysm so as to prevent migration of a coil that fills the aneurysm. Stents with aneurysm neck bridging devices that significantly occlude the flow of blood into the aneurysm may be used alternatively to coils or to supplement the embolization of the aneurysm. However, stents must remain both a low enough density to collapse into a conformation deliverable through a microcatheter and flexible enough to navigate the tortuous cerebral blood vessels. Additionally, it can be difficult to rotationally position such devices to precisely cover the defect. Covered stents or stent-grafts, comprising a sleeve of polymeric material around the stent lumen could be used to occlude the aneurysm but pose the risk of inadvertently occluding small perforator vessels proximate to the aneurysm. Stents also may provide a site for thrombus formation, with the resulting risk of embolization and stroke.

SUMMARY OF THE INVENTION

There is provided in accordance with one aspect of the invention, a coating for application to vascular devices, particularly aneurysm treatment devices. The coating is designed to make the device, typically a metal device, more biocompatible by endowing it with favorable biological properties. The coating may assist the device in reducing thrombus formation and/or promoting endothelialization to restore the native endothelial cell lining to the blood vessel where the device is inserted.

In another aspect of the invention, the coating is not uniform but is applied to the device in a conformal pattern to generate designs for achieving more favorable biological outcomes. The device may comprise a lumen, wherein the internal surface of the lumen is designed primarily to reduce thrombus formation and the outer surface of the lumen is designed primarily to promote endothelialization. Additionally or alternatively, the coating may be applied as a gradient, wherein the proximal and distal ends of the device are designed primarily to reduce thrombus formation and the middle of the device is designed to promote endothelialization. The properties of the coating may be varied by altering either the processing or the composition of the coating. The coating may be fabricated from any suitable material, but in particular may comprise: plasma-deposited fluorine, plasma-deposited glyme, phosphorylcholine, diamond-like carbon (DLC) or fluorinated-DLC, polyvinylpyrrolidone and fluorinated or perfluorinated polymers as well as solvent sprayed or dipped flouropolymers such as polyvinylidene fluoride co-polymers or fluorophosphazene. Plasma-deposited processes can also include means by which the substrate material is primed by processing methods such as mechanical abrasion, chemical etching, or preliminary coatings of priming materials such as poly(p-xylylene) polymers or poly(n-butyl methacrylate). The coating may combine different materials in different ratios to modulate the biological properties of the device. In some embodiments, coatings may also fill the interstitial gaps or openings between struts (e.g., wires of the substrate mesh material). The coating may be applied via solvent dip coating. The coating may comprise elastic polymers, such as polytetrafluoroethylene, or other suitable polymers. The application of a coating covering the interstitial gaps may form a jacketed assembly, which may reduce stagnation zones of blood flow through the inner lumen.

In another aspect of the invention, there is provided an intra vascular coil retention device for treating aneurysms. The retainer may be formed of braided wires in a pattern that creates a high density region near the middle of the device for interfacing with the aneurysm to hold embolization coils in place and enable higher packing density of coils. In some embodiments, the retainer may comprise at least 24, or alternatively at least 48, wires braided in various patterns. The retainer may be generally cylindrical. The retainer may or may not comprise a central generally spherical section, extending beyond the diameter of the adjacent cylindrical sections, for interfacing with the aneurysm. Furthermore, the retainer may comprise low-density sections at the proximal and distal ends formed by a tapering of the wires or may comprise open-faced ends. If provided, the tapered sections may form cones with apexes aligned along the center of the lumen or may be formed with the apexes circumferentially aligned along the circumference of the lumen or positioned radially outside the circumference of the lumen. The wires may be formed of any suitable material, but in particular may comprise: nitinol, DFT®, platinum, cobalt chromium, spring-tempered stainless steel, or shape-memory polymers. In one implementation, the wires may be formed from polymeric materials such as fluoropolymers (e.g., polytetrafluoroethylene (PTFE)), polyethylenes, polyurethanes, and/or polyether block amide (e.g., Pebax). In one implementation, the retainer may be releasably connected to a push wire, which may attach to the proximal apex if provided. The retainer may be controllably detached from the push wire and become a permanent implant. The retainer is designed to be delivered by a microcatheter and may be self-expanding upon retraction of the microcatheter's outer sheath. The retainer may serve as a permanent coil retention implant.

Disclosed herein is a device for insertion into a blood vessel lumen for treatment of aneurysms. The device comprises a generally cylindrical meshed section and a proximal tapered section. The generally cylindrical meshed section comprises a plurality of struts forming interstitial gaps between the struts and having a proximal face and a distal face. The generally meshed section defines a device lumen extending along an axial direction from the proximal face to the distal face. The lumen is configured to allow blood flow through the device. The proximal tapered section comprises a plurality of struts extending from a circumference of the proximal face to a proximal apex. The proximal apex is radially aligned with the circumference of the proximal face or positioned radially outside the circumference of the proximal face. The plurality of struts of the proximal tapered section extend from different points on the circumference of the proximal face in an axial and circumferential direction to the proximal apex, such that none of the plurality of struts cross through a cross-sectional area defined by the device lumen.

The plurality of struts of the generally cylindrical meshed section may be formed from braided wires. The plurality of struts of the proximal tapered section may be formed from the braided wires of the generally cylindrical meshed section. The braided wires may be at least partially braided within the proximal tapered section. One or more of the plurality of struts may be inverted within the proximal tapered section such that one or more of the inverted struts bend radially outward and toward the proximal apex within the proximal tapered section and such that the proximal apex is positioned radially outside the circumference of the proximal face. The plurality of struts may form an edge extending from or near the proximal apex and extending to the circumference of the proximal face. The edge may be configured to interface incoming blood flow. The edge can define a take-off angle relative to a longitudinal axis extending through the proximal apex parallel to the axial dimension. In some embodiments, the take-off angle is no greater than about 80 degrees or no greater than about 70 degrees. In some embodiments, the take-off angle is at least about 30 degrees or at least about 40 degrees. The device may occupy a fraction of a cross-sectional area defined by an outer diameter of the proximal face. In some embodiments, the fraction may be no greater than about 0.2, 0.1, 0.05, or 0.01. In some embodiments, the plurality of struts of the proximal tapered section and the generally cylindrical mesh section have a diameter of no greater than about 0.01 inches or 0.005 inches.

The generally cylindrical mesh section may comprise a middle section configured to be positioned adjacent the aneurysm. The middle section may comprise a substantially higher strut density than at least a portion of the remainder of the generally cylindrical mesh section. The middle section may comprise an outer diameter that is larger than an outer diameter of the proximal face in an unconstrained configuration. The higher strut density can be a result of a smaller pitch of braided wires than in a lower-density portion of the generally cylindrical mesh section and/or a result of a different weaving pattern than a lower-density portion of the generally cylindrical mesh section. In some embodiments, the middle section may comprise interstitial gaps that are no greater than about 0.008 inches across or 0.01 inches across. The generally cylindrical mesh section may be configured to provide a radially outward counter force to compression adjacent the proximal face which is greater than a radially outward counter force to compression near the middle of the generally cylindrical mesh section.

In some embodiments, the device may further comprise a distal tapered section. The distal tapered section may comprise a plurality of struts extending from a circumference of the distal face to a distal apex. The distal apex may be radially aligned with the circumference of the distal face or positioned radially outside the circumference of the distal face. The plurality of struts of the distal tapered section may extend from different points on the circumference of the distal face in an axial and circumferential direction to the distal apex, such that none of the plurality of struts cross through a cross-sectional area defined by the device lumen. The plurality of struts from the distal tapered portion may extend through a radiopaque marker ring positioned distal to the proximal apex. The plurality of struts from the distal tapered portion may be aligned in a parallel fashion distal to the distal apex to form a distal lead segment. The device may further comprise a metallic helical coil positioned around the distal lead segment. The metallic helical coil may comprise platinum or iridium. In some embodiments, the distal face may be open and substantially perpendicular to the axial direction. The open distal face may comprise a circumferential edge formed by atraumatic bends within the plurality of struts within the generally cylindrical mesh section.

The plurality of struts within the proximal tapered section may be distributed substantially uniformly around the circumference of the proximal face. The device may further comprise a push wire collinear with the proximal apex. The plurality of struts within the proximal tapered section can be aligned in a parallel fashion proximal to the proximal apex. Proximal ends of the plurality of struts may be joined to a distal end of the push wire. The plurality of struts can be substantially uniformly distributed around a circumference of the push wire. The push wire may be permanently joined to the proximal tapered section. The push wire may be detachably joined to the proximal tapered section. The distal end of the push wire may comprise a tapered portion. The distal end of the push wire may comprise a plurality of plastic rings surrounding the push wire. The proximal ends of the plurality of struts from the proximal tapered section may surround the plastic rings. The plurality of plastic rings may be spaced along the axial direction at least about 1 cm apart from each other. The plurality of struts from the proximal tapered portion may extend through a radiopaque marker ring positioned proximal to the proximal apex.

The device may comprise a collapsed configuration and an expanded configuration. The device may have a longer axial length from the proximal apex to a distal end of the device and a smaller diameter device lumen in the collapsed configuration than in the expanded configuration. The plurality of struts of the generally cylindrical mesh section and the proximal tapered section may comprise a shape memory material. The device may be configured to assume the expanded configuration as the memorized shape.

The device may further comprise a polymeric sleeve positioned around at least a portion of the device lumen. The sleeve can applied to an inner diameter of the generally cylindrical mesh section and/or an outer diameter of the generally cylindrical mesh section. The sleeve may comprise an inner layer and an outer layer and at least a portion of the generally cylindrical section can be sandwiched between the inner layer and the outer layer. The inner layer and the outer layer can be joined together within at least some of the interstitial gaps. The sleeve may comprise apertures positioned near a proximal end of the sleeve and near a distal end of the sleeve but not within a middle section of the sleeve. The sleeve comprises a fluoroelastomer. The sleeve may comprise fluorinated ethylene propylene (FEP), polytetrafluoroethylene (PTFE), polyvinylidene fluoride (PVDF), or poly(vinylidene fluoride co-hexafluoropropylene) (PVDF-HFP). The sleeve comprises a silastic, such as polydimethylsiloxane (PDMS). The sleeve may comprises an A:B:A triblock copolymer. The A block may comprise tetrafluoroethylene (TFE), ethylene, and hexafluoropropylene (HFP) and the B block may comprising vinlidene fluoride (VDF), hexafluoropropylene (HFP), and tetrafluoroethylene (TFE). The sleeve can be impregnated with or coated with polyvinylpyrrolidone (PVP), phosphorylcholine (PC), polyethylene glycol (PEG), Serene™, PEG-ylated molecules, or fluorinated molecules to provide a thromboresistant surface.

The plurality of struts of the generally cylindrical section may be coated with a coating material. The coating material may comprise plasma-deposited fluorine, plasma-deposited glyme, phosphorylcholine, diamond-like carbon, fluorinated-diamond-like carbon, polyvinylpyrrolidone (PVP), fluorinated ethylene propylene (FEP), polytetrafluoroethylene (PTFE), polyvinylidene fluoride (PVDF), poly(vinylidene fluoride co-hexafluoropropylene) (PVDF-HFP), a fluorophasphazene, carboxybetaine, sulfobetaine, methacrylated caroboxybetaine, methacrylated sulfobetaine, a fluorosilane, heparin or heparin-like molecules; hirudin; curcumin; thrombomodulin; prostacyclin; DMP 728 platelet GPIIb/IIIa antagonist; chitosan, sulfated chitosan; hyaluronic acid; tantalum-doped titanium oxide; an oxynitride, an oxide layer, or silicon carbide. The device may comprise a primer layer of poly n-butyl methacrylate (PBMA) or a poly(p-xylylene) polymer between the plurality of struts and the coating material. The coating material may entirely cover at least some of the interstitial gaps. The coating material may cover a portion of the interstitial gaps configured to be placed adjacent to the aneurysm, such that the portion covers a neck of the aneurysm. The coating material may cover alternating rows of interstitial gaps.

The device lumen can comprise an internal surface with an internal diameter and an outer surface with an outer diameter. The coating may comprises a first coating applied to the inner surface and a second coating applied to the outer surface. The first and second coatings can have distinct biological properties. The first coating can be designed primarily to reduce thrombus formation and the second coating can be designed primarily to promote endothelialization. The coating can form a gradient in at least one biological property along a length of the device in a direction aligned with the device lumen. The gradient can extend from at least the proximal face toward the middle of the generally cylindrical mesh section and then reverse from the middle of the generally cylindrical mesh section toward the distal face. The at least one biological property may be the promotion of endothelialization. Endothelialization can be promoted more toward the middle of the generally cylindrical mesh section than near the proximal and distal faces. The at least one biological property may be reduction of thrombus formation. Thrombus formation may be reduced more toward the proximal and distal faces than at the middle of the generally cylindrical mesh section. The at least one biological property may comprise reduction of thrombus formation and promotion of endothelialization. The reduction of thrombus formation may increase as promotion of endothelialization decreases. The gradient may be formed by applying the coating to the surface of the device according to processing conditions that vary along the length of the device. The gradient may be formed by varying the composition of the coating along the length of the device.

In some embodiments, the device may include at least 24 wires or 48 wires. The plurality of struts of the generally cylindrical section may comprise nitinol, DFT®, platinum, cobalt chromium, stainless steel, a fluoropolymer, polyethylene, polyurethane, polyether block amide, or a shape-memory polymer. The plurality of struts of the generally cylindrical section may be coated with polytetrafluoroethylene (PTFE), polyvinylidene fluoride (PVDF), polyvinylidene-hexafluoropropylene (PVDF-HFP), perfluoropropylene, octafluoropropane, Parylene HT, Parylene AF-4, Parylene F, Parylene VT-4; 1H,1H,2H,2H-perfluorododecyltrichlorosilane, (tridecafluoro-1,1,2,2, tetrahydrooctyle) silane, hexadecafluordodec-11-en-1-yl trimethoxysilane, or a poly(p-xylylene) polymer. The proximal apex of the device may be positioned radially outside the circumference of the proximal face.

Disclosed herein is a device for insertion into a blood vessel lumen for treatment of aneurysms, comprising a proximal end and a distal end, a device surface and a coating applied to the device surface. The distal end is to be positioned further down the blood vessel lumen than the proximal end. The coating is designed to reduce thrombus formation on the device surface and promote endothelialization of the device surface.

The device may form a lumen aligned with the blood vessel lumen. The lumen may comprise an internal surface with an internal diameter and an outer surface with an outer diameter. The coating may comprise a first coating applied to the inner surface and a second coating applied to the outer surface. The first and second coatings may have distinct biological properties. The first coating may be designed primarily to reduce thrombus formation and the second coating may be designed primarily to promote endothelialization. The coating may form a gradient in at least one biological property along a length of the device aligned with the lumen. The gradient may extend from the proximal end toward the middle of the device and then reverse from the middle of the device toward the distal end. The at least one biological property may be the promotion of endothelialization. Endothelialization may be promoted more toward the middle of the device than at the proximal and distal ends. The at least one biological property may be the reduction of thrombus formation. Thrombus formation may be reduced more toward the proximal and distal ends than at the middle of the device. The at least one biological property may comprise reduction of thrombus formation and promotion of endothelialization. The reduction of thrombus formation may increase as promotion of endothelialization decreases. The gradient may be formed by applying the coating to the surface of the device according to processing conditions that vary along the length of the device. The gradient may be formed by varying the composition of the coating along the length of the device.

In some embodiments, the coating may comprise at least one material or at least two materials selected from the group consisting of: plasma-deposited fluorine, plasma-deposited glyme, phosphorylcholine, diamond-like carbon, fluorinated-diamond-like carbon, polyvinylpyrrolidone (PVP), fluorinated ethylene propylene (FEP), polytetrafluoroethylene (PTFE), polyvinylidene fluoride (PVDF), poly(vinylidene fluoride co-hexafluoropropylene) (PVDF-HFP), a fluorophasphazene, carboxybetaine, sulfobetaine, methacrylated caroboxybetaine, methacrylated sulfobetaine, a fluorosilane, heparin or heparin-like molecules; hirudin; curcumin; thrombomodulin; prostacyclin; DMP 728 platelet GPIIb/IIIa antagonist; chitosan; sulfated chitosan; hyaluronic acid; tantalum-doped titanium oxide; an oxynitride, an oxide layer, and silicon carbide.

Disclosed herein is a device for insertion into the lumen of a blood vessel for treatment of aneurysms. The device comprises a generally cylindrical section having a lumen configured to be aligned with the blood vessel lumen and a proximal end and a distal end positioned at opposite ends of the lumen. The device is formed of braided wires.

The braided wires may comprise at least 24 wires or at least 48 wires. The braided wires can be weaved to form a high-density portion of the device toward the middle of the device for interfacing with the aneurysm. The high-density portion of the device may possess gaps between the wires that, in some embodiments, are no greater than about 0.008 inches across or about 0.01 inches across. The wires may be positioned to form low-density portions of the device at the proximal end and the distal end. The low-density portions may be formed as cones with apexes aligned approximately in the center of the lumen. The low-density portions may be formed as a tapering of the wires of the cylindrical section which come together at apexes aligned along the circumference of the lumen. The apex of the proximal end may be circumferentially aligned with the apex of the distal end.

The wires may be formed from at least one material selected from the group consisting of: nitinol, DFT®, platinum, cobalt chromium, stainless steel, fluoropolymers, polyethylene, polyurethane, polyether block amides, polytetrafluoroethylene (PTFE), and shape-memory polymers. In some embodiments, the device may be at least partially coated with poly(p-xylylene) polymers, polyvinylidene fluoride (PVDF), polyvinylidene-hexafluoropropylene (PVDF-HFP), perfluoropropylene, octafluoropropane, Parylene HT, Parylene AF-4, Parylene F, Parylene VT-4; 1H,1H,2H,2H-perfluorododecyltrichlorosilane, (tridecafluoro-1,1,2,2, tetrahydrooctyle) silane; or hexadecafluorododec-11-en-1-yl trimethoxysilane.

Disclosed herein is a method of treating an aneurysm within a blood vessel. The method comprises inserting an aneurysm treatment device into the blood vessel. The device comprises a generally cylindrical meshed section and a proximal tapered section. The generally cylindrical meshed section comprises a plurality of struts forming interstitial gaps between the struts. The generally cylindrical meshed section has a proximal face and a distal face and defines a device lumen extending along an axial direction from the proximal face to the distal face. The lumen is configured to allow blood flow through the device. The proximal tapered section joins the generally cylindrical mesh section to a push wire.

The generally cylindrical meshed section may comprise a middle section having a higher strut density than a remainder of the generally cylindrical meshed section. The method may further comprise positioning the middle section adjacent the aneurysm such that the middle section substantially covers a neck of the aneurysm. The generally cylindrical meshed section may comprise a tubular sleeve along at least a portion of its length. The method may further comprise positioning the tubular sleeve adjacent the aneurysm such that the middle section substantially covers a neck of the aneurysm.

The method may comprise inserting a microcatheter into or adjacent the aneurysm and delivering a plurality of aneurysm packing coils into the aneurysm. In some embodiments, the microcatheter can be inserted between a wall of the blood vessel and the aneurysm treatment device. In some embodiments, the microcatheter can be inserted within the device lumen and through one of the interstitial gaps of the generally cylindrical meshed section. In some embodiments, the method may further comprise removing the aneurysm treatment device by proximally retracting the push wire after delivering the plurality of aneurysm packing coils. The method may comprise replacing the aneurysm treatment device with a permanent stent. In some embodiments, the method may comprise detaching at least a portion of the push wire from the remainder of the device to leave the generally cylindrical meshed section permanently positioned adjacent the aneurysm. The proximal tapered section may comprise a plurality of struts extending from a circumference of the proximal face to a proximal apex. The proximal apex may be radially aligned with the circumference of the proximal face or positioned radially outside the circumference of the proximal face. The plurality of struts of the proximal tapered section may extend from different points on the circumference of the proximal face in an axial and circumferential direction to the proximal apex, such that none of the plurality of struts cross through a cross-sectional area defined by the device lumen.

BRIEF DESCRIPTION OF THE DRAWINGS

FIG. 1A shows insertion of a microcatheter through the groin and into the neurovascular region. FIG. 1B shows insertion of the microcatheter into the aneurysm. FIG. 1C shows the deployment of coils from the microcatheter into the aneurysm. FIG. 1D shows the use of a stent to retain the coils within the aneurysm.

FIGS. 2A-2Dvi shows an embodiment of an aneurysm treatment device. FIG. 2A shows a side view. FIG. 2B shows an end view. FIG. 2C shows a perspective view. FIG. 2Di-2Dvi illustrate various chemical structures of monomers or polymers that may be used to coat the wire strands or struts of the device.

FIGS. 3A-3C show another embodiment of the aneurysm treatment device. FIG. 3A shows a side elevation view of the device. FIG. 3B shows an end view of the device. FIG. 3C shows a perspective view of the device.

FIGS. 4A-4C show another embodiment of the aneurysm treatment device. FIG. 4B shows a proximal perspective view of the device. FIG. 4C shows a view of an edge of the open configuration of the device.

FIGS. 5A-5B show another embodiment of the aneurysm treatment device. FIG. 5A shows a side view of the device. FIG. 5B shows a proximal end view of the device.

FIG. 7A shows the effect of the device fraction that occupies the blood flow cross section. FIG. 7B shows the effect of the take-off angle. FIG. 7C shows the effect of the wire porosity, wire size, and blood vessel size.

FIGS. 8A-8D depict an alternative embodiment of the device. FIG. 8A shows deployment of a coil in a linear conformation. FIGS. 8B and 8C show the progressive tightening of the coil by a tether into a coiled conformation. FIG. 8D shows another perspective view of the coil in its final coil conformation.

FIGS. 9A-9B schematically depict proximal and distal ends of the meshed or braided portion of the aneurysm treatment device. FIG. 9A depicts a proximal joint between the braided structure and the push wire. FIG. 9B depicts a distal lead segment formed from the distal end of the braided structure.

FIGS. 10A-10G schematically depicts cross-sections of various portions of an aneurysm treatment device attached to a push wire. FIGS. 10B-10G illustrate close-up views of the portions depicted in FIG. 10A.

FIGS. 11A-11E schematically depict a sleeve for application to a meshed aneurysm treatment device. FIG. 11A schematically depicts the sleeve and the meshed device. FIG. 11B depicts a close-up image of a meshed structure in an unexpanded configuration comprising a PDMS sleeve. FIG. 11C depicts a close-up image of a meshed structure in an expanded configuration comprising a PDMS sleeve. FIG. 11D depicts a close-up image of a meshed structure in an expanded configuration comprising a sleeve formed from a triblock copolymer. FIG. 11E schematically depicts various examples of selective coverage of the interstitial gaps of a meshed device using a sleeve or coating.

FIG. 12A shows use of a catheter to establish a path to the aneurysm. FIG. 12B shows use of microwires to help guide delivery catheters for both the coils and device to the aneurysm. FIG. 12C shows the placement of one catheter in the aneurysm for delivering the coils and another in the blood vessel next to the aneurysm for placing the device. FIG. 12D shows the catheters upon removal of the microwires. FIG. 12E shows the deployment of the device and a coil from the respective catheters. FIG. 12F shows the partially expanded device upon deployment and the aneurysm upon being packed with coils. FIG. 12G shows the packed aneurysm after the catheters are retracted and the coil assist device is removed. FIG. 12H alternatively shows the packed aneurysm with a permanent device implanted next to the aneurysm in the blood vessel after the catheters are retracted. FIG. 12I shows a close-up view of the deployment of the coils and the coil assist device.

FIGS. 13A-13B depict examples of a meshed aneurysm treatment device formed from braided nitinol wire. FIG. 13A shows a perspective view of a meshed device comprising inverted proximal and distal ends. FIG. 13B shows a side view of a meshed device without inverted wires at either the proximal or distal end.

DETAILED DESCRIPTION OF THE PREFERRED EMBODIMENT

Figure 1A:
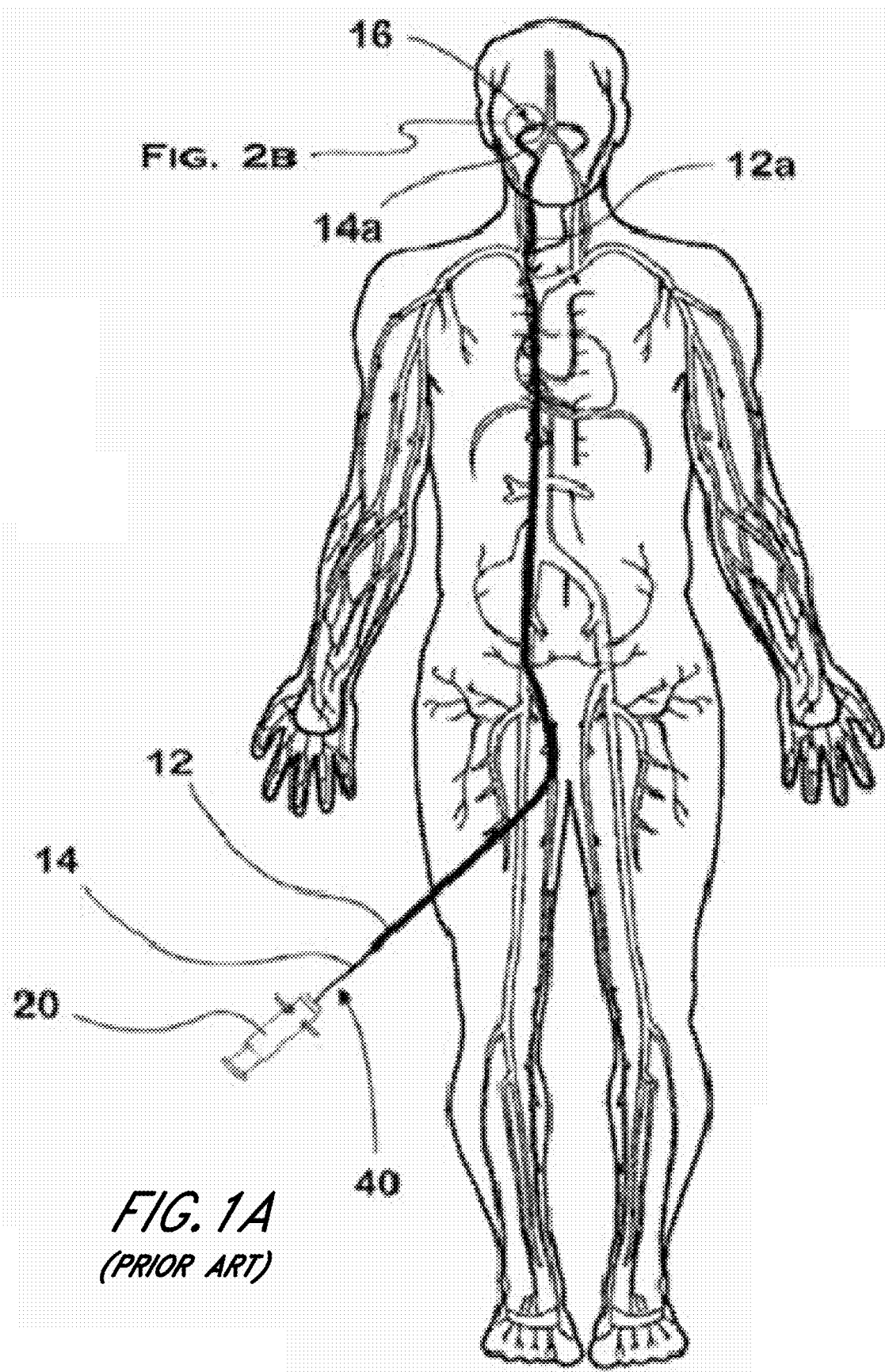
FIGS. 1A-1D shows the treatment of a neurovascular aneurysm by deployment of coils via and a microcatheter followed by deployment of a vascular stent.
Figure 1C:
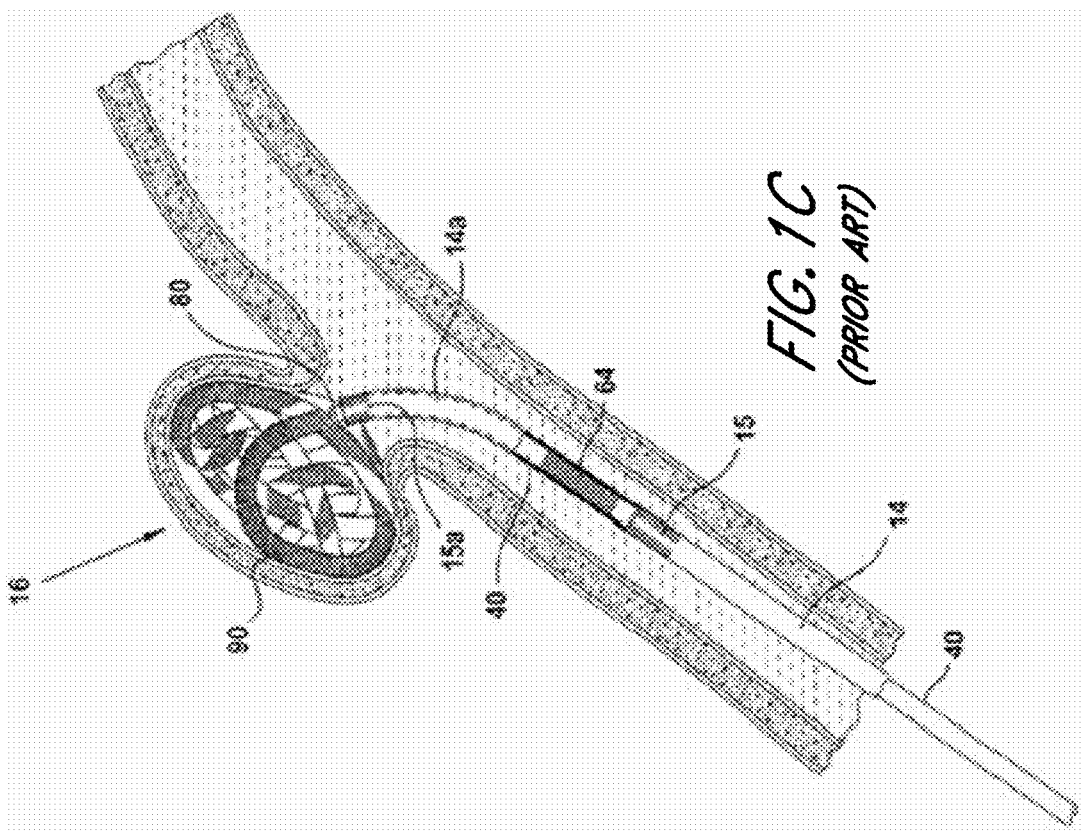
Figure 1B:
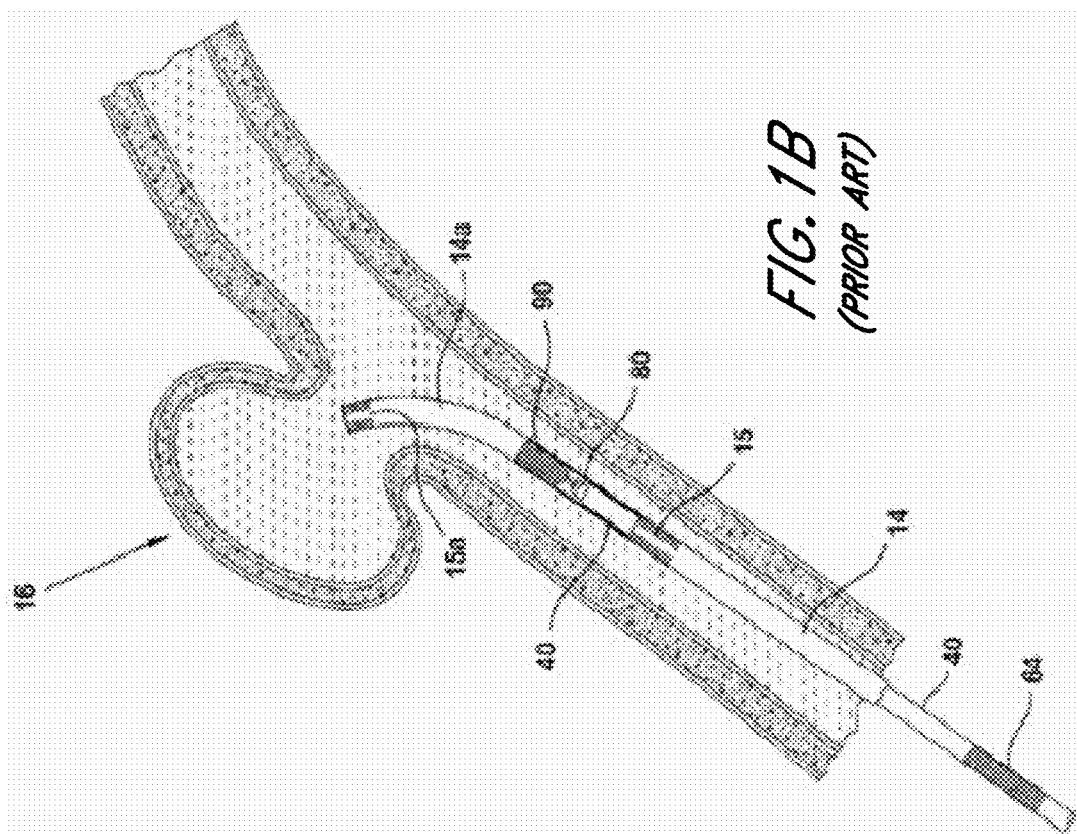
Figure 1D:
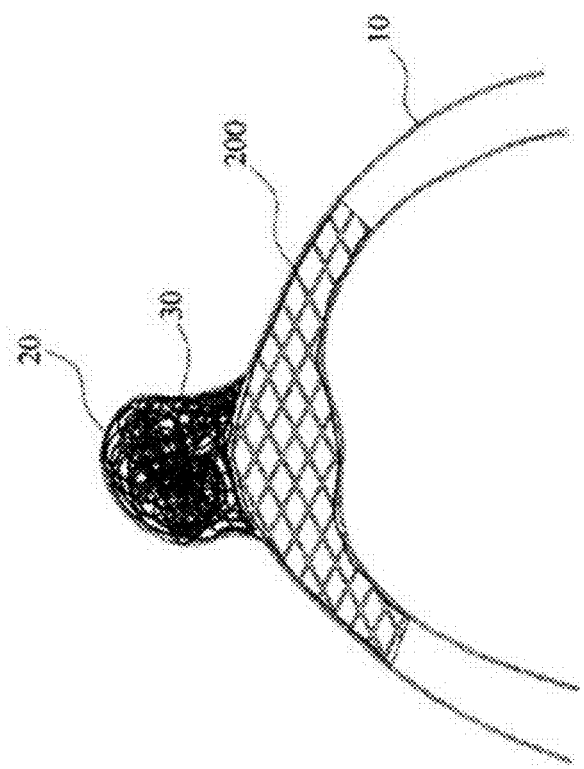

The device coating may inhibit thrombus formation (i.e. is thromboresistant) and/or promote endothelialization. Thromboresistance may be achieved, for instance, by reduction of protein adsorption, cellular adhesion, and/or activation of platelets and coagulation factors. Endothelialization may be accomplished by promoting the migration and adhesion of endothelial cells from the intimal surface of the native blood vessel wall onto the device and/or by the seeding of endothelial cells on the device prior to implantation. In preferred embodiments, the coating may be thin, robust (e.g. does not flake off with mechanical friction), and/or adheres to metallic surfaces such as nitinol, cobalt chromium, stainless steel, etc. In many embodiments, the coating properties may be achieved by selection of the coating material, processing of the coating on the device, and/or design of the coating surface.

The coating material may be selected from, derived from, partially composed of, or produced from a combination of a number of materials, including but not limited to: fluorinated or perfluorinated polymers (e.g, polyvinylidene fluoride (PVDF) or copolymers thereof, fluorophsphazenes, etc.); plasma-deposited fluorine materials; zwitterionic substances; polyvinylpyrrolidone (PVP); phosphorylcholine; sulfonated materials; glyme materials; PEG-based materials; carboxybetaine, sulfobetaine, or methacrylated versions thereof; self-assembled monolayers (e.g., fluorosilanes); heparin or heparin-like molecules; hirudin; curcumin; thrombomodulin; prostacyclin; DMP 728 (a platelet GPIIb/IIIa antagonist); chitosan or sulfated chitosan; hyaluronic acid; tantalum-doped titanium oxide; oxynitrides, oxide layers, inorganic materials such as diamond-like carbon (DLC) or fluorinated-DLC, and silicon carbide. In some embodiments, a priming layer may be provided between the device and coating. The priming layer may facilitate the attachment of the coating to the device. Additionally, the device may comprise a complete or partial luminal layer of endothelial cells or be seeded with endothelial cells prior to implantation.

The coating material(s) may be applied to the device surface according to a number of processes, depending on the composition selected. These processes may include but are not limited to: plasma vapor deposition; glow discharge deposition; chemical vapor deposition; low pressure chemical vapor deposition; physical vapor deposition (liquid or solid source); plasma-enhanced chemical vapor deposition; plasma-assisted chemical vapor deposition; thermal cracking (e.g., with fluoropolymers such as Parylene), spray coating; dip coating; spin coating; magnetron sputtering; sputter deposition; ion plating; powder coating; thermal spray coating; silanization; and/or layer-by-layer polymerization. Some processes (e.g., silanization or layer-by-layer polymerization) may be particularly useful for forming thin coatings. The application processes may be broadly categorized as vapor deposition processes or solution-based processes. In some embodiments, the vapor deposition processes may proceed according to equilibrium reactions or non-equilibrium reactions and may use stable precursors or easily vaporized active precursors. Vapor deposition processes may be particularly well-suited for fabrication of conformal coatings, in which a particular composition is applied only selectively to distinct regions of the device, especially where complex patterns or geometries are involved. Vapor depositions can be performed relatively quickly and can easily produce thin high-integrity coatings (e.g., less than 20 nm, 20-50 nm, 50-75 nm, 75-100 nm, 100-150 nm, 150-300 nm, 300-500 nm, greater than 500 nm, or a thickness from any range there between). Solution-based processes may result in highly reliable molecular architectures and can be readily amenable to sterilization without altering the molecular architecture and/or biological activity. Many of the materials may be cured subsequent to application by heat melting and/or by cross-linking.

In some embodiments, the device may be primed prior to application of a coating. Priming the device may facilitate attachment of the coating to the device (e.g., to the struts or wires of the device). Priming of the surface may be by mechanical means, such as media blasting, sanding, scribing, etc. Mechanical priming may increase the surface area of the device. Increasing the surface area may promote adhesion of coating molecules and/or cells (e.g., endothelial cells). Priming of the surface may be by chemical means such as etching, or other surface functionalization, such as bombardments with hydrogen or nitrogen ions to activate molecular bonding sites, or pre-coatings with substrates that help with adherence of the final polymer coating. In some embodiments, multiple layers of a coating or multiple coatings may be applied to the device. Priming may be performed on the underlying device and/or on one or more coatings of the device.

In some embodiments, the coating consists primarily of plasma-deposited fluorine to form a hydrophobic surface. The fluorine may be derived from fluorocarbon gases (plasma fluorination), such as perfluoropropylene ($C_3F_6$), and the precursor molecules may be cross-linked on the device surface to form a more robust coating.

In some embodiments, the coating consists primarily of plasma-deposited glyme. Glyme refers to glycol ether solvents, which share the same repeating unit as poly(ethylene oxide) (PEO) and poly(ethylene glycol) (PEG), and therefore exhibits some of the same biological properties as materials derived from those polymers. The glyme may be derived from tetraglyme ($CH_3O(CH_2CH_2O)_4CH_3$), for example, and the precursor molecules may be cross-linked on the device surface to form a more robust coating.

In some embodiments, the coating consists primarily of phosphorylcholine biomaterials. Phosphorylcholine is the hydrophilic polar head group of some phospholipids, including many that form bi-layer cell membranes. Phosphorylcholine is zwitterionic, comprising a negatively charged phosphate covalently bonded to a positively charged choline group. The high polarity of the molecule is believed to confer phosphorylcholine biomaterials with a strong hydration shell that resists protein absorption and cell adhesion. Phosphorylcholine is commonly employed in coating coronary drug-eluting stents to help prevent restenosis and resist thrombosis. Polymeric phosphorylcholine biomaterials may attach both hydrophobic domains as well as phosphorylcholine groups to a polymer chain, with the hydrophobic domains serving to anchor the polymer chains to the surface to be coated and the phosphorylcholine groups orienting themselves toward the aqueous biological environment. Phosphorylcholine biomaterials may be used to coat metals, including stainless steel, nitinol, titanium, gold, and platinum; plastics, including polyolefins, polyvinyl chloride (PVC), poly(methyl methacrylate) (PMMA), polyethylene terephthalate (PET), polyurethane (PU), polycarbonate, polyamides, polyimides, polystyrene, and polytetrafluoroethylene (PTFE); rubbers, including silicone, latex, and polyisobutylene (PIB); glasses; ceramics; and biological tissues such as tooth enamel. Phosphorylcholine-conjugated polymers may also be used to form bulk biomaterials, in which the polymeric backbone is cross-linked.

In some embodiments, the polymer backbone may be a methacrylate polymer which incorporates phosphorylcholine. In many embodiments, phosphoryl choline groups will comprise at least 1%, 5%, 10%, 15%, 20%, 25%, or more than 25% of the functional groups attached to the polymer backbone. These polymers may be produced synthetically, such that the molecular structure may be precisely controlled, but may still closely mimic naturally occurring biomolecules. Various monomers may be included in phosphorylcholine polymers which alter its precise chemical properties and may be useful for tailoring phosphorylcholine biomaterials for drug delivery by affecting the material's interaction with drug payloads. Water content, hardness, and/or elasticity can be easily modulated with phosphorylcholine biomaterials. Phosphorylcholine biomaterials coatings may be applied to surfaces through reliable and highly reproducible solution-based techniques and are relatively simple to sterilize. Suitable compositions of phosphorylcholine may include Vertellus' PC 1036 and/or PC 1059.

In some embodiments, the coating comprises primarily fluorinated or perfluorinated polymers applied via solution-based processing. Like the plasma-deposited fluorine surface, the fluorinated or perfluorinated polymers result in a hydrophobic surface. To facilitate attachment, a primer such as poly n-butyl methacrylate (PBMA), which may preferably be between about 264 and 376 kDa, may be first applied to the device. An appropriate polymer precursor may be poly(vinylidene fluoride co-hexafluoropropylene) (PVDF-HFP) and may preferably comprise molecular weights between about 254 and 293 kDa. The PVDF-HFP may be applied via a solvent with a low surface tension to facilitate spreading and preferably a solvent that evaporates quickly. The polymer solution may be applied by dip coating or a spin or drying technique. Applying heat drying or forced air to the freshly coated device may reduce webbing. The fluorinated or perfluorinated polymers may be cross-linked on the device surface to produce a more robust coating. Other suitable fluoropolymers may include polyvinylidene fluoride (PVDF) and/or fluorophosphazenes.

The coating is preferably thin to reduce the risk of debris creating dangerous emboli, especially in neurovascular applications. For the same reason, the coating is preferably durable and not prone to produce debris upon friction created when the device is expanded (e.g., when the struts rub against each other). In some embodiments, the coating is no greater than about 300 nm thick. Coating materials that are mechanically robust and do not flake or fracture after coating may be particularly suitable for thicker coatings (e.g., 300 nm thick coatings). In some embodiments, the coating is no greater than about 3 nm, 5 nm, 10 nm, 15 nm, 20 nm, 25 nm, 30 nm, 40 nm, 50 nm, 60 nm, 75 nm, 100 nm, 150 nm, 200 nm, or 300 nm thick. In some embodiments, coatings may be greater than 300 nm thick or less than 3 nm (e.g., Angstrom levels). Thinner coatings (e.g., 75 nm thick or less) may provide robust performance in endothelialization and/or anti-thrombogenicity while minimizing the coating's mechanical contribution to the flow characteristics through the central lumen of the device. Thinner coatings may be less likely to produce particulate debris of larger sizes that could pose risks of embolization, such as stroke. In preferred embodiments, the coating may be between about 25-50 nm thick, 30-50 nm thick, 30-40 nm thick, 40-50 nm thick, 35-40 nm thick, 40-60 nm thick, 50-60 nm thick, less than 25 nm thick, or greater than 60 nm thick. Coatings within optimal ranges may provide sufficient surface coverage and reduced thrombogenicity while minimizing potential toxicity concerns. For example, in some embodiments, even if all the coating were stripped from the device, the amount of coating material in the thin coating would be below a toxicity threshold. The coating coverage and thickness may be determined by scanning electron microscope (SEM). In some embodiments, 100% surface coverage is achieved. In some embodiments, less than 100% surface coverage is achieved (e.g., 25%, 50%, 75%, 80%, 90%, less than 25%, between 90-100%, or any range there between). In some embodiments, the device may not need 100% surface coverage to achieve sufficient anti-thrombogenic properties. Durability may be evaluated by performing SEM before and after simulated fatigue. Also, in preferred embodiments, the coated device satisfies the USP 788 standard. That is, it produces no more than 600 particles that are 25 μm or larger and no more than 6000 particles that are between 10 μm and 25 μm. Furthermore, the device preferably does not generate particulate less than about 2 μm in size.

The coating or coatings may be applied differentially to different regions of the device. In some embodiments, the internal diameter of the device lumen is applied with a coating which optimizes thromboresistance while the outer diameter of the device is applied with a coating that optimizes endothelialization or vice-versa. In some embodiments, the coating is optimized to promote endothelialization toward the middle of the device (e.g., along a portion configured to be positioned proximate an aneurysm neck) and to reduce thrombosis towards the proximal and distal ends of the device. Promoting endothelialization near the aneurysm neck may facilitate growth of an intimal layer which occludes the aneurysm from the blood vessel. Various combinations of the aforementioned may also be applied. Furthermore, such a variation in properties along the length of the device may be attained as a gradient in properties rather than as distinct regions with distinct properties. The difference in properties may be accomplished by altering the composition of the coating and/or by differentially processing the coating during its application. The composition of the coating at any point may comprise one or more of the materials discussed above. In some embodiments, such conformal coating strategies may be used to promote endothelialization of the device along the aneurysm neck, such that the aneurysm eventually becomes sealed off from the native lumen of the blood vessel. In some embodiments, the device is dip coated such that the polymer coating forms as a film which fills the void or interstitial gaps or spaces between the device struts or wires. Other processes for forming a coating which extends across one or more of the interstitial spaces may be used as well. In some embodiments, the film may be selectively removed by laser after the film has been formed on the device. The film may have variable regions of porosity. For example, the film may be made (e.g., with a laser) to have a gradient of porosity along a length or a portion of the length of the device. The perforations made by the laser or other means may be positioned within the interstitial gaps of the meshed device. The perforations may be of various sizes. In some embodiments, the perforations may be about equal to the size of the interstitial gap (e.g., in a fully expanded configuration), substantially smaller than the size of the interstitial gap, or various sizes there between. In some embodiments, more than one perforation may be positioned within an interstitial gap.

The device may be a permanent or temporary intravascular scaffold, such as a deployable vascular stent or a temporary scaffold. In some embodiments, the device may be an aneurysm treatment device, such as those shown in FIGS. 2A-5B. In such embodiments, the device provides mechanical support for the coils or other embolic implant, to prevent them from falling into the blood stream and enables a higher packing density of coils. In some embodiments, the device may temporarily retain the coils or implants within the aneurysm. Once the packing density of the coils is high enough, the coils may exert sufficient pressure on each other to retain the coils within the aneurysm and prevent them from falling through the aneurysm neck and into the blood stream. In some embodiments, the device may remain implanted within the blood vessel and may facilitate retention of the coils within the aneurysm.

Figure 2A:
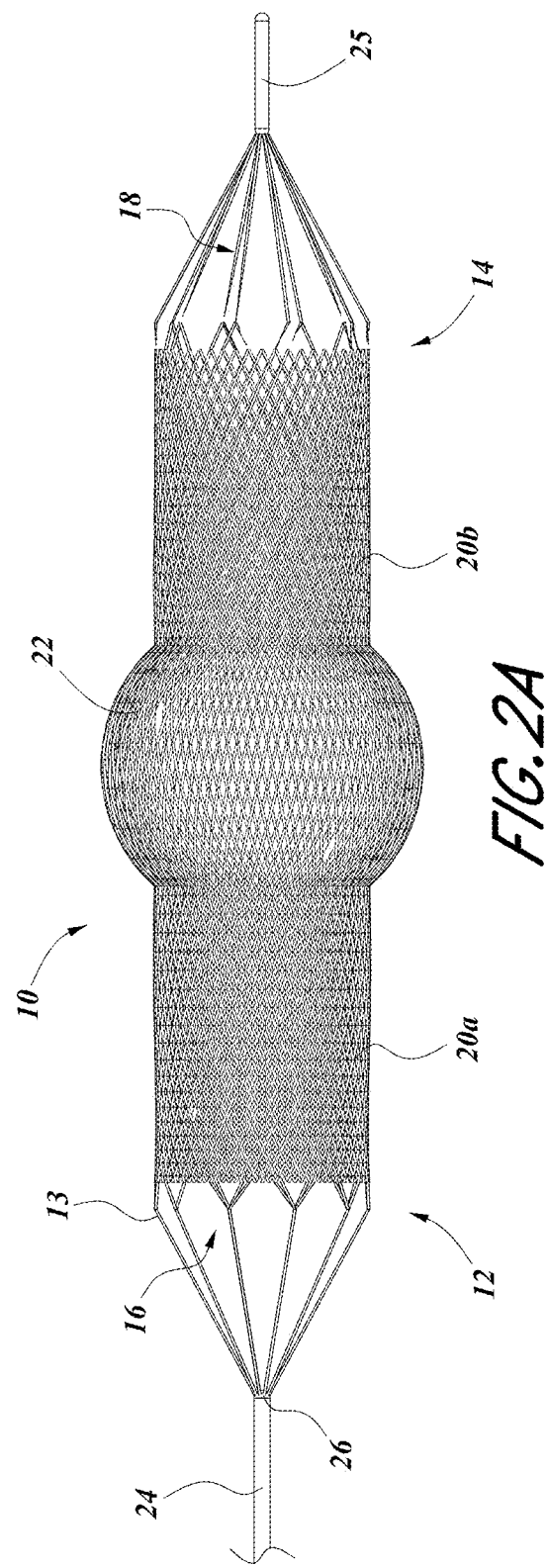

FIGS. 2A-2C schematically illustrate an example of an aneurysm treatment device 10. FIG. 2A depicts a side view of the device 10. FIG. 2B depicts a perspective view of the device 10. FIG. 2C depicts an end view of the device 10. As seen in FIGS. 2A-2C, the device 10 may comprise a proximal end 12 and a distal end 14. The proximal end 12 may be symmetric to the distal end 14. At least the proximal end 12 and optionally the distal end 14 may comprise a conical section 16, 18 connected to a central section 20. The central section 20 may be substantially cylindrical. The conical sections 16, 18 may be relatively lower density than the central section 20. The central section 20 may comprise a proximal portion 20A and a distal portion 20B.

The body of the device 10 may comprise spaced struts or wires (e.g., woven or braided wires) which are joined together or overlap to form open cells or interstitial gaps (e.g., diamond shaped cells) between the struts or wires. In some implementations, the body comprises struts or wires which extend along the axial direction of the device 10 while in a first circumferential direction (e.g., a clockwise direction) and struts or wires which extend along the axial direction while also extending in a second circumferential direction, opposite the first circumferential direction (e.g., counterclockwise). The opposing wires may join, intersect, and/or overlap at various angles (e.g., 10 degrees, 20 degrees, 45 degrees, 60 degrees, 80 degrees, 90 degrees, 100 degrees, 120 degrees, 125 degrees, 130 degrees, 135 degrees, 140 degrees, 145 degrees, 160 degrees, etc. in an expanded configuration). In some embodiments, the angle may be between about 60 degrees and about 155 degrees. In some embodiments, the angle may be between about 120 degrees and about 130 degrees. The angle between the opposing wires or struts may change as the device 10 is expanded or collapsed. In some implementations, the struts or wires may extend substantially parallel to the axial direction of the device 10, at least along a portion of the device 10. In various segments, the cells may be relatively uniform in size and shape. The size and shape of the cells may change upon expansion/collapse of the device. In some embodiments, sections of the device comprising relatively larger cell areas may be relatively low-density. In some embodiments, the conical sections 16, 18 may be as open (i.e. low-density) as possible to minimize the obstruction of blood flow and/or reduce thrombus formation. In some embodiments, the conical sections 16, 18 may comprise at least two or three or four or more struts 13 that incline radially inwardly away from the central section 20 of the implant body to form an apex, such as proximal apex 26. The struts 13 may be generally uniformly spaced around the circumference of the device 10. In embodiments comprising distal struts 13, the struts 13 at the proximal end may be circumferentially aligned with struts 13 at the distal end or may be circumferentially offset. The proximal conical section 16 and the distal conical section 18 may have the same or different number of struts 13.

Interspersing the proximal and distal central sections 20A, 20B may be a intermediate section 22. The intermediate section 22 may have a different shape, structure, and/or density from the proximal and distal central sections 20A, 20B. The intermediate section 22 may project radially outwardly from the proximal and distal central sections 20A, 20B. In some embodiments, the intermediate section 22 may extend radially outward along only a portion of the circumference of the device 10 (not shown). The intermediate section 22 may be relatively spherical in an unconstrained expansion configuration. In some embodiments, the intermediate section 22 may be non-spherical in an unconstrained expansion (e.g., globular, cylindrical, toroidal, etc.). This intermediate section 22 may be configured to span and/or prolapse into the aneurysm neck. The intermediate section 22 may initially push the coils deeper into the aneurysm to improve coil packing density.

The intermediate section 22 may be about the same density as the cylindrical sections 20A, 20B or could be different (e.g., a higher density). A high density intermediate section 22 may facilitate retention coils and/or prevent escape of coils into the blood vessel. In some embodiments, the mesh of the intermediate section 22 may comprise interstitial gaps having dimensions which are equal to or less than the diameter of the smallest embolization coil (e.g., about 0.01 inches) to avoid entangling coils with the device 10. The intermediate section 22 may comprise a relatively higher density than other portions of the device 10, the other portions having a lower density to minimize thrombogenesis. The intermediate section 22 may not comprise enough radial force upon expansion to deform the blood vessel wall outside of the aneurysm neck and therefore may not achieve an entirely expanded (e.g., spherical) conformation upon deployment, but may rather replicate the conformation of the proximal and/or distal central portions 20A, 20B along areas of the blood vessel not proximate to the aneurysm. The structure of the device 10 (e.g., the pitch or braid pattern) may be altered along the length of the device 10 in order to achieve variable radial rigidity. In some embodiments, the central section 20 may be coextensive with the intermediate section 22.

The proximal conical end 16 may be attached to a push wire 24 for positioning the device. The push wire 24 may be attached at the apex 26 of the conical section 16. The push wire 24 may incorporate a radiopaque marker. The distal wire conical section 18 may be attached to a guiding lead wire segment 25 and/or may incorporate a radiopaque marker. Alternatively, the distal conical section 18 may be eliminated entirely leaving an unobstructed opening to the central section 20 at the distal end 14 of the device 10, similar to other embodiments described herein.

In some embodiments, the device 10 may be composed of tightly braided metal wires, laser cut tube stock, or a hybrid of both. In many embodiments, the number of wires comprising the device is at least about 24. In some embodiments, the number of wires is at least about 48 or 64 or more. The wires may be braided one-over-one, two-over-two, two-over-one, one-over-two, etc. The wire density may vary depending on the section of the device. The wire may be formed of materials such as nitinol, DFT®, platinum, spring-tempered stainless steel, other metals, or polymers. In some embodiments, the wires comprise a 30% platinum core with a nitinol sheath. In some embodiments, the device 10 may be fabricated from fluoropolymers or shape-memory polymers. FIG. 2Di-2Dvi depict various examples of fluoropolymer monomers or polymers that may be used to coat wires or struts of a meshed device 10 as disclosed here or elsewhere herein. For example, the device 10 may comprise coatings of polyvinylidene fluoride (PVDF) (FIG. 2Di); poly(vinylidene fluoride co-hexafluoropropylene) (PVDF-HFP) copolymers (FIG. 2Dii); perfluoropropylene ($C_3F_6$); octafluoropropane ($C_3F_8$); poly(p-xylylene) polymers such as those derived from Parylene HT and/or Parylene AF-4 (FIG. 2Diii); poly(p-xylylene) polymers such as those derived from Parylene F and/or Parylene VT-4 (FIG. 2Div); poly(p-xylylene) polymers such as those depicted in FIG. 2Dv; 1H,1H,2H,2H-perfluorododecyltrichlorosilane ($CF_3(CF_2)_9CH_2CH_2SiCl_3$); (tridecafluoro-1,1,2,2, tetrahydrooctyl) silane ($CF_3(CF_2)_5CH_2CH_2SiH_3$); and/or hexadecafluordodec-11-en-1-yl trimethoxysilane (FIG. 2Dvi). In some embodiments, these coatings may serve as final coatings. In some embodiments, these coatings may be used as intermediate coatings. Intermediate coatings may help increase the surface coverage, for example, of a subsequently applied coatings, which may be the same or different as the intermediate coating.

In some embodiments, the device 10 is entirely composed of nitinol wire. In other embodiments, the device is composed of nitinol wire and wires of other material. To endow the device with sufficient radiopacity for visualization, DFT® wire or another radiopaque metal may be incorporated into the device, the wires may be coated with a radiopaque metal (e.g., gold, platinum, or tantalum), or printed particle or other marker bands may be applied to the device. At least 2, or 4 or 6 or more strands in, for example, a 64 strand weave, may comprise a radiopaque material such as platinum. In some embodiments, the wire diameter is about 0.0005 inches, about 0.001 inches, 0.002 inches, 0.003 inches, 0.004 inches, 0.005 inches, about 0.006 inches, about 0.007 inches, about 0.008 inches, about 0.009 inches, about 0.01 inches, less than 0.0005 inches, more than 0.01 inches, or within a range therebetween. In some embodiments, the device 10 is composed of wires of at least two different diameters, with smaller diameter wires used to fill gaps between the larger diameter wires and increase coverage of the surface of the device 10. In some embodiments, the braid and/or strut junctions are left uncoated so as to avoid the risk of generating debris upon fatigue during implantation.

In some embodiments, the device 10 may be at least about 5 mm, 8 mm, 10 mm, 12 mm, 15 mm, 20 mm, 25 mm, less than 5 mm, or more than 25 mm in length from the proximal end of the proximal central section 20A to the distal end of the distal central section 20B. The central sections 20A, 20B in an unconstrained expansion may be about 2 mm, 3 mm, 4 mm, 5 mm, 6 mm, 7 mm, 8 mm, 9 mm, 10 mm, less than 2 mm, or more than 10 mm in diameter. The intermediate section 22, in an unconstrained expansion, may be about 2 mm, 3 mm, 4 mm, 5 mm, 6 mm, 7 mm, 8 mm, 9 mm, 10 mm, less than 2 mm, or more than 10 mm in diameter upon expansion. In some embodiments, the intermediate section 22 may have a diameter that is about 100%, 110%, 115%, 120%, 125% 130%, 140%, 150%, 200%, or more than 200% of the diameter of the central section 20. For example, in some embodiments, the central section 20 may have a diameter of about 4-5 mm and the intermediate section 22 may have a diameter of about 5-6 mm in diameter upon expansion.

Prior to expansion, the device 10 may be sized to be received within a tubular delivery sheath with an internal diameter of about 0.018-0.021 inches (e.g., the outer diameter of the device 10 may be about 0.016-0.019 inches collapsed). In various embodiments, the intermediate section 22 (or portion of the device that interfaces the aneurysm) creates gaps between the wires (e.g., the largest dimension of the gap) that are less than about 0.005 inches, 0.006 inches, 0.007 inches, 0.009 inches, 0.010 inches, 0.011 inches, 0.012 inches, 0.013 inches, 0.014 inches, 0.015 inches, or more than 0.015 inches. In some embodiments, the gaps are preferably no more than about 0.008 inches, to prevent escape of the coils and to promote a high coil packing density. In some embodiments, the gaps elsewhere through the meshed device may be about 0.005 inches, 0.01 inches, 0.015 inches, 0.02 inches, 0.025 inches, 0.03 inches, 0.035 inches, 0.04 inches, 0.045 inches, 0.05 inches, 0.055 inches, 0.06 inches, 0.065 inches, 0.07 inches, 0.075 inches, 0.08 inches, 0.085 inches, 0.09 inches, 0.095 inches, 0.1 inches, 0.125 inches, 0.15 inches, 0.175 inches, 0.2 inches, 0.3 inches, 0.4 inches, 0.5 inches, less than 0.005 inches, more than 0.5 inches, or a dimension from any range there between. In some embodiments, the gaps throughout the meshed device 10 (e.g., near proximal and/or distal ends of the device) may be larger than those configured to be positioned adjacent the aneurysm neck (e.g., near the middle of the device 10). Areas with larger gap dimensions may create localized areas of low-density compared to areas with smaller gap dimensions. In some embodiments, interstitial gaps in areas of low-density may have about 105%, 110%, 115%, 120%, 125%, 130%, 135%, 140%, 150%, 175%, 200%, 250%, 300%, 400%, 500%, 600% 700%, 800%, 900%, 1000%, 2000%, 5000%, between 100% and 105%, more than 5000%, or any percentage in a range there between, larger areas or dimensions (e.g., diameter) than interstitial gaps in areas of high-density.

FIGS. 3A-5B schematically illustrate various examples of alternative embodiments of the device 10. In these embodiments, the device 10 comprises a central section 20, bounded by a tapered proximal section 28 and optionally a tapered distal section 30. The tapered distal section 30 may serve the same functions as the distal conical section in FIG. 2. FIG. 3A depicts a device 10 comprising symmetric tapered proximal and distal sections 28, 30. FIG. 3B depicts an end view of the device in FIG. 3A. FIG. 3C depicts a perspective view of the device in FIG. 3A. In some embodiments, the device 10 may include an intermediate section (not shown) the same as or similar to intermediate section 22 described elsewhere herein. Tapered proximal and distal sections 28, 30 may extend between the circumference of the central section 20 and a proximal apex 26 or distal apex 27, respectively. The push wire 24 may attach to the apex 26 of the tapered proximal section 28. Tapered proximal and distal sections 28, 30 may structurally join either the proximal end or the distal end of the central section 20 to an apex 26, 27, for instance, such that the force distribution between the central section 20 and the push wire 24 and/or an optional leading guide wire segment 25 is more uniformly distributed.

As seen in the end view in FIG. 3B, one or both end sections 28 and 30 may be shaped so as to conform to the surface shape of the central section 20 (e.g. cylindrical shape). The tapered sections 28, 30 may extend axially and circumferentially to terminate in apexes 26, 27, respectively, that are aligned along the outer circumference of the central section 20, to leave a fully patent central lumen 40 throughout the axial length of the device 10, without any cross struts to create flow turbulence. A device with an unobstructed lumen may reduce the thrombogenicity of the device. In other embodiments, the proximal apex 26 and/or distal apex may be positioned slightly radially outside the lumen 40 as defined by the cross-section of the central section 20. In some implementations, the apexes 26, 27 may be circumferentially aligned along the circumference of the central section 20, such that they are generally collinear. In some implementations, the device 10 may be formed from braided wires, as described elsewhere herein. The braided wires may be aligned at one or both of the apexes 26, 27. The aligned wires may extend parallel to each other for a distance after coming together to form a generally linear segment. The push wire 24 may be connected to a proximal end of the proximal linear segment, positioned proximally from the proximal apex 27, such as described elsewhere herein. A distal lead segment 25 may be connected or formed by a distal end of the distal linear segment when present.

In some embodiments, the proximal tapered section 28 and/or distal tapered section 30 may have a lower density than the central section 20. In some embodiments, a low-density portion of the device 10 may extend from the proximal apex 26 and/or from the distal apex 27 to a point within the central section 20 (e.g., to an intermediate section 22). In some embodiments, a low-density portion may not extend the entire length of the tapered proximal section 28 and/or the tapered distal section 30. In some embodiments, the device 10 may comprise a density gradient (e.g. continuously or incrementally increasing in density from the proximal and/or distal ends toward the center). In some implementations, the tapered sections 28, 30 may have areas of concentrated, relatively high density (e.g., at the apex), but may generally comprise a lower density than the central section 20 (e.g., an average density). In some implementations, the tapered sections 28, 30 or other portions of the device 10 which may be configured to have a relatively lower density may have struts or wires configured in a pattern that creates an overall lower density. For example, the pitch of the wires may be greater along lengths of the device 10 configured to have a relatively low density and lesser along lengths of the device 10 configured to have a relatively high density. The low-density sections (e.g., tapered sections 28, 30 and/or proximal and distal ends of the central section 20) may have a lesser number of struts and wires than the high-density sections (e.g., central section 20 or intermediate section 22). For example, not all the struts or wires of the central section 20 may continue to the proximal apex 26. The interstitial gaps within the low-density sections of the device 10 may generally have larger areas than the areas of the gaps within high-density sections of the device.

FIGS. 4A-5B illustrate embodiments of the device 10, in which the distal tapered section 30 may be eliminated altogether. FIGS. 4A-4C schematically illustrate one open-faced embodiment of the device 10. FIG. 4A shows a side elevation view of the device 10. The distal end 14 may end in a distal open face 31 leading to the central lumen 40. The distal open face 31 may be approximately perpendicular to the axial length of the device 10. In other embodiments, the distal open face 31 may form an angle with the longitudinal axis of the device 10. The angle may be either acute or obtuse, as described elsewhere herein. FIG. 4B shows a proximal perspective view of the device 10 of FIG. 4A. FIG. 4C shows a close-up view of an edge (e.g., a distal edge) of the device 10 comprising such an open configuration. FIG. 4C shows the distal edge of the device 10 in which each distally extending filament (e.g., strut or wire) may be bent to form an atraumatic apex and thereafter extend proximally along central section 20. In further embodiments, both the distal and proximal ends 12, 14 of the device 10 may comprise open ends with both tapered sections 28, 30 eliminated and the push wire 24 contiguous with or attached directly to the circumference of the central section 20. In some embodiments, the push wire 24 may extend from a proximal end 12 of the device 10 to the distal end 14 of the device or to a point in between. In preferred embodiments, the wires of the device 10 may be folded over at the open end and weaved back into the device rather than being cut such that the edges are atraumatic, as shown in FIG. 4C. Other suitable methods may be used as well for making the device edges atraumatic.

FIGS. 5A-5B show another embodiment, in which a central annular protrusion or bump section 23, similar to the spherical intermediate section 22 of FIGS. 2A-2C, is positioned in between two cylindrical sections 20A, 20B. FIG. 5A shows a side elevation of the device 10. FIG. 5B shows a proximal end view of the device 10. The protrusion 23 may be formed as the same density as the cylindrical sections 20A, 20B or of a higher density or of a lower density. Bump section 23 may serve the same purpose as the generally spherical intermediate section 22 described in FIGS. 2A-2C.

Figure 6A:
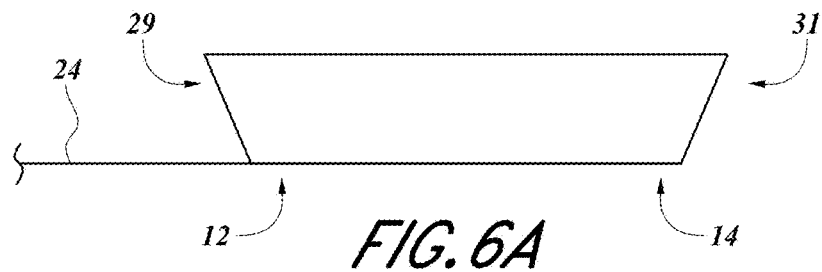
FIGS. 6A-6F depict schematic side view diagrams of six various alternative configurations of the device.
Figure 6B:
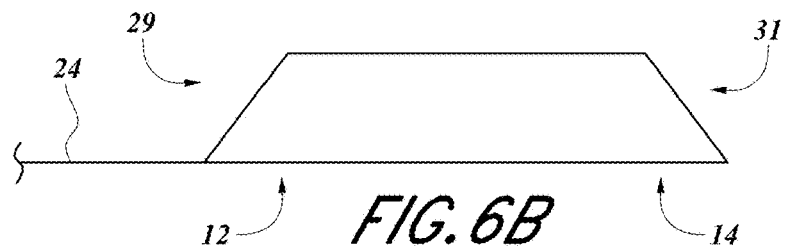
Figure 6C:
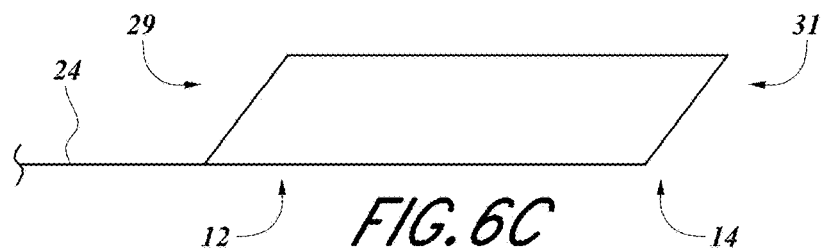
Figure 6D:
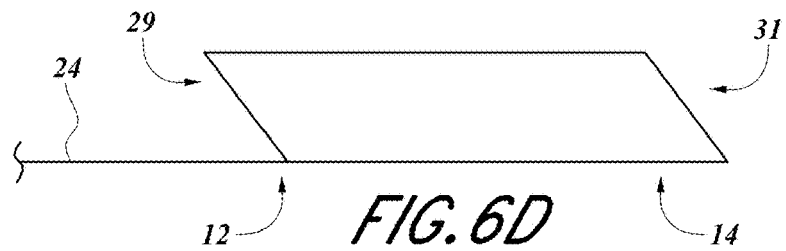
Figure 6E:
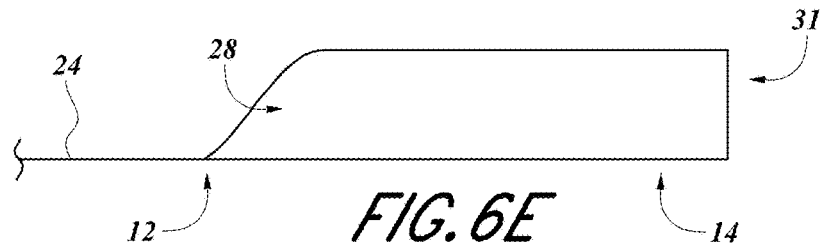
Figure 6F:
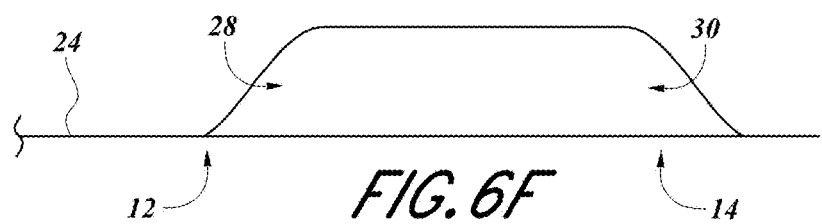

FIGS. 6A-6F depict schematic side view diagrams of five various configurations of the device 10. FIGS. 6A-6F show a number of additional configurations the device 10 may take, wherein the angle between the axis aligned with the push wire 24 and the end face of the device 10 may be either perpendicular, obtuse, or acute at either end of the device. FIGS. 6A-6D depict configurations in which both the proximal end 12 and distal end 14 of the device 10 comprise open configurations. The open configuration devices 10 may not comprise proximal and distal tapered sections 28, 30. The proximal and distal open faces 29, 31 may be defined by edges, such as the edge illustrated in FIG. 4C. FIG. 6A depicts a device 10 in which both the proximal open face 29 and distal open 31 extend away from the axis defined by the push wire 24 at acute angles facing the proximal and distal sides, respectively. FIG. 6B depicts a device 10 in which both the proximal open face 29 and distal open 31 extend away from the axis defined by the push wire 24 at obtuse angles. FIG. 6C depicts a device 10 in which the proximal open face 29 extends away from the push wire axis at an obtuse angle and the distal open face 31 extends away from the push wire axis at an acute angle. FIG. 6D depicts the opposite, in which the proximal open face 29 extends away from the push wire axis at an acute angle and the distal open face 31 extends away from the push wire axis at an obtuse angle. Variations are also possible in which either the proximal open face 29 and/or the distal open faced 31 are substantially perpendicular to the push wire axis. FIGS. 6E-6F depict devices 10 in which the proximal end 12 is joined to the push wire 24 via a tapered proximal section 28. FIG. 6E depicts a device 10 comprising an open distal configuration with distal open face 31. The open face may be perpendicular to the push wire axis, as shown, or may form an obtuse or acute angle. FIG. 6F depicts a device 10 comprising both a proximal tapered section 28 and a distal tapered section 30. In some variations, the distal end 14 could comprise a tapered section 30 and the proximal end 12 could comprise and open proximal face 29. The inclusion of tapered sections, particularly the proximal tapered section 28, may make the device 10 more structurally stable. The inclusion of open faces may minimize the thrombogenicity of the device 10.

The physical design of the device 10 may impact its biocompatibility, particularly by the manner in which it obstructs natural blood flow. Platelet activation may be reduced decreasing the stress platelets experience as blood flows across the device 10. Both the amount of amount of device material the blood encounters as it flows (i.e. the fraction of the blood vessel cross section occupied by the device) as well as the angle at which the device interfaces the blood flow (the take-off angle) will influence the stress experienced by platelets and their resulting activation. In some embodiments, the stress experienced by platelets flowing over the device can be approximately modeled according to the following equation, wherein $\Delta P$ represents the pressure differential across the proximal section of the device 10 (e.g. tapered proximal section 28) from the push wire 24 to the beginning of the central section 20 of the device 10; $\rho$ represents the fluid density; $\phi$ represents the fraction of the cross-sectional area (i.e. flow path) consumed by the device 10; $\theta$ represents the take-off angle, where 0° indicates the device wire or strut is entirely parallel to the blood vessel and/or the direction of blood flow and 90° indicates the device wire or strut is entirely perpendicular to blood vessel and/or the direction of the blood flow; U represents the fluid velocity; R represents the radius of wires or struts; and $\mu$ represents the fluid viscosity:

$$\Delta P = \frac{1}{2}\rho \phi \sin\theta \, U^2 \left(\frac{\rho U R}{\mu(1-\phi)}\right)^{1/2}. \quad \text{Eq. [1]}$$

Figure 7A:
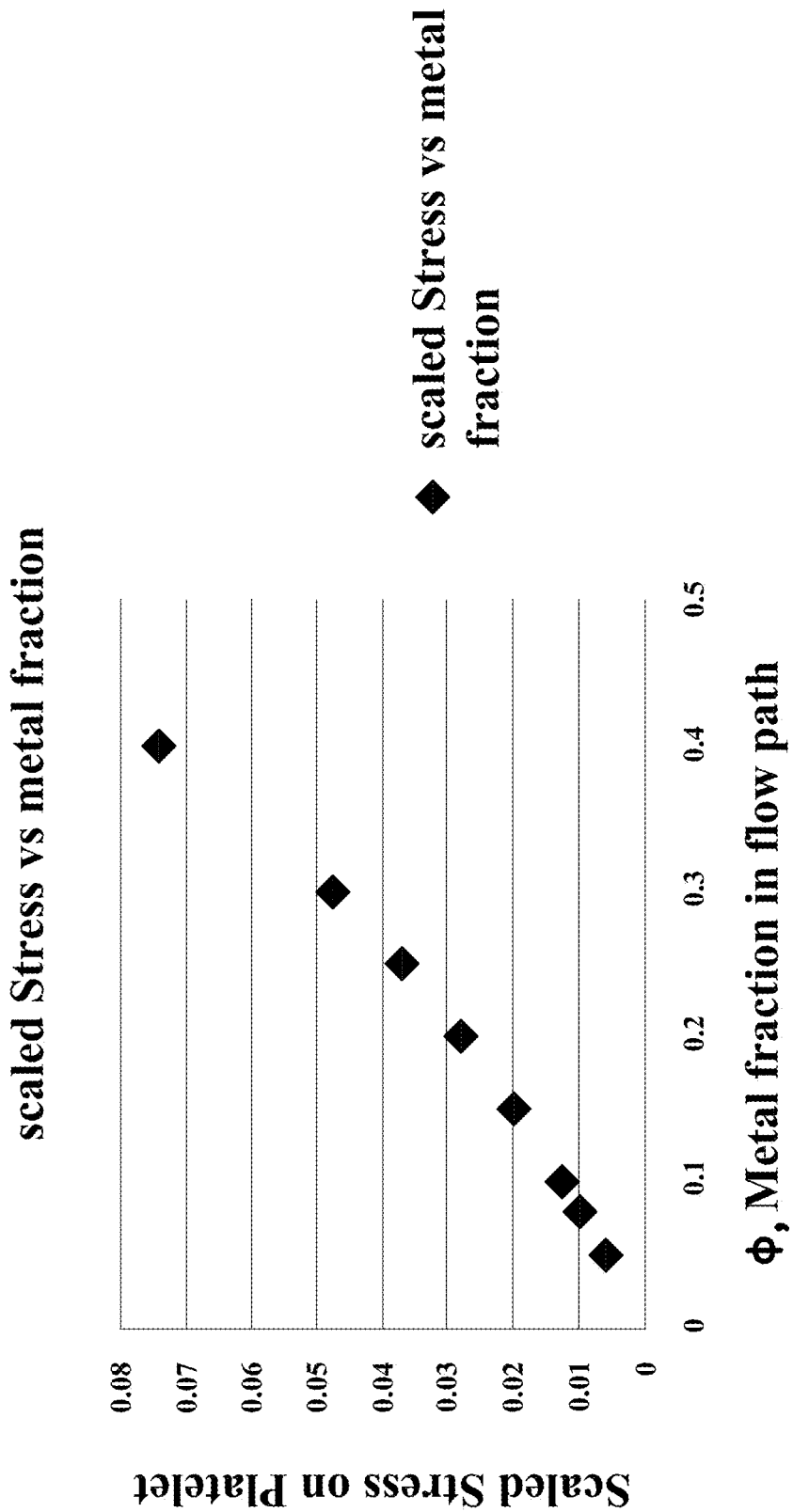
FIGS. 7A-7C show relative amounts of stress platelets will experience traveling across the device.
Figure 7B:
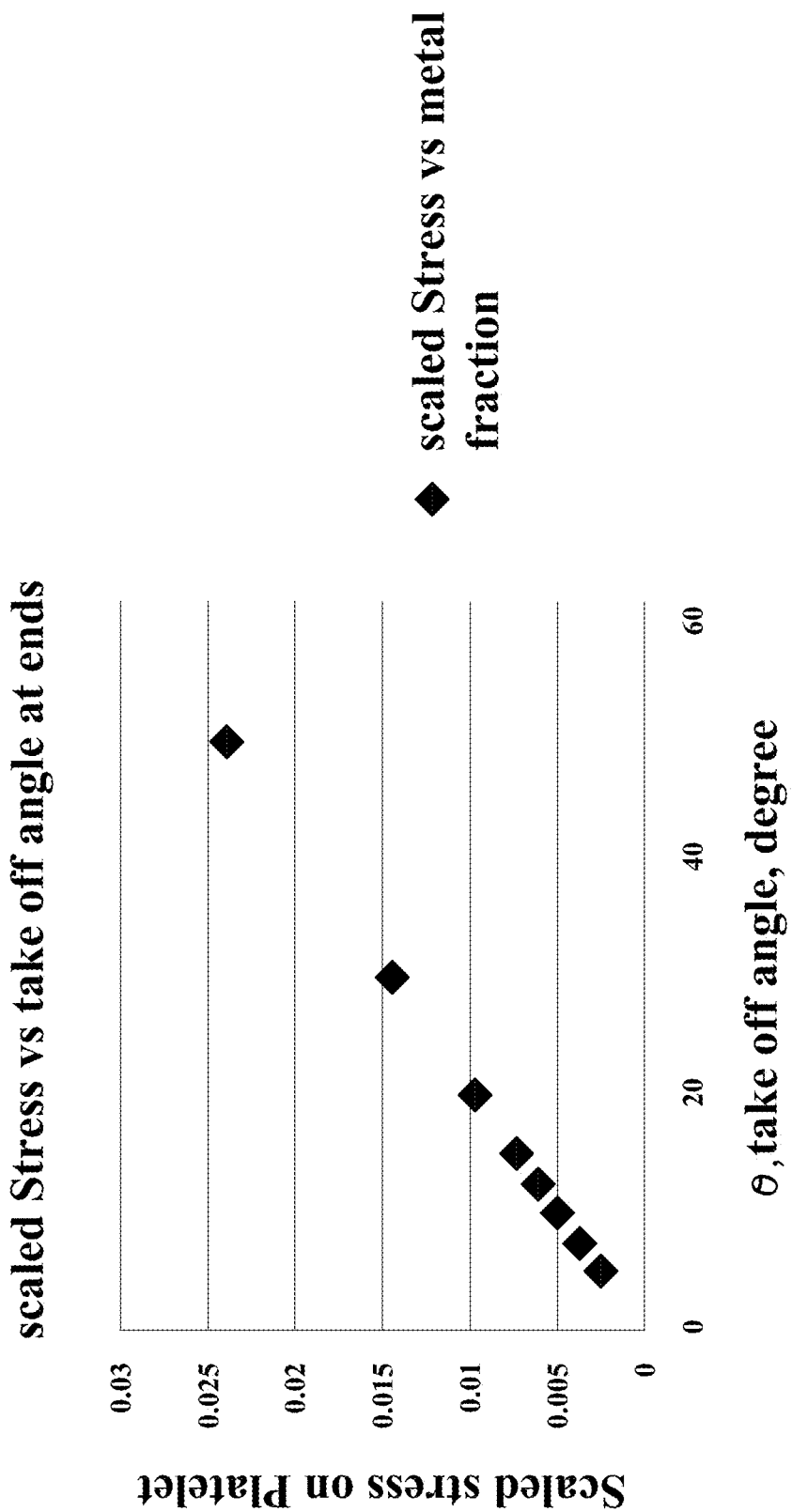

Thus, in the above equation for a device constructed of wires or struts of a given size, the pressure differential may be altered by modulating either the take-off angle, $\theta$, and/or the device fraction in the flow path, $\phi$. FIG. 7A depicts the relative stress experienced by platelets (proportional to $\Delta P$) along the y-axis for a constant $\theta$ (here 20°) across a range $\phi$, plotted along the x-axis. FIG. 7B, conversely, depicts the relative stress experienced by platelets (proportional to $\Delta P$) along the y-axis for a constant $\phi$ (here 0.08) across a range of device fractions in the flow path, plotted along the x-axis. In some embodiments, the device 10 possesses a $\theta$ value as close to zero as possible while maintaining sufficient stability within the device. Without limitation, the $\theta$ value may be, for example, about or no greater than 85 degrees, 80 degrees, 75 degrees, 65 degrees, 60 degrees, 55 degrees, 50 degrees, 45 degrees, 40 degrees, 35 degrees, 30 degrees, 20 degrees, 15 degrees, 10 degrees, 5 degrees, more than 85 degrees, or less than 5 degrees. In some embodiments, the θ value may be at least about 10 degrees, 15 degrees, 30 degrees, 45 degrees, 50 degrees, 60 degrees, or 80 degrees. In some embodiments, the θ value (take-off angle) may be optimal when between about 30-80 degrees, about 40-70 degrees, about 50-60 degrees, or ranges there between in order to provide sufficient structural integrity and minimize thrombogenesis. The proximal section (e.g., tapered proximal section 30) may comprise a longer length for devices 10 comprising lower take-off angles. In some embodiments, the length of the proximal section (e.g., tapered proximal section 28) and/or the length of the distal section (e.g., tapered distal section 30), may be about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 20 cm, 25 cm, 30 cm, 35 cm, 40 cm, 45 cm, 50 cm, less than 1 cm, more than 50 cm, or a length in any range there between. In some embodiments, the length of the of the proximal section (e.g., tapered proximal section 28) and/or the length of the distal section (e.g., tapered distal section 30), may be about 5%, 10%, 15%, 20%, 25%, 30%, 40%, 50%, 60%, 70%, 80%, 90%, 100%, less than 5%, more than 100% of the length of the central section 20 or a length in a range defined there between.

Similarly, in some embodiments, the device 10 possesses a φ value as close to zero as possible while maintaining sufficient stability within the device 10. Without limitation, the φ value may be, for example, about or no greater than 0.5, 0.45, 0.4, 0.35, 0.3, 0.25, 0.2, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, greater than 0.5, less than 0.001, or a fraction from any range there between. In some implementations, such as where the device 10 is configured (e.g., in an expanded configuration) to substantially occupy the diameter of the blood vessel in which it sits (e.g., the outer diameter of the device 10 is approximately equal to the inner diameter of the blood vessel), the φ value may be approximated by the fraction of the cross-sectional area of the device 10 (e.g., the cross-sectional area defined by the outer diameter of the device 10) occupied by material of the device 10.

Furthermore, platelet activation is expected to be impacted by the braid structure of the braided wires of some embodiments, particularly due to interception of platelets in motion within the recirculation volume by braids at the wall. Platelet activation due to this phenomenon can be approximately modeled according to the following equation, wherein Ac represents a level of platelet activation; r represents the wire radius, E represents the porosity (i.e. 1—braid density), L represents the length of the wire, and R represents the radius of the blood vessel:

$$Ac = \frac{\epsilon 2\pi RLAr(4r)^2}{R^4} = \frac{128\pi \epsilon Lr^3}{R^3}.$$ Eq. [2]

Figure 7C:
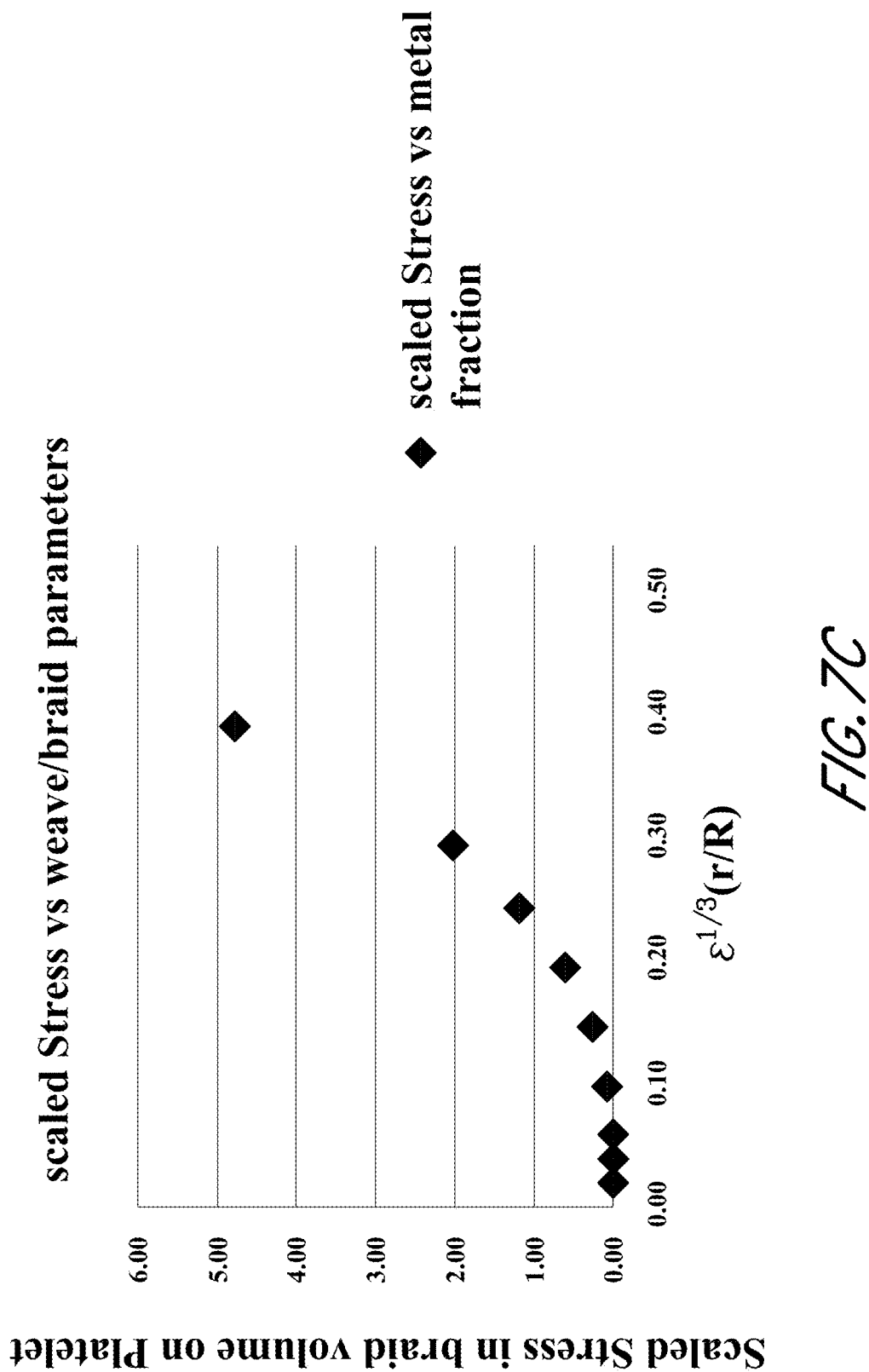

FIG. 4C depicts the relative stress experienced by platelets (proportional to Ac), along the y-axis, across a range of the parameter $\epsilon^{1/3}(r/R)$, which incorporates the pertinent design variables. In some embodiments, the device possesses a design parameter value $\epsilon^{1/3}(r/R)$ as close to zero as possible while maintaining sufficient stability within the device. Without limitation, the value may be, for example, about or no greater than 0.5, 0.4, 0.37, 0.35, 0.33, 0.3, 0.27, 0.25, 0.23, 0.2, 0.15, 0.1, 0.05, more than 0.5, or less than 0.05. Minimizing the wire thickness may minimize the design parameter of Eq. 2. Similarly, as described elsewhere herein, the overall braid density of the device may be minimized. The wire thickness and braid density may be minimized for a certain radial strength, resulting in reduction of flow stagnation and/or boundary layer separation with the vessel wall along the axial direction of the blood flow. Reducing flow stagnation may generally reduce thrombogenesis. In preferred embodiments, all three of the design variables—φ, θ, and $\epsilon^{1/3}(r/R)$—will be as low as possible, or at least two of the design variables will be as low as possible, while maintaining stability within the device 10. In some embodiments, one of the design variables will be as low as possible. In some embodiments, the device 10 is configured to operate in the lower ranges of one, two, or three of the graphs illustrated in FIGS. 7A-7C while maintaining sufficient structural integrity (e.g., hoop strength). The device may be optimized for minimal thrombogenesis, particularly from thrombogenesis resulting from blood flow impacting the structure of the device 10.

In some embodiments, the entire length of implant 10 may comprise a wire weave, a laser cut hypo tube, and/or a hypo tube formed via vapor deposition (e.g., by vapor depositing nitinol around a mandrel using a mask). Alternatively, in some embodiments, at least the proximal section 28 and optionally also the distal section 30 may be formed from a hypo tube, while the central section 20 may comprise a multi filament weave. In some embodiments, a central section 20, or a portion thereof, may comprise a laser cut hypo tube and sections proximal to and/or distal to the laser cut hypo tube may comprise a multi filament weave. The device 10 may exert a radially outward force along the blood vessel (e.g., a counter force to radial compression). The radial force may vary, for example, along the length of the device 10. In some embodiments, the radial force may be modulated by physical parameters of a woven device, such as the pitch of the braid, the number of wires, the weaving pattern of the wires, and/or the density of the device 10. In some embodiments, selective treatment (e.g., selective heat treatment) may be used to spatially modulate the physical properties of the device 10. Preferably, the radial force at the distal portion of proximal section 28 adjacent a transition 36 (FIG. 3A, FIG. 4A) between the proximal section 28 and the central section 20 is greater than the radial force at a midpoint of the central section 20 in some embodiments. This helps to maintain patency of the proximal opening to the central lumen 40, while minimizing leading edge flow obstruction and resultant blood flow turbulence. The radial force at the midpoint may be lower to minimize exerting excessive pressure on the aneurysm. The radial force in the vicinity of transition 36 may be about or at least 110%, and in some embodiments about or at least 115%, 120%, 125%, 130%, 140%, 150%, 175%, 200%, 300%, or greater than 300% the radial force at the midpoint of central section 20.

Figure 8A:
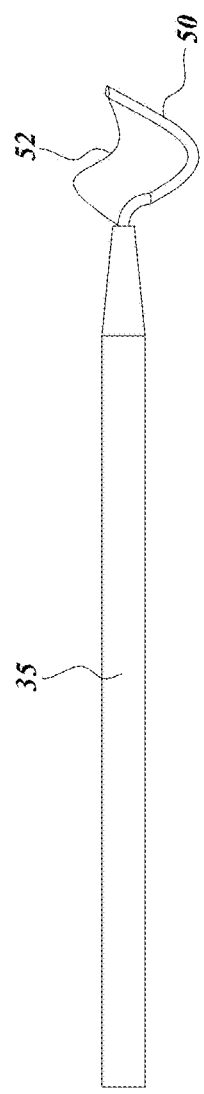
Figure 8B:
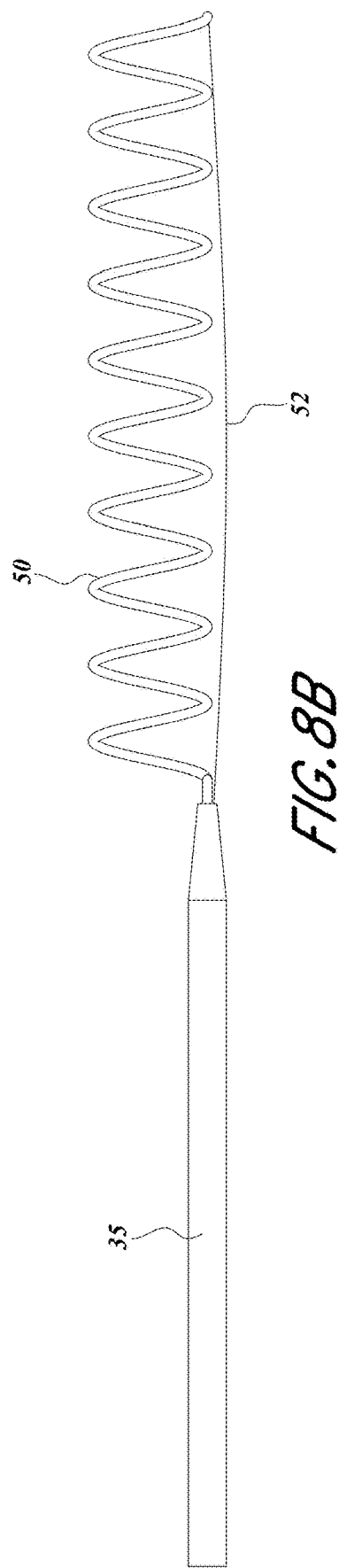
Figure 8C:
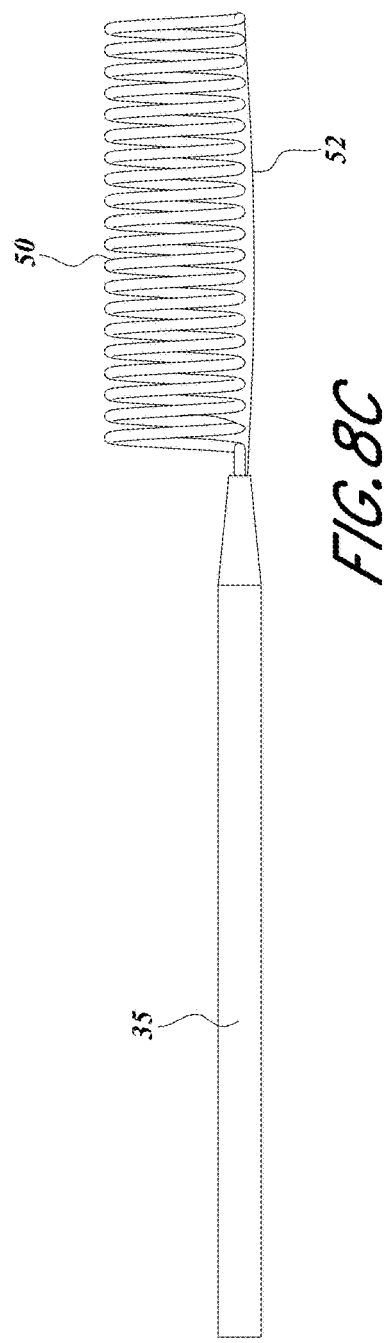

FIGS. 8A-8D depict another example of a device 10. In an alternative embodiment, the device 10 may be comprised of a single coil 50. The coil 50 may be constructed of the same materials as other embodiments of the device 10. The coil 50 may be inserted into the blood vessel through a microcatheter or other delivery device 35 as a relatively linear wire, as seen in FIG. 8A. The delivery device 35 may confine and bias the coil 50 into a linear conformation for delivery and the coil 50 may assume a bent/coiled conformation upon release from the delivery device 35. The distal end of the coil 50 may be tethered to the microcatheter by a wire or string tether 52. As shown in FIGS. 8B-8D, the tether 52 may be used to pull the distal end of the coil 50 toward proximal end of the coil 50 such that a spring-like coil formation is formed. The tether 52 may be used to then secure the coil 50 in this conformation. The coil 50 may be kinked and/or relatively elastic to help it achieve the coiled formation when it is delivered from the microcatheter 25. In some embodiments, the coil may have different structural or mechanical properties (e.g., pitch) along various portions of its length. These structural differences may create sections of relatively low and high density, as described elsewhere herein.

The push wire 24 is preferably connected to the implant 10 with sufficient structural integrity to enable proximal retraction of the push wire 24 to draw the implant 10 back into the deployment sheath. At least one or two or four or six or more struts in the proximal section 28 may have a greater cross-sectional area than the cross-sectional area of the filaments making up the weave of central section 20. These reinforcement struts may be bonded directly or indirectly to the filaments of central section 20, to distribute pulling force over a greater area, and reduce the risk of detachment. Alternatively, push wire 24 may extend axially throughout the length of the implant device 10, and extended beyond to form the lead segment 25. The tubular body of device 10 may be bonded to the push wire 24 at both the tapered proximal section 28 and the tapered distal section 30 and optionally along the length of central section 20.

In the implementation illustrated in FIG. 3A, the proximal section 28 inclines radially outwardly in the distal direction at approximately a 45° take-off angle with respect to the longitudinal axis of push wire 24. In an embodiment intended for use as a temporary scaffold during coil implantation, the initial ramp angle of the segment (e.g., the first one or two mm of the proximal section 28) is preferably less than 45 degrees, and in some implementations no more than about 35 degrees, 30 degrees, 20 degrees, 15 degrees, 10 degrees, or less than 10 degrees, to facilitate resheathing the device 10 into the deployment catheter by proximal retraction of the push wire 24. In some embodiments, the take-off angle of the proximal tapered section 28 may be a minimum angle that provides sufficient structural integrity (e.g., hoop rigidity) to the device 10, which may depend on the density of the device 10 or at least of the proximal tapered section 28. The take-off angle may be about or at least 10 degrees, 15 degrees, 20 degrees, 25 degrees, 30 degrees, 40 degrees, 45 degrees, 50 degrees, 55 degrees, 60 degrees, 70 degrees, 75 degrees, 80 degrees, or more than 80 degrees.

In some embodiments, the device 10 may be formed similar to a traditional stent rather than from braided wires. For instance, the device 10 may be fabricated by laser cutting a metallic tube to form struts, as described elsewhere herein. In further embodiments, the device may be fabricated from both a stent structure with braided wires. The braided wires may be laser welded to the stent structure, allowing increased stability, yet a more open design. In some embodiments, the central section 20 and/or intermediate section 22 (sections which may be relatively higher density) are composed primarily of braided wires, while the proximal and distal low-density sections are fabricated from a metal tube.

FIGS. 9A-9B schematically illustrate side views of the proximal and distal ends, respectively, of the mesh portion of the device 10. FIG. 9A depicts the connection between the push wire 24 and the braided structure 70 forming the mesh portion of device 10. The configuration of the junction between the braided structure 70 and the push wire 24 may be configured to provide a mechanically robust joint (e.g., able to withstand compressive, tensile, and/or flexural forces). The proximal portion of the braided structure 70 may overlap the distal portion of the push wire 24. The various wires of the braided structure 70 may circumferentially surround the push wire 24 at the junction between the braided structure 70 and the push wire 24. The push wire 24 may be fabricated of any suitable material, including the same materials used to fabricate the braided structure (e.g., the wires or strands) as described elsewhere herein. For example, the push wire 24 may comprise nitinol and/or stainless steel. The push wire 24 may have a circular, round, square, or any other suitably shaped cross-section. The push wire 24 may have a diameter (or largest cross-sectional dimension) of about 0.005 inches, 0.01 inches, 0.015 inches, 0.02 inches, 0.025 inches, less than 0.005 inches, more than 0.02 inches, or a diameter within a range there between. In some embodiments, the push wire 24 tapers at its distal end (e.g., over a distal 2-5 cm portion of the push wire 24). The smallest diameter of the tapered portion may be about 0.001 inches, 0.002 inches, 0.003 inches, 0.004 inches, 0.005 inches, 0.006 inches, 0.007 inches, 0.008 inches, 0.009 inches, 0.01 inches, less than 0.001 inches, more than 0.01 inches, or in a range there between.

In some embodiments, one or more rings 76 (e.g., 2, 3, 4, 5, more than 5 rings) may be positioned over the push wire 24. The rings 76 may be positioned entirely or at least partially over the tapered portion of the push wire 24. The rings 76 may be positioned along the overlap of and between the braided portion 70 and the push wire 24. The rings 76 may increase the tensile strength of the joint. In some embodiments, the rings comprise polyether ether ketone (PEEK) or another suitable plastic. The rings 76 may be melted onto the push wire 24. In some embodiments, the rings 76 are about 1 mm wide. The rings 76 may be spaced from each other by about 1 cm, 1.25 cm, 1.5 cm, 1.75 cm, 2 cm, 3 cm, 5 cm, more than 5 cm, or less than 1 cm. In some embodiments, spacing the rings by at least about 1 cm apart provides sufficiently low flexural stiffness. The rings 76 may be spaced uniformly apart. In some embodiments, the rings 76 may be unevenly spaced apart. Spacing the rings 76 unevenly may provide a smoother transition in flexural stiffness. For example, the rings may be spaced continually farther apart along the distal direction to make the joint progressively more flexible as the push wire 24 extends distally.

In some embodiments, the proximal joint may include an inner jacket 74. The inner jacket 74 may be a tubular sleeve. The inner jacket 74 may comprise polytetrafluoroethylene (PTFE). The inner jacket 74 may be positioned around the push wire 24 proximal to the proximal-most ring 76. The inner jacket 74 may abut the proximal-most ring 76. Positioning the inner jacket 74 adjacent the rings 76 rather than over the rings 76 can minimize the overall diameter of the joint. Positioning the inner jacket 74 entirely over a tapered portion of the push wire 24 may minimize the overall diameter of the joint. The inner jacket 74 may serve to smooth the transition in flexural stiffness of the joint. The jacket may be melted onto the push wire 24.

The proximal end (i.e. proximal tail) of the braided structure 70 may be inserted through a marker band 78. The marker band 78 may be substantially ring-shaped. The marker band 78 may be radiopaque. The marker band 78 may visually indicate the proximal end of the meshed device 10 and may facilitate positioning the meshed device 10 adjacent an aneurysm. In other embodiments, a marker band 78 may be attached around a proximal end of the braided structure 70 or otherwise joined to the device 10 by any suitable means. The marker band 78 may facilitate the co-aligning of the wire strands of the braided structure 70 into a linear segment. The wires may begin to flare away from each other to radially expand (e.g., as in the tapered proximal section 28) on the distal side of the marker band 78. The distal end of the push wire 24 may be inserted into the proximal end of the braided structure 70. The wires of the braided structure 70 may be uniformly distributed around the circumference of the push wire 24 in order to evenly distribute the radial purchase to the push wire subassembly (e.g., the push wire 24, the rings 76, and the inner jacket 76). The push wire 24 may be inserted up to or near a proximal end of the marker band 78. An adhesive may be applied to the distal end of the push wire 24 and/or to the marker band 78 (e.g., on a distal side of the marker band) in order to increase the tensile strength of the proximal joint. In some embodiments, an outer jacket 72 may be positioned over the joint. The outer jacket 72 may be positioned over the joint (e.g., push wire 24, rings 76, the proximal tail of braided structure 70, and the inner jacket 74). The outer jacket 72 may comprise polyether ether ketone (PEEK). Positioning the outer jacket 72 adjacent to rather than over the marker band 78 may minimize the overall diameter of the joint. The outer jacket 72 may be melted over the remainder of the joint assembly. In some embodiments, an adhesive may be applied between the outer jacket 72 and the remainder of the joint to increase the mechanical robustness of the joint and/or to smooth the transition in diameter between the push wire 24 and the outer diameter of the outer jacket 72. In some embodiments, the length of the proximal joint (from the distal end of the marker band 78 to the proximal end of the push wire 24 may be about 100 cm, 125 cm, 150 cm, 180 cm, 200 cm, 250 cm, 300 cm, less than 100 cm, more than 100 cm, or a length in a range there between.

FIG. 9B schematically depicts an example of a distal end of braided structure 70. The distal end of the braded structure 70 may be configured to facilitate anchoring the device 10 in vessel lumen. For example, the distal end may be configured to provide stability during the deployment and/or positioning of the device 10 proximate to the vessel aneurysm. Similar to the proximal end of the braided structure 70, the wire strands at distal end of the braided structure 70 may be placed through a marker band 78. The marker band 78 may facilitate co-aligning the distal ends of the wire strands into a substantially linear segment. The wire strands may flare out and extend away from each other on the proximal side of the marker band 78. The positioning of marker bands 78 on proximal and distal sides of the meshed device 10 may facilitate the positioning of the mesh device 10 adjacent to the aneurysm. The proximal marker band 78 may be positioned proximal of the aneurysm and the distal marker band 78 may be positioned distal of the aneurysm to properly align the device 10. The exact positioning of the aneurysm between the two bands 78 may facilitate the alignment of an intermediate section 22 (e.g., a high-density section) adjacent the aneurysm. An adhesive may be applied between the distal marker band 78 and the braided structure 70 (e.g., on a proximal side of the marker band 78). In some embodiments, the wire strands of the braided structure 70 may extend about 0.5 mm, 1 mm, 1.5 mm, 2 mm, 3 mm, 4 mm, 5 mm, 10 mm, 15 mm, 20 mm, less than 0.5 mm, more than 20 mm, or some length in a range there between beyond the distal marker band 78. The distal ends of the wire strands may be aligned parallel to each other and may form a distal lead segment 25. The distal end of the wire strands may be capped with an adhesive cap 82 (e.g., a UV curable adhesive) which may form an atraumatic end to the device 10. The adhesive cap 82 may facilitate the retention of the wire strands of the braided structure 70 together. In some embodiments, a coil 80 (e.g., a helical coil) may be wrapped around the lead segment of the braided structure 70. The coil 80 may comprise, for example, platinum and/or iridium. In some implementations, the coil 80 may increase the weight of the distal end and may facilitate in positioning the device 10. The coil 80 may serve to facilitate retaining the wire strands of the lead segment together.

Figure 10A:
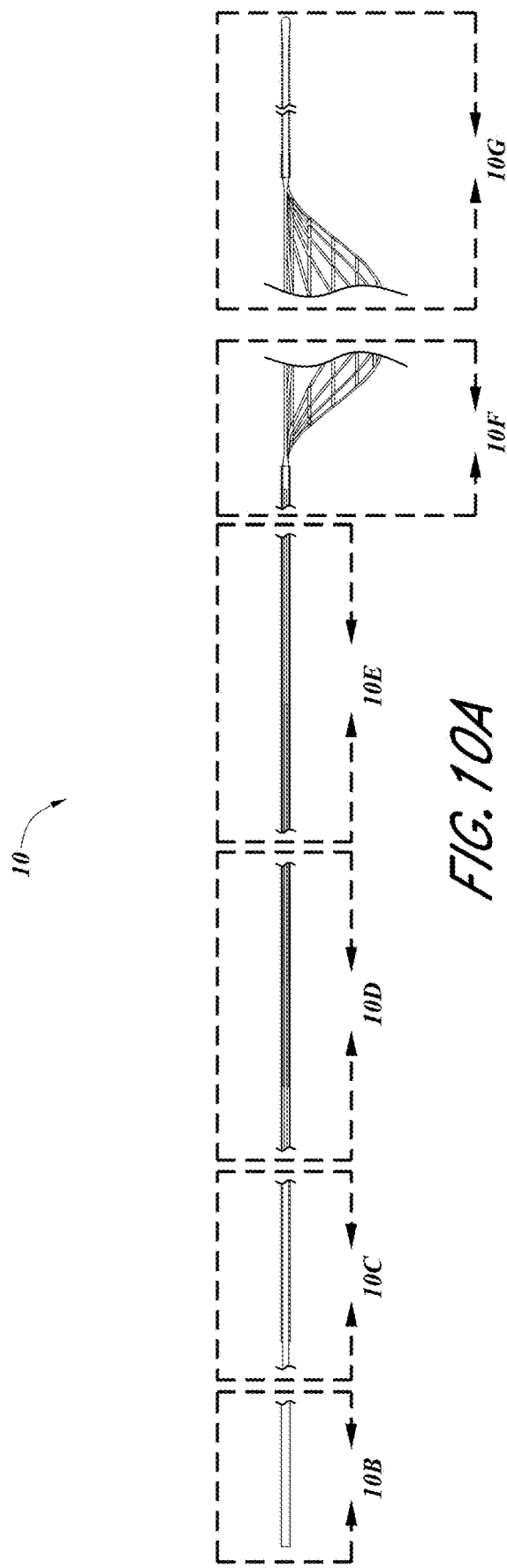

FIGS. 10A-10G schematically illustrate an example of a device 10 including a joint with a push wire 24 and a lead segment 25. FIG. 10A schematically illustrates various segments of the device 10 in cross-section and FIGS. 10B-10G schematically illustrate close-up views of the various segments shown in FIG. 10A. The device 10 may be configured similar to that illustrated in FIGS. 9A-9B. FIG. 10B depicts the push wire 24. FIG. 10C depicts the push wire 24 extending through a proximal end of an outer jacket 72. FIG. 10D depicts the proximal end or tail of the braided structure 70 surrounding the push wire 24. The push wire 24 may taper causing its diameter to become less than an inner diameter of the outer jacket 72. In some embodiments, the outer jacket 72 may be conformed to the diameter of the push wire 24. FIG. 10E depicts the distal end of the push wire 24 and the proximal end of the braided structure 70 extending through a marker band 78. The braided structure 70 expands into the tapered proximal section 28 on the distal side of marker band 78. FIG. 10F depicts the distal tapered section 30 of the braided structure 70 extending through a marker band 78 and a coil 80 around the distal portion of the braided structure 70. FIG. 10G depicts a distal end of the braided structure 70. In some embodiments, the distal end of the braided structure 70 may be configured to form an atraumatic tip which may have an expanded diameter and/or a round tip. The coil 80 may extend to the distal end or near the distal end of the lead segment 25. In some embodiments, the proximal tail of the braided structure 70 may extend about or at least 10 mm, 20 mm, 30 mm, 40 mm, 50 mm, 60 mm, 70 mm, 80 mm, 90 mm, 100 mm, less than 10 mm, or more than 100 mm from the marker band 78 and/or proximal apex. In some embodiments, the push wire 24 may extend to a length that is about 5 mm, 10 mm, 15 mm, 20 mm, 25 mm, 30 mm, 35 mm, 40 mm, 45 mm, 50 mm, less than 5 mm, or more than 50 mm from the marker band 78 and/or proximal apex. The length of overlap between the push wire 24 and the braided structure 70 may be about 10 mm, 20 mm, 30 mm, 40 mm, 50 mm, 60 mm, 70 mm, 80 mm, 90 mm, 100 mm, less than 10 mm, or more than 100 mm.

In some embodiments, the device 10 may be provided with a tubular sleeve 60 in addition to or alternatively to the coating on individual struts. In some embodiments, the coating may be applied completely or partially over portions of the device 10 to form a sleeve 60 or partial sleeve. FIG. 11A schematically depicts the application of a sleeve 60 to the device 10. The sleeve 60 and/or interstitial coating may serve to help secure coils within an aneurysm and/or may provide a thromboresistant or otherwise biocompatible surface to the device 10. The sleeve 60 and/or interstitial coating may minimize disruption to the natural blood flow, such as by preventing blood flow through the interstitial gaps of the mesh device 10. The sleeve 60 and/or coating may make for a more robust flow-diversion device which is less thrombogenic. The sleeve 60 and/or coating may also be beneficial when applied over the aneurysm neck. Using the sleeve 60 and/or coating to occlude or partially occlude the aneurysm from the vascular blood flow may prevent rupture/ burst of the aneurysm and/or may diminish blood loss in the event the aneurysm does burst.

Figure 11D:
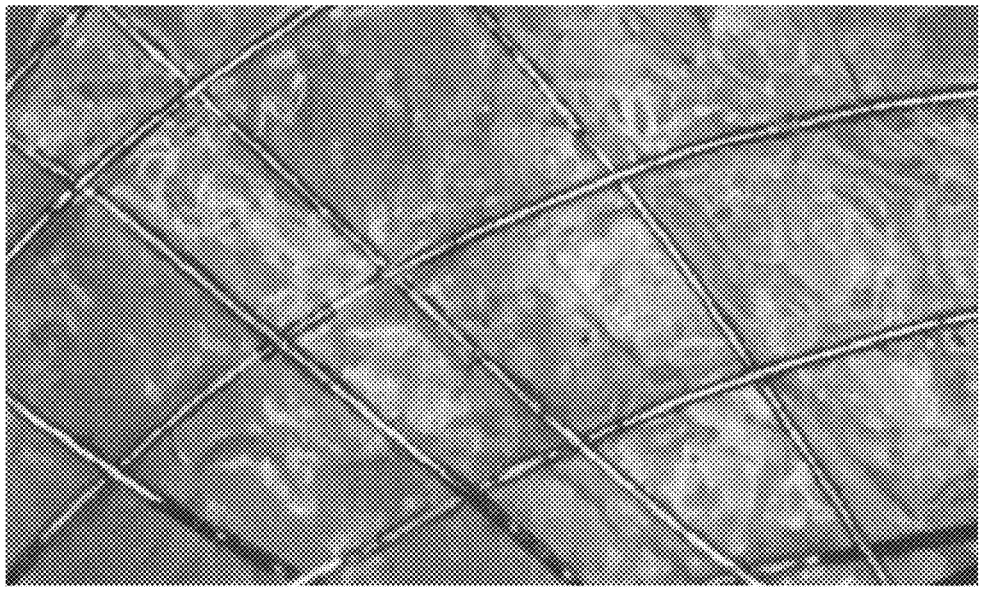
Figure 11B:
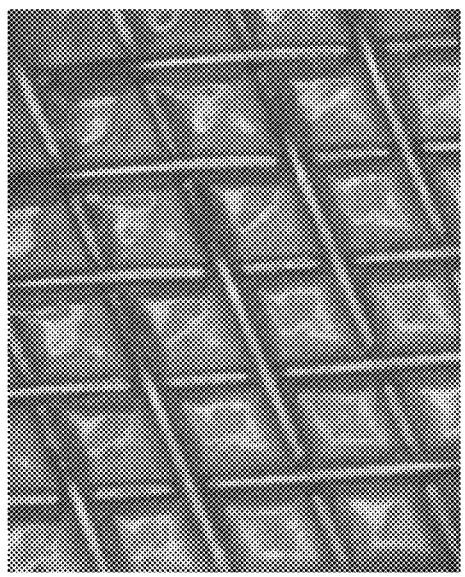
Figure 11C:
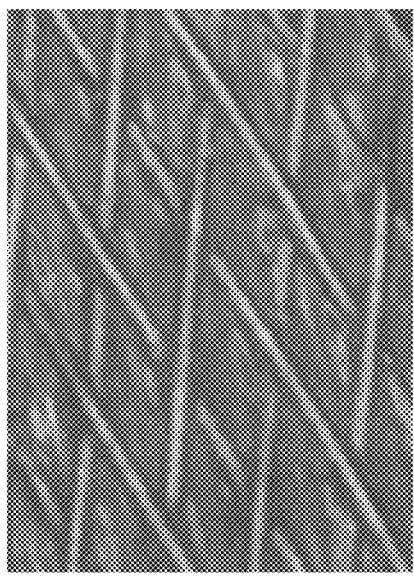

The sleeve 60 may be formed of a polymeric material such as a fluoropolymer (e.g., a highly elastic fluoropolymer or fluoroelastomer), including, for example, fluorinated ethylene propylene (FEP), polytetrafluoroethylene (PTFE), polyvinylidene fluoride (PVDF), or poly(vinylidene fluoride co-hexafluoropropylene) (PVDF-HFP) copolymers. In some embodiments, the sleeve may comprise polydimethylsiloxane (PDMS) or PDMS mixed with another polymer such as one of the aforementioned fluoropolymers. For example, PDMS may be mixed with PVDF-HFP to form a base layer, which may optionally be coated with another layer of PVDF-HFP. PDMS may provide suitable flexibility to the device coating. Other suitable silicones (e.g., silastics) may be used as well. In some embodiments, the sleeve 60 and/or coating applied to the interstitial gaps of the mesh of device 10 will comprise a highly elastic material (e.g., a fluoroelastomer). The elastic properties of the sleeve 60 and/or coating may advantageously allow expansion of the device 10 without breaking, rupturing, tearing, or otherwise damaging the sleeve 60 and/or coating. FIG. 11B depicts a close-up image of the mesh of device 10 comprising a coating of PDMS applied to one side of the device 10 in a relatively unexpanded configuration extending between struts. FIG. 11C depicts a close-up image of the mesh of device 10 comprising a coating of PDMS applied to one side of the device 10 in a relatively expanded configuration. As seen in FIG. 11C, the PDMS coating may be stretched without damaging the coating or ripping the coating from the device 10.

In some embodiments, block copolymers may be used to effectively provide a coating of modulated properties. For example, an A-B-A triblock copolymer may be used. In some embodiments, the A-block may comprise tetrafluoroethylene (TFE), ethylene, and hexafluoropropylene (HFP) (e.g., in approximately 40:43:8 molar ratios). The B-block may comprise vinylidene fluoride (VDF), HFP, and TFE (e.g., in approximately 5:3:2 molar ratios). The A block may comprise about 15% of the weight of the triblock copolymer and the B block may comprise about 85% of the weight of the triblock copolymer. The A-block may provide a relatively hard segment and/or the B-block may provide a relatively flexible segment. The tri-block polymer may be dissolved in an organic solvent and applied to device 10 via compression molding and/or hot melt extrusion (e.g., at about 230° C.). In some embodiments, the polymer can be dissolved and then recast into a thin film. In some embodiments, the device 10 may be heated on a mandrel, such as mandrels described elsewhere herein for manufacturing the device 10, and the polymer (which may be in pellet form) may be applied to the heated device by applying pressure to press the polymer into and/or onto the device 10. The polymer may additionally or alternatively be heated prior to applying to the device 10. FIG. 11D depicts a close-up image of the mesh of device 10 comprising a coating of the A-B-A triblock polymer described above applied to one side of the device 10 in a relatively expanded configuration. As seen in FIG. 11D, the A-B-A triblock polymer coating may be stretched without damaging the coating or ripping the coating from the device 10.

The sleeve 60 may or may not be coated with its own thromboresistant coating, including, but not limited to, coatings comprising polyvinylpyrrolidone (PVP), phosphorylcholine (PC), polyethylene glycol (PEG), and/or hydrophilic Serene™ coatings (provided by Surmodics). Furthermore, any coating described for use in coating the device 10 directly may also be used to coat the sleeve 60, where suitable. In embodiments where a thromboresistant coating is applied to the sleeve 60, the sleeve 60 may be made of less biocompatible materials. In some embodiments, the sleeve 60 may be made from polyethylene oxide (PEO)—impregnated polyurethanes, such as Hydrothane or Tecophilic PU, which will endow the sleeve with thromboresistant properties without the need for a coating. Similarly, a silastic (e.g., PDMS) sleeve 60 may be impregnated with thromboresistant surface modifying molecules (e.g., SAMs), such as fluorinated or PEG-ylated molecules, including those described elsewhere herein for use in coatings or sleeves.

The sleeve 60 may be applied to (e.g., carried by) the internal surface of the device 10 surrounding the central lumen 40, to the outer surface of the device 10, or to both the internal surface and the outer surface. If applied to both, the inner and outer sleeves 60A, 60B may be of the same or different materials, lengths, thicknesses, and/or other properties and may sandwich the struts of the sidewall between the two sleeves 60A, 60B. In some embodiments, the inner diameter may comprise a thicker coating or more coatings than the outer diameter of the device 10. The inner diameter may be coated to form a smoother surface than the outer diameter. This may be accomplished by thicker and/or multiple coatings. The smoother surface may provide a less thrombogenic surface.

The sleeve 60 may be applied to the device 10 by dip-coating, by wrapping the sleeve around the device, and/or any other suitable means. In some implementations, applying multiple thin coatings (as opposed to a single coating of equivalent thickness) may provide superior mechanical properties, such as flexibility/expandability. In some embodiments, the sleeve 60 may adhere to the device 10. In some embodiments, the sleeve 60 may be frictionally retained to the device 10. The sleeve 60 may be melt pressed onto the device 10, and inner and outer sleeves 60A, 60B may be melted or otherwise bonded together in the interstitial spaces or gaps of the side wall of the device 10. In some embodiments, the sleeve 60 extends the length of the central section 20 of the device 10, although it need not extend the entire length. In some embodiments, the sleeve 60 extends the entire length of the device (e.g., covering tapered proximal and distal sections 28, 30). The sleeve 60 may be made porous, preferentially towards its proximal and distal ends (e.g., 10%, 20%, 30%, 40%, etc. of the length on each side), by providing holes through the sleeve 60, which may advantageously allow blood flow through side branching blood vessels near the aneurysm. Perforations may be imparted by laser or mechanical perforation through the sleeve 60 or by other suitable means. Perforations may be used to make variable porosity sleeves the same as or similar to perforations applied to the film coating described elsewhere herein. Use of a sleeve 60 may allow use of a lower mesh density (i.e. greater porosity) in the underlying device 10 (e.g., 25%, 30%, 40%, 50% porosity or greater).

In some embodiments, the sleeve 60 and/or coating may be applied to the entire length of the device 10. The sleeve 60 and/or coating may provide coverage over all or substantially all of the interstitial gaps in the mesh of the device 10. In some embodiments, the coating may be applied only over a portion of the device 10. For example, the sleeve 60 and/or coating 11 may be applied over a middle section of the device configured to be placed proximate the aneurysm (e.g., the middle 10%, 20%, 25%, 30%, 40%, 50%, etc. of the device). In some embodiments, selective sections of the device may be coated. FIG. 11E schematically illustrates the device 10 in which selective interstitial gaps are coated (indicated by dark sections). In some embodiments, various rows (e.g., alternating rows of spiraling mesh cells) are coated. In some embodiments, various blocks of cells are coated. In some implementations, the selective coating is formed by selectively applying the coating to various portions of the device 10. In some implementations, the sleeve or coating is applied over the entire device 10 or over a portion of the device 10 and the selective coating is formed by removing (e.g., cutting out) the coating from selective sections of the mesh device 10. Applying the coating to only selective regions of the device may facilitate movement of the device (e.g., expansion) without ripping or otherwise damaging the coating.

In some embodiments, the device 10 is self-expanding and does not require a balloon for deployment, such that the blood vessel is never occluded during the operation, which could lead to additional complications. In alternative embodiments, the device 10 is expanded by a non-occlusive perfusion balloon, such as a hollow balloon. For instance, the balloon may be fabricated as a tube with a lumen extending from the proximal to distal end or may be formed of a ring of cylindrical balloons. Alternatively, the balloon may take the form of a flower, with pedal-like protrusions abutting the vessel wall and surrounding a lumen extending from the proximal to distal end or could be a C-shaped balloon, in which the balloon presses against the aneurysm neck, but not necessarily against the entire circumference of the blood vessel. A coiling spring-shaped balloon, similar to the coil device depicted in FIGS. 8A-8D, may be used in combination with a tightening piece, such as a tether, to pull the spring together. In alternative embodiments, the balloons could replace the metal wire devices altogether. Still in further alternative embodiments, a hollow self-expanding sponge or hollow hydrogel could be used to supplant the device 10.

In some embodiments, the microcatheter for delivering coils into the aneurysm is inserted into the aneurysm prior to the implantation of the device 10. Following insertion of the coil microcatheter, a guidewire may be aligned within the blood vessel along the coil microcatheter and used to track a second microcatheter to a position near the aneurysm. The guidewire may be removed and the device may be delivered through the second microcatheter. Once in proper position, the microcatheter sheath may be retracted from the device 10 to deploy the device 10 such that the coil microcatheter is entrapped between the blood vessel wall and the outer diameter of the device, extending into the aneurysm. Alternatively, the microcatheters may be deployed simultaneously.

Figure 12B:
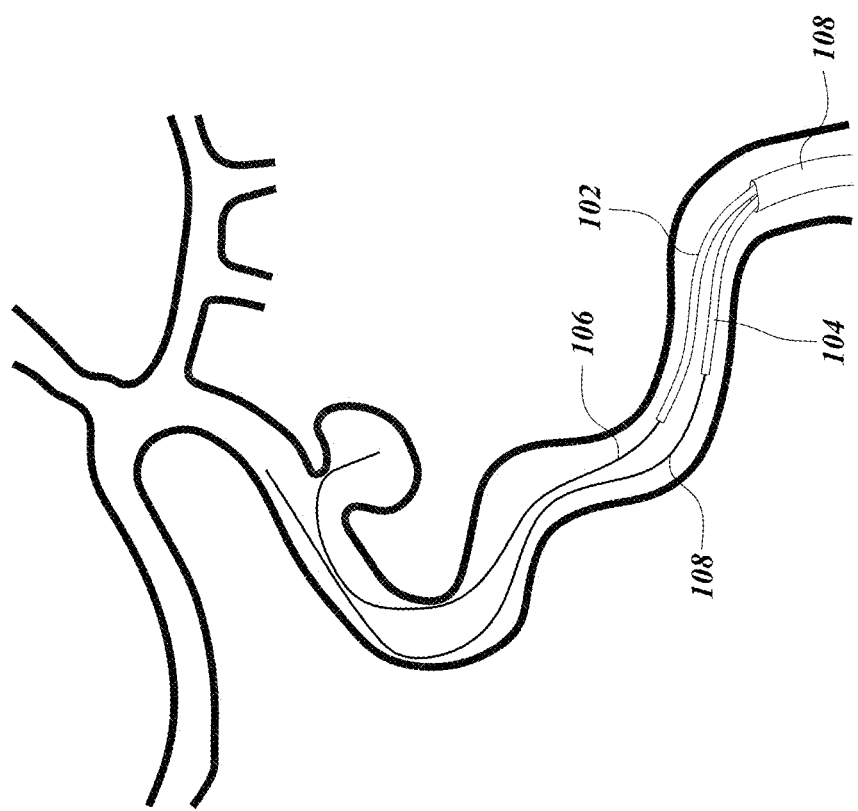
FIGS. 12A-12I show the general progression of a method of deploying coils as well as the aneurysm treatment device.
Figure 12A:
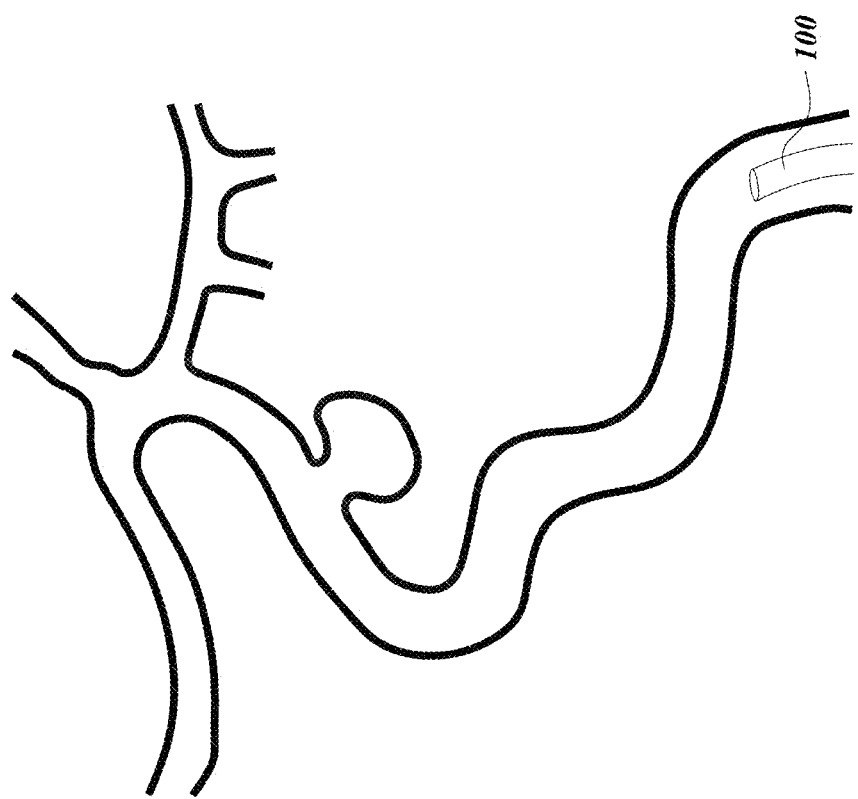
Figure 12D:
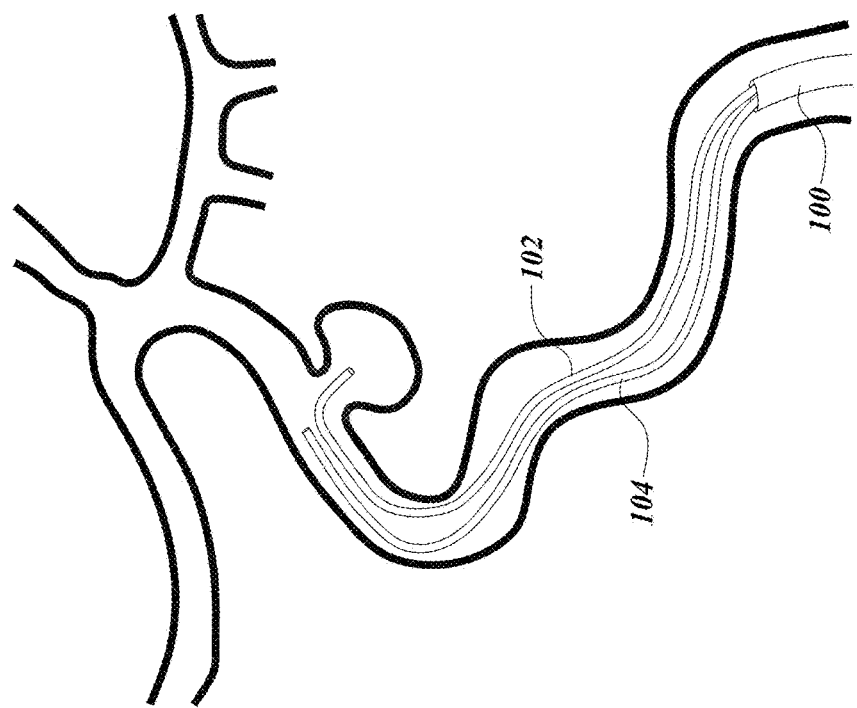
Figure 12C:
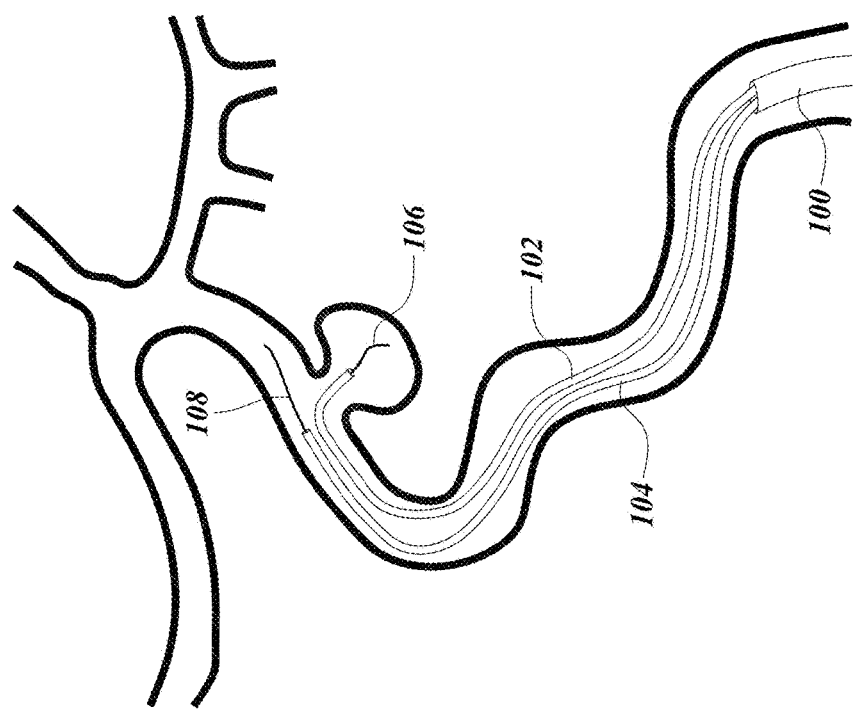
Figure 12F:
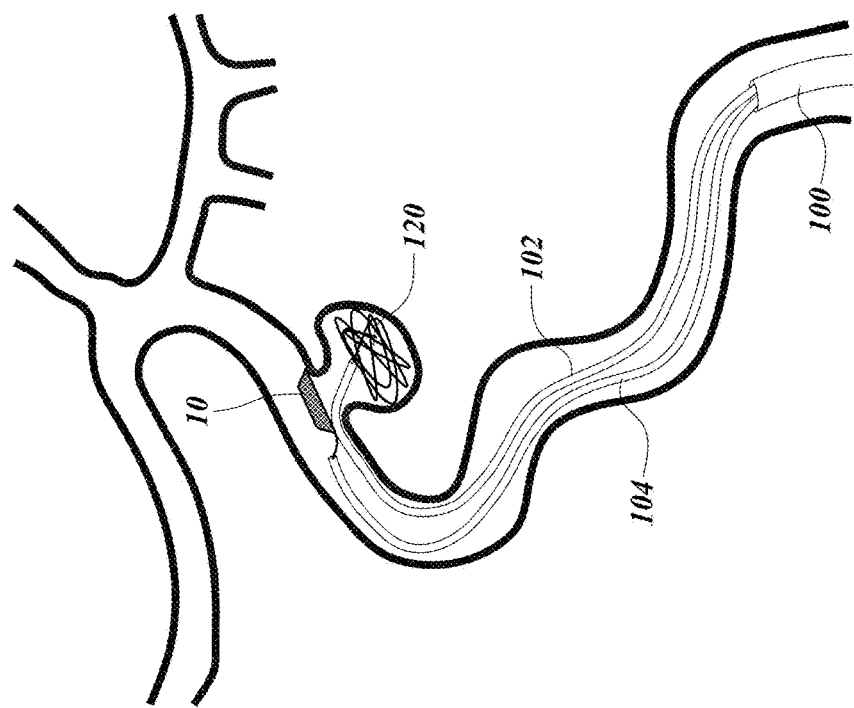
Figure 12E:
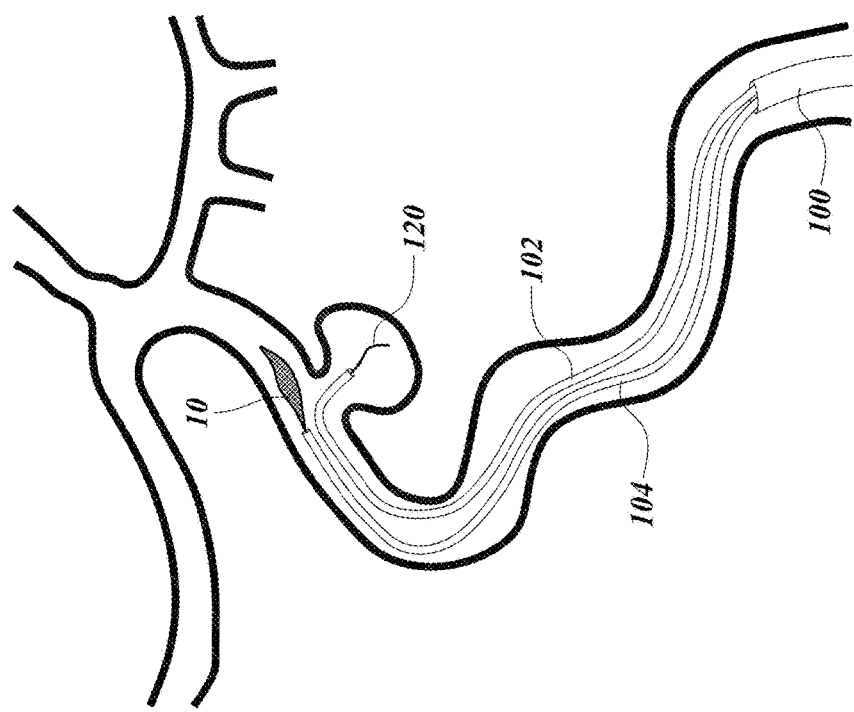
Figure 12H:
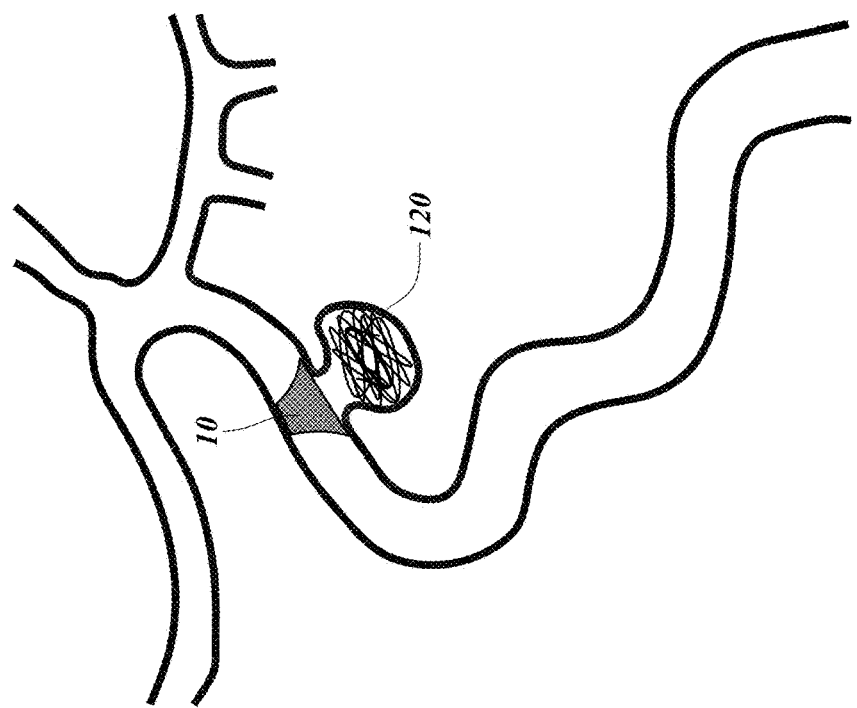
Figure 12G:
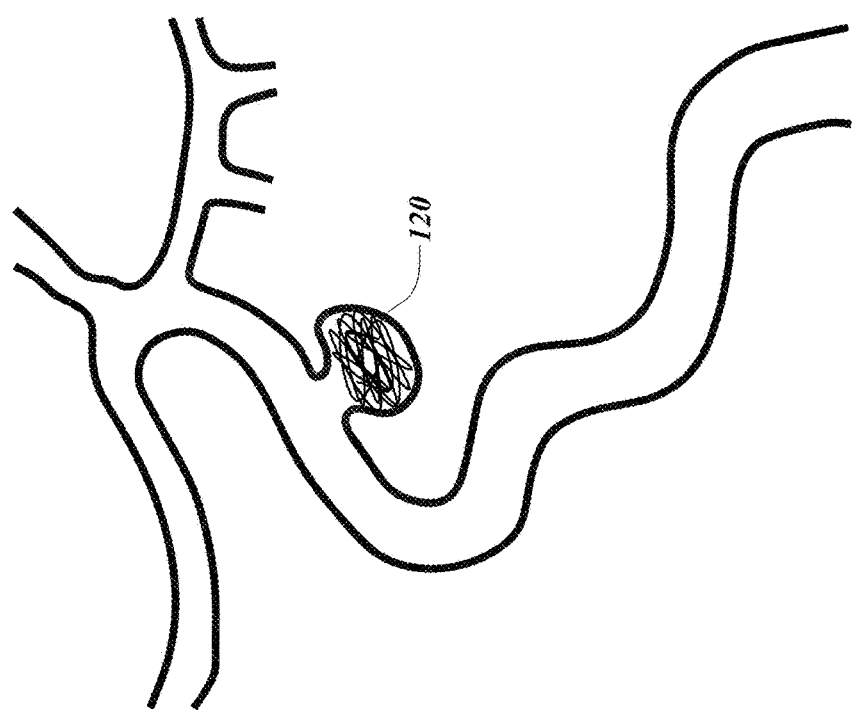
Figure 12I:
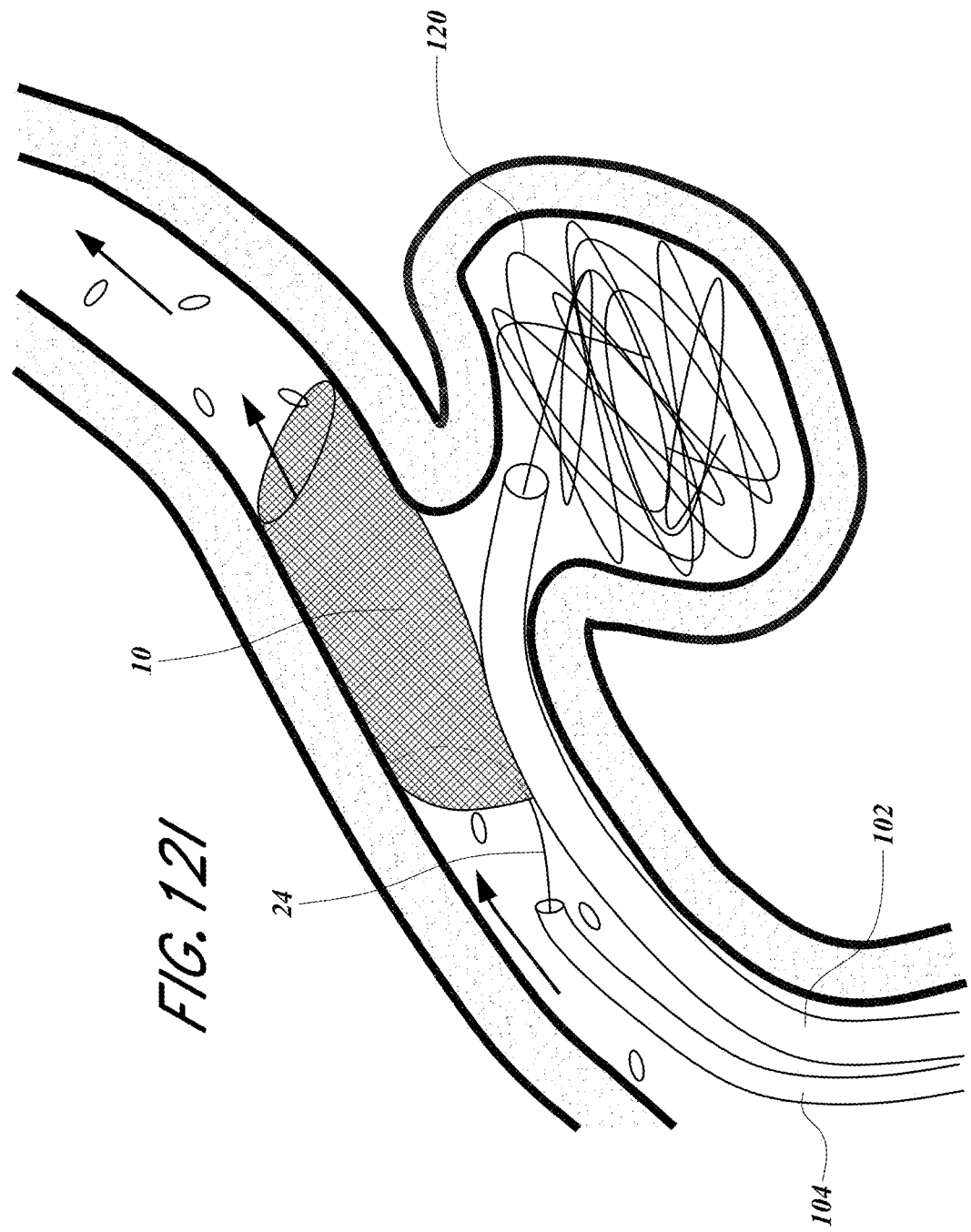

A general, but non-limiting method of deployment is illustrated in FIGS. 12A-12I. FIGS. 12A-12I show the general progression of a method of deploying coils 120 as well as the aneurysm treatment device 10. FIG. 12A shows use of a delivery catheter 100 to establish a path to the aneurysm. FIG. 12B shows use of microwires 106, 108 to help guide delivery catheters 102, 104 for both the coils 120 and device 110 to the aneurysm. FIG. 12C shows the placement of the coil delivery catheter 102 in the aneurysm for delivering the coils 120 and the device delivery catheter 104 in the blood vessel next to the aneurysm for placing the device 10. FIG. 12D shows the catheters 102, 104 upon removal of the microwires 106, 108. FIG. 12E shows the deployment of the device 10 and a coil 120 from the respective catheters 104, 102. FIG. 12F shows the expanded device 10 upon deployment and the aneurysm upon being packed with coils 120. FIG. 12G shows the packed aneurysm after the catheters 102, 104 are retracted and the coil assist device 10 is removed. FIG. 12H alternatively shows the packed aneurysm with a permanent device 10 implanted next to the aneurysm in the blood vessel after the catheters 102, 104 are retracted. FIG. 12I schematically shows a close-up view of the deployment of the coils 120 and the coil assist device 10 after deployment with blood flow being maintained through the coil assist device 10.

The device 10 may self-expand upon retraction of the microcatheter sheath 104. In some embodiments, the device 10 is further releasably tethered to a push wire and may be released by a mechanical mechanism (e.g., a pull wire or sheath) or electrolytic degradation of a juncture between the push wire and the implant body. Such mechanisms may allow the device 10 to be easily re-sheathed and repositioned if desired prior to detachment from the push wire. After the device 10 is deployed, coils 120 may be delivered through the coil delivery microcatheter 102 that has been previously positioned in the aneurysm. Alternatively, the coil microcatheter 102 may be inserted down the lumen 40 of the device 10 and through the device mesh into the aneurysm, after the device is deployed. For instance, the coil microcatheter 102 may be inserted directly through the mesh of the spherical intermediate section 22 depicted in FIGS. 2A-2C.

The microcatheter 104 for delivery of the device 10 may be composed of any suitable material. In some embodiments, the microcatheter 104 is fabricated from or includes a swellable, hydrophilic polyurethane. Polyurethane allows modulation of the microcatheter flexibility and surface lubricity. The swellable nature of polyurethane can endow the catheter with an additional design features by shaping the proximal end appropriately. In other embodiments, the microcatheter 104 is coated with a hydrophilic coating, such as a polyvinylpyrrolidone (PVP)-based photochemically activated coating. Such a coating allows the bulk properties of the microcatheter 104 to be designed independently of surface properties, as the coating provides predictably biocompatible interactions with the physiological environment.

In some embodiments, the device 10 is designed only to assist in deployment of the coils 120 and may be removed after packing of the coils 120 in the aneurysm. The coil assist device 10 may optionally then be replaced by a permanent device, (e.g. a neurovascular stent) which may be of substantially similar design or of a different design. Alternatively, the device 10 may serve as a permanent device which remains in place after deployment and packing of the aneurysm coils.

FIGS. 13A-13B depict examples of an aneurysm treatment device 10 composed of braided wire to form a braided mesh device 200, which may the same or similar to embodiments described elsewhere herein. In some embodiments, the braided mesh device 200 may be formed from braided nitinol wire. The mesh device 200 may be formed in a generally cylindrical shape. In some embodiments, the proximal and/or distal tails of the mesh device 200 may be inverted such that one or more wires bend radially outward and toward proximal apex 26 (folding over other wires) within the proximal tapered section 28. The wires may form multiple layers of mesh as they fold over one another. FIG. 13A illustrates a nitinol mesh 200 comprising inverted mesh tails within proximal and distal tapered sections 28, 30. Inversion of the mesh tails of the mesh device 200 can create a more patent device lumen by positioning the proximal and/or distal ends of the mesh wire strands outside an inner diameter of the device lumen. This configuration may maximize the patency of the mesh lumen, which may reduce thrombogenicity.

In some embodiments, the wires may not be inverted. FIG. 13B illustrates an example of a mesh device without inverted tails in either the proximal or distal tapered sections 28, 30. In some embodiments, the wires may be otherwise bent or shaped within the proximal tapered section 28 and/or distal tapered section 30 to maximize the patency of the device lumen. For example, wires may bend radially inward as they extend toward the proximal apex 26, which may form multiple layers of mesh. As more layers of mesh begin to overlap towards the proximal apex 26, the outer diameter of the proximal tapered section may bend, arc, bulge, or pop-out in a radially outward direction such that the overlapping layers of mesh do not bulge inwardly within the cross-sectional area defined by the device lumen. In some embodiments, the layers of mesh may be pressed tightly together so that any outward bulge is negligible.

The wires within the proximal tapered section 28 of the mesh device 200 may be evenly distributed circumferentially. For example, half the wires may extend in a clockwise direction as they leave the proximal or distal apex and half the wires may extend in a counterclockwise direction as they leave the proximal or distal apex. In some embodiments, the wire braids (overlapping/intersecting wires) may be uniformly distributed such that the spacing between intersecting wires is relatively regular. For instance, the wires may be disposed such that the shape (e.g., diamond shape) and/or area of the interstitial gaps within the proximal tapered section is relatively consistent. In some embodiments, the wires may be positioned so that there is a regular spacing of wires around an edge of the proximal tapered section which the blood flow interfaces as it flows into the device (e.g., the edge defining the take-off angle described elsewhere herein). Regular spacing of the braided wires within the tapered section or sections may advantageously provide optimal structural integrity (e.g., hoop rigidity) within the tapered section or sections.

The shape of the device 10 when fabricated from shape memory materials (e.g., nitinol or shape-memory polymers) may be thermally set in an expanded configuration configured to occupy the blood vessel lumen and at least partially press against the aneurysm neck. The mesh 200 may be elastically deformed by axially stretching the device which may axially lengthen the device and collapse or reduce the cross-section of the mesh device lumen. The mesh device may be loaded into a microcatheter or delivery device in the collapsed configuration. Upon release from the delivery device, the mesh device may self-expand to assume the memorized shape-set configuration determined during the heating step. The transition temperature of the shape memory material may be below room temperature, room temperature, between room temperature and physiological temperature, or physiological temperature.

While certain embodiments of the disclosure have been described, these embodiments have been presented by way of example only, and are not intended to limit the scope of the disclosure. Indeed, the novel methods, systems, and devices described herein may be embodied in a variety of other forms. Moreover, the coatings and devices described above may be utilized for other purposes. Furthermore, various omissions, substitutions and changes in the form of the methods, systems, and devices described herein may be made without departing from the spirit of the disclosure.

One or more of the features illustrated in the drawings and/or described herein may be rearranged and/or combined into a single component or embodied in several components. Additional components may also be added. While certain example embodiments have been described and shown in the accompanying drawings, it is to be understood that such embodiments are merely illustrative and not restrictive. Thus, the inventions are not limited to the specific constructions and arrangements shown and described, since various other modifications may occur to those ordinarily skilled in the art based on the present disclosure.

Various operations of methods described above may be performed by any suitable means capable of performing the operations. Generally, any operations illustrated in the Figures may be performed by corresponding functional means capable of performing the operations.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims. Method step and/or actions disclosed herein can be performed in conjunction with each other, and steps and/or actions can be further divided into additional steps and/or actions.

It is to be understood that the claims are not limited to the precise configuration and components illustrated above. Various modifications, changes and variations may be made in the arrangement, operation and details of the methods and apparatus described above.

What is claimed is:

1. A device for insertion into a blood vessel lumen for treatment of an aneurysm, comprising:
a generally cylindrical section comprising a plurality of struts forming interstitial gaps between the struts, the generally cylindrical section having a proximal face and a distal face and defining a device lumen extending along an axial direction from the proximal face to the distal face, the lumen being configured to allow blood flow through the device, the generally cylindrical section being configured to provide a radially outward counter force to compression adjacent the proximal face which is greater than a radially outward counter force to compression near a middle of the generally cylindrical section; and
a proximal tapered section comprising a plurality of struts extending from a circumference of the proximal face to a proximal apex,
wherein the proximal apex is radially aligned with the circumference of the proximal face or positioned radially outside the circumference of the proximal face, and
wherein the plurality of struts of the proximal tapered section extend from different points on the circumference of the proximal face in an axial and circumferential direction to the proximal apex, such that none of the plurality of struts cross through a cross-sectional area defined by the device lumen.

2. The device of claim 1, wherein the plurality of struts of the generally cylindrical section and the proximal tapered section are formed from braided wires which are at least partially braided within the proximal tapered section.

3. The device of claim 2, wherein at least a portion of each of the plurality of struts within the proximal tapered section are aligned in a parallel fashion proximal to the proximal apex, wherein a proximal end of each of the plurality of struts is joined to a distal end of a push wire at a location collinear with the proximal apex, and wherein the proximal ends of each of the plurality of struts are substantially uniformly distributed around a circumference of the push wire.

4. The device of claim 3, wherein the push wire is permanently joined to the proximal tapered section.

5. The device of claim 3, wherein the push wire is detachably joined to the proximal tapered section.

6. The device of claim 3, wherein the distal end of the push wire comprises a tapered portion.

7. The device of claim 3, wherein the distal end of the push wire comprises a plurality of plastic rings surrounding the push wire, the proximal ends of the plurality of struts from the proximal tapered section surrounding the plastic rings.

8. The device of claim 2, wherein the plurality of struts of the generally cylindrical section and the proximal tapered section are formed from 24 braided wires.

9. The device of claim 1, wherein one or more of the plurality of struts of the proximal tapered section are inverted within the proximal tapered section such that one or more of the inverted struts bend radially outward of the circumference of the proximal face such that the proximal apex is positioned radially outside the circumference of the proximal face.

10. The device of claim 1, wherein the plurality of struts of the proximal tapered section form an edge extending from or near the proximal apex and extending to the circumference of the proximal face configured to interface incoming blood flow, and wherein the edge defines a take-off angle relative to a longitudinal axis extending through the proximal apex parallel to the axial dimension, the take-off angle being no greater than about 80 degrees.

11. The device of claim 10, wherein the take-off angle is at least about 30 degrees.

12. The device of claim 1, wherein the plurality of struts of the proximal tapered section and the generally cylindrical section have a diameter of no greater than about 0.01 inches.

13. The device of claim 1, wherein the generally cylindrical section comprises a middle section configured to be positioned adjacent the aneurysm, wherein the middle section comprises a substantially higher strut density than at least a portion of the remainder of the generally cylindrical section.

14. The device of claim 13, wherein the middle section comprises an outer diameter that is larger than an outer diameter of the proximal face in an unconstrained configuration.

15. The device of claim 1, wherein the interstitial gaps are no greater than about 0.01 inches across.

16. The device of claim 1, further comprising a distal tapered section comprising a plurality of struts extending from a circumference of the distal face to a distal apex,
wherein the distal apex is radially aligned with the circumference of the distal face or positioned radially outside the circumference of the distal face, and
wherein the plurality of struts of the distal tapered section extend from different points on the circumference of the distal face in an axial and circumferential direction to the distal apex, such that none of the plurality of struts cross through a cross-sectional area defined by the device lumen.

17. The device of claim 1, wherein the distal face is open and substantially perpendicular to the axial direction.

18. The device claim 1, wherein the plurality of struts within the proximal tapered section are distributed substantially uniformly around the circumference of the proximal face.

19. The device of claim 1, further comprising a polymeric sleeve positioned around at least a portion of the device lumen.

20. The device of claim 19, wherein the sleeve comprises apertures positioned near a proximal end of the sleeve and near a distal end of the sleeve but not within a middle section of the sleeve.

21. The device of claim 19, wherein the sleeve comprises fluorinated ethylene propylene (FEP), polytetrafluoroethylene (PTFE), polyvinylidene fluoride (PVDF), or poly(vinylidene fluoride co-hexafluoropropylene) (PVDF-HFP).

22. The device of claim 19, wherein the sleeve comprises an A:B:A triblock copolymer, the A block comprising tetrafluoroethylene (TFE), ethylene, and hexafluoropropylene (HFP) and the B block comprising vinlidene fluoride (VDF), hexafluoropropylene (HFP), and tetrafluoroethylene (TFE).

23. The device of claim 19, wherein the sleeve is impregnated with or coated with polyvinylpyrrolidone (PVP), phosphorylcholine (PC), polyethylene glycol (PEG), Serene™, PEG-ylated molecules, or fluorinated molecules to provide a thromboresistant surface.

24. The device of claim 1, wherein the device comprises an internal surface with an internal diameter and an outer surface with an outer diameter, wherein the device further comprises a first coating applied to the inner surface and a second coating applied to the outer surface, and wherein the first and second coatings having distinct biological properties.

25. The device of claim 24, wherein the first coating is designed primarily to reduce thrombus formation and the second coating is designed primarily to promote endothelialization.

26. The device of claim 1, wherein the plurality of struts of the generally cylindrical section are coated with a coating forming a gradient in at least one biological property along a length of the device in a direction aligned with the axial direction, wherein the at least one biological property comprising reduction of thrombus formation and promotion of endothelialization, and wherein the reduction of thrombus formation increases as promotion of endothelialization decreases.

27. The device of claim 1, wherein the plurality of struts of the generally cylindrical section are coated with polytetrafluoroethylene (PTFE), polyvinylidene fluoride (PVDF), polyvinylidene-hexafluoropropylene (PVDF-HFP), perfluoropropylene, octafluoropropane, Parylene HT, Parylene AF-4, Parylene F, Parylene VT-4; 1H,1H,2H,2H-perfluorododecyltrichlorosilane, (tridecafluoro-1,1,2,2, tetrahydrooctyle) silane, hexadecafluordodec-11-en-1-yl trimethoxysilane, or a poly(p-xylylene) polymer.

28. The device of claim 1, wherein the proximal apex is positioned radially outside the circumference of the proximal face.

29. A device for insertion into a blood vessel lumen for treatment of an aneurysm, comprising:
a generally cylindrical section comprising a plurality of struts forming interstitial gaps between the struts, the generally cylindrical section having a proximal face and a distal face and defining a device lumen extending along an axial direction from the proximal face to the distal face, the lumen being configured to allow blood flow through the device; and
a proximal tapered section comprising a plurality of struts extending from a circumference of the proximal face to a proximal apex, wherein the proximal apex is radially aligned with the circumference of the proximal face or positioned radially outside the circumference of the proximal face, and wherein the plurality of struts of the proximal tapered section extend from different points on the circumference of the proximal face in an axial and circumferential direction to the proximal apex, such that none of the plurality of struts cross through a cross-sectional area defined by the device lumen, wherein the plurality of struts of the generally cylindrical section are coated with a coating forming a gradient in at least one biological property along a length of the device in a direction aligned with the device lumen, wherein the at least one biological property comprises reduction of thrombus formation and promotion of endothelialization, and wherein the reduction of thrombus formation increases as promotion of endothelialization decreases.

30. The device of claim 29, wherein the cylindrical section comprises a wire weave.

31. The device of claim 29, wherein the plurality of struts of the generally cylindrical section and the proximal tapered section are formed from braided wires which are at least partially braided within the proximal tapered section.

32. The device of claim 31, wherein the interstitial gaps are no greater than about 0.01 inches across.

33. The device of claim 31, wherein the plurality of struts of the generally cylindrical section and the proximal tapered section are formed from 24 braided wires.

34. The device of claim 31, wherein at least a portion of each of the plurality of struts within the proximal tapered section are aligned in a parallel fashion proximal to the proximal apex, wherein a proximal end of each of the plurality of struts is joined to a distal end of a push wire at a location collinear with the proximal apex, and wherein the proximal ends of each of the plurality of struts are substantially uniformly distributed around a circumference of the push wire.

35. The device of claim 34, wherein the push wire is permanently joined to the proximal tapered section.

36. The device of claim 34, wherein the push wire is detachably joined to the proximal tapered section.

37. The device of claim 34, wherein the distal end of the push wire comprises a tapered portion.

38. The device of claim 34, wherein the distal end of the push wire comprises a plurality of plastic rings surrounding the push wire, the proximal ends of the plurality of struts from the proximal tapered section surrounding the plastic rings.

39. The device of claim 29, wherein one or more of the plurality of struts of the proximal tapered section are inverted within the proximal tapered section such that one or more of the inverted struts bend radially outward of the circumference of the proximal face such that the proximal apex is positioned radially outside the circumference of the proximal face.

40. The device of claim 29, wherein the plurality of struts of the proximal tapered section form an edge extending from or near the proximal apex and extending to the circumference of the proximal face configured to interface incoming blood flow, and wherein the edge defines a take-off angle relative to a longitudinal axis extending through the proximal apex parallel to the axial dimension, the take-off angle being no greater than about 80 degrees.

41. The device of claim 40, wherein the take-off angle is at least about 30 degrees.

42. The device of claim 29, wherein the plurality of struts of the proximal tapered section and the generally cylindrical section have a diameter of no greater than about 0.01 inches.

43. The device of claim 29, wherein the middle section comprises an outer diameter that is larger than an outer diameter of the proximal face in an unconstrained configuration.

44. The device of claim 29, further comprising a distal tapered section comprising a plurality of struts extending from a circumference of the distal face to a distal apex, wherein the distal apex is radially aligned with the circumference of the distal face or positioned radially outside the circumference of the distal face, and wherein the plurality of struts of the distal tapered section extend from different points on the circumference of the distal face in an axial and circumferential direction to the distal apex, such that none of the plurality of struts cross through a cross-sectional area defined by the device lumen.

45. The device of claim 29, wherein the distal face is open and substantially perpendicular to the axial direction.

46. The device of claim 29, wherein the plurality of struts within the proximal tapered section are distributed substantially uniformly around the circumference of the proximal face.

47. The device of claim 29, further comprising a polymeric sleeve positioned around at least a portion of the device lumen.

48. The device of claim 47, wherein the sleeve comprises apertures positioned near a proximal end of the sleeve and near a distal end of the sleeve but not within a middle section of the sleeve.

49. The device of claim 47, wherein the sleeve comprises fluorinated ethylene propylene (FEP), polytetrafluoroethylene (PTFE), polyvinylidene fluoride (PVDF), or poly(vinylidene fluoride co-hexafluoropropylene) (PVDF-HFP).

50. The device of claim 47, wherein the sleeve comprises an A:B:A triblock copolymer, the A block comprising tetrafluoroethylene (TFE), ethylene, and hexafluoropropylene (HFP) and the B block comprising vinlidene fluoride (VDF), hexafluoropropylene (HFP), and tetrafluoroethylene (TFE).

51. The device of claim 47, wherein the sleeve is impregnated with or coated with polyvinylpyrrolidone (PVP), phosphorylcholine (PC), polyethylene glycol (PEG), Serene™, PEG-ylated molecules, or fluorinated molecules to provide a thromboresistant surface.

52. The device of claim 29, wherein the device comprises an internal surface with an internal diameter and an outer surface with an outer diameter, wherein the device further comprises a first coating applied to the inner surface and a second coating applied to the outer surface, and wherein the first and second coatings having distinct biological properties.

53. The device of claim 52, wherein the first coating is designed primarily to reduce thrombus formation and the second coating is designed primarily to promote endothelialization.

54. The device of claim 29, wherein the plurality of struts of the generally cylindrical section are coated with polytetrafluoroethylene (PTFE), polyvinylidene fluoride (PVDF), polyvinylidene-hexafluoropropylene (PVDF-HFP), perfluoropropylene, octafluoropropane, Parylene HT, Parylene AF-4, Parylene F, Parylene VT-4; 1H,1H,2H,2H-perfluorododecyltrichlorosilane, (tridecafluoro-1,1,2,2, tetrahydrooctyle) silane, hexadecafluordodec-11-en-1-yl trimethoxysilane, or a poly(p-xylylene) polymer.

55. The device of claim 29, wherein the proximal apex is positioned radially outside the circumference of the proximal face.

\* \* \* \* \*